(12) United States Patent
Taintor

(10) Patent No.: US 7,018,828 B1
(45) Date of Patent: Mar. 28, 2006

(54) MICROBIAL CULTURE MEDIUM CONTAINING AGAR AND IOTA CARRAGEENAN

(76) Inventor: Read Taintor, 98 Mason La., North Salt Lake, UT (US) 84054

( * ) Notice: Subject to any disclaimer, the term of this patent is extended or adjusted under 35 U.S.C. 154(b) by 325 days.

(21) Appl. No.: 10/462,131

(22) Filed: Jun. 16, 2003

Related U.S. Application Data

(63) Continuation-in-part of application No. 10/036,042, filed on Nov. 9, 2001, now abandoned.

(51) Int. Cl.
| | |
|---|---|
| *C12N 1/00* | (2006.01) |
| *C12N 1/14* | (2006.01) |
| *C12N 1/16* | (2006.01) |
| *C12N 1/18* | (2006.01) |
| *C12N 1/20* | (2006.01) |

(52) U.S. Cl. ............... 435/253.6; 435/243; 435/255.21; 435/255.7; 435/256.8

(58) Field of Classification Search ................. 435/243, 435/253.6, 255.21, 255.7, 256.8
See application file for complete search history.

(56) References Cited

U.S. PATENT DOCUMENTS

| | | | |
|---|---|---|---|
| 3,715,280 A | | 2/1973 | Farmer, III |
| 4,090,920 A | | 5/1978 | Studer, Jr. |
| 4,275,154 A | * | 6/1981 | Hall ............................ 435/32 |
| 4,701,850 A | | 10/1987 | Gibbs |
| 5,336,600 A | | 8/1994 | Monget |
| 5,344,761 A | | 9/1994 | Citri |
| 5,464,755 A | | 11/1995 | Bochner |
| 5,627,045 A | | 5/1997 | Bochner et al. |
| 5,789,191 A | | 8/1998 | Mayer et al. |
| 5,882,882 A | | 3/1999 | Bochner et al. |
| 5,922,593 A | | 7/1999 | Livingston |
| 5,989,851 A | | 11/1999 | Self et al. |
| 5,998,214 A | | 12/1999 | Guirguis |
| 6,010,896 A | | 1/2000 | Eisenberg et al. |
| 6,015,941 A | | 1/2000 | Rao |
| 6,046,021 A | | 4/2000 | Bochner |
| 6,130,057 A | | 10/2000 | Gosnell et al. |
| 6,153,400 A | | 11/2000 | Matsumura et al. |
| 6,159,719 A | | 12/2000 | Laine et al. |
| 6,251,624 B1 | | 6/2001 | Matsumura et al. |
| 6,271,001 B1 | | 8/2001 | Clarke et al. |
| 6,280,928 B1 | | 8/2001 | Scholl et al. |
| 6,387,651 B1 | | 5/2002 | Bochner et al. |

OTHER PUBLICATIONS

Webpage, Details of Carrageenan, 2 pages.
Webpage, Carrageenan information, 2 pages.
Webpage, Product Information, Carrageenan, 1 page.
Webpage, Carrageenans, 5 pages.
Webpage, GENU Carrageenan, 12 pages.
Webpage, "Carrageenan: Technical Information," CEAMSA, 3 pages.
Webpage, Definitions, 10 pages.
Webpage, FMC Marine Colloids–Carrageenan, FMC BioPolymer, 3 pages.
Webpage, Introduction to Natural Grade Carrageenan, 8 pages.
The Tic Times, Winter 2002, 4 pages.
Abbott, IA, et al., "Evaluation of Kappa Carrageenan as a Substitute for Agar in Microbiological Media," Arch. Microbiol. Feb. 1981 128 (4) 355–359.
Astier–Gin et al., "Identification of HTLV–1 or HTLV–I-I–Producing Cells by Cocultivation with BHK–21 Cells Stably Transfected with a LTR–lacZ Gene Construct," J. Virological Methods 51:19–30.
Dagan, et al., "A Combination of Four Cell Types for Rapid Detection of Enteroviruses in Clinical Specimens," J. Med. Virol 19: 219–229 (1986).
Lines, AD, "Value of the K+ Salt of Carageenan as an Agar Substitute in Routine Bacteriological Media," Appl. Environ. Microbiol, Dec. 1997; 34 (6) 637–9.
Pittman KA, et al., "Carrageenan: the Effect of Molecular Weight and Polymer Type on its Uptake, Excretion and Degradation in Animals," Food Cosmet Toxicol. Apr. 14, 1976, (2) 85–93.
Rabalais et al., "Rapid Diagnosis of Respiratory Viral Infection by Using a Shell Vial Assay and Monoclonal Antibody Pool," J. Clin. Microbiol. 30:1505–1508 (1992).
Rodriguez, A.I., et al., "Dynamic viscoelastic behavior of gellan–t–carrageenan and gellan–xanthan gels," Food Hydrocolloids, 13 (1999) 59–64.
Watson, N, et al., "Substitute for Agar in Solid Media for Common Usages in Microbiology," Appl. Environ. Microbiol. Apr. 1976, 31 (4) 509–13.

* cited by examiner

*Primary Examiner*—David M. Naff
*Assistant Examiner*—Deborah K. Ware
(74) *Attorney, Agent, or Firm*—Madson & Metcalf

(57) ABSTRACT

Media and kits are disclosed for use in processes requiring microbial culture. More specifically, the invention provides carrageenan-stabilized agar-based microbial culture media and kits constructed using the media. The media and kits of the invention may allow the construction of kits with increased shelf stability and useful life. Further, the media and kits of the invention may be used in kits and methods useful in the manual determination of the type of infection present in a specimen in periods of about 24 hours. The stabilized culture media of the invention are useful in a broad variety of applications. In an embodiment, the media contains both an agar medium and iota carrageenan.

39 Claims, 28 Drawing Sheets

(1 of 28 Drawing Sheet(s) Filed in Color)

FIG. 1
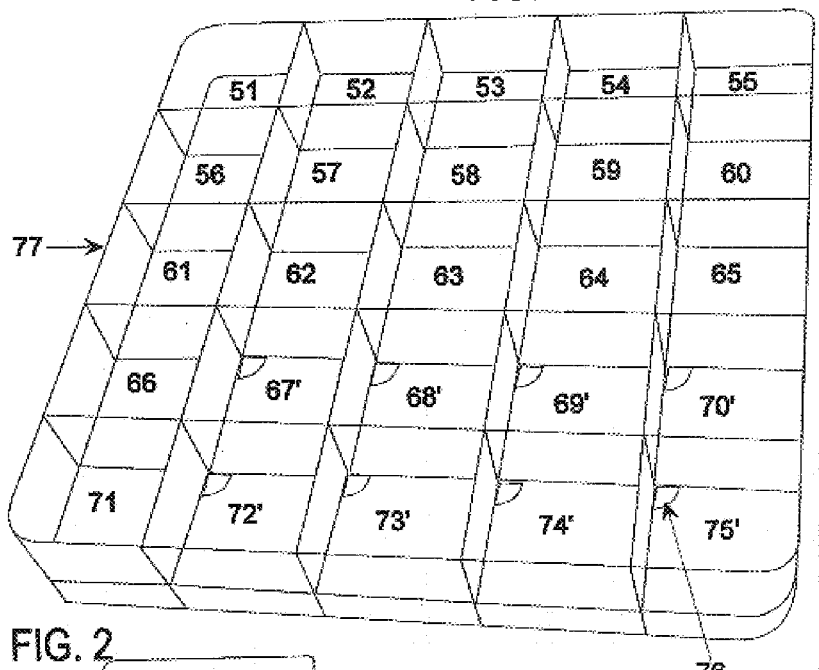
FIG. 2
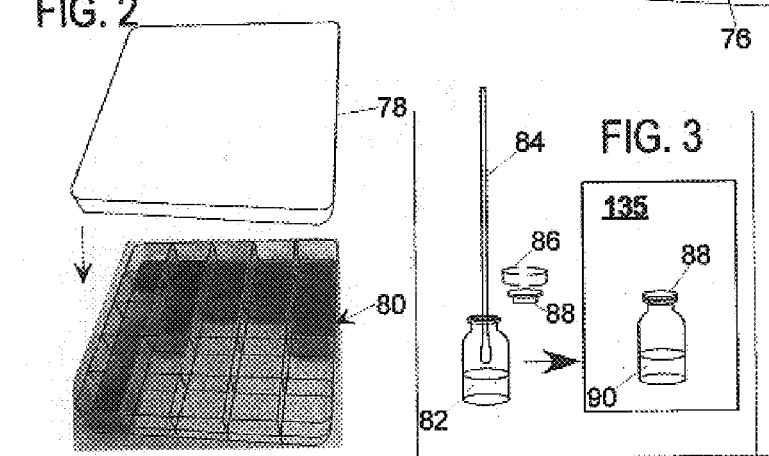
FIG. 3
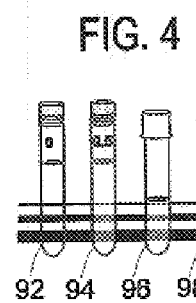
FIG. 4
FIG. 5
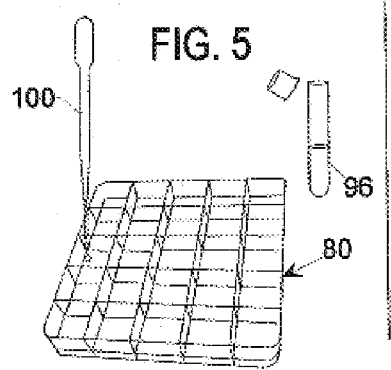
FIG. 6
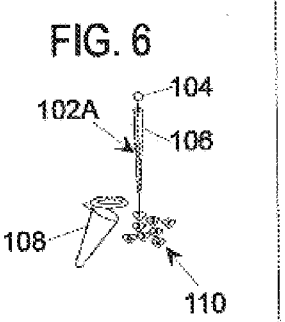

FIG. 7
Prior Art
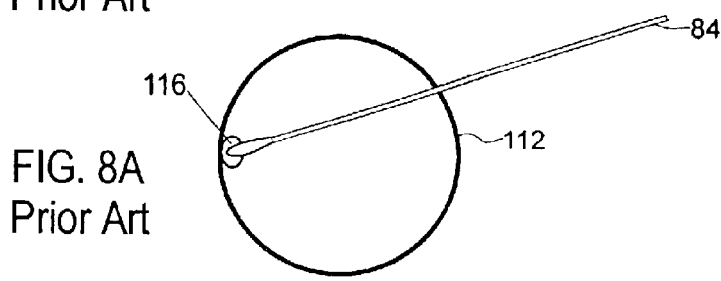
FIG. 8A
Prior Art
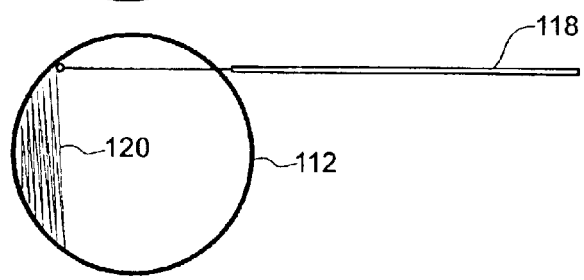
FIG. 8B
Prior Art
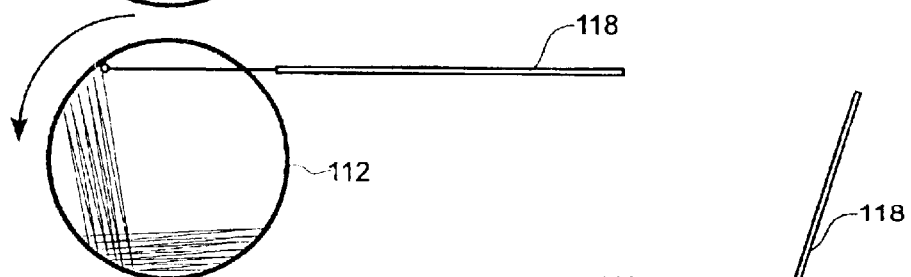
FIG. 8C
Prior Art
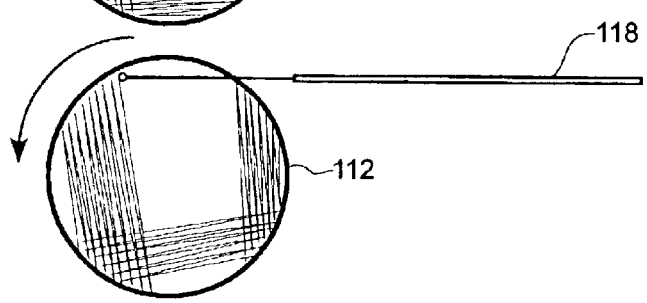
FIG. 8D
Prior Art
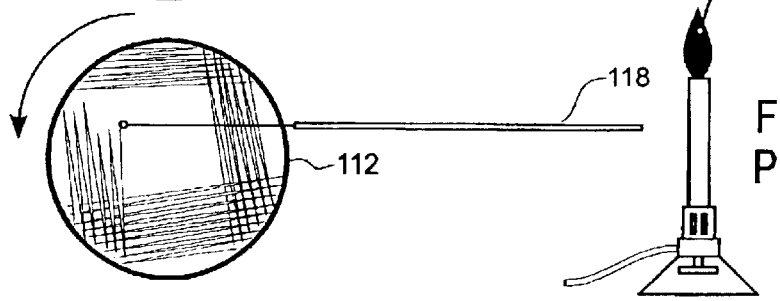
FIG. 8E
Prior Art
FIG. 9
Prior Art

FIG.10 Prior Art

| TABLE OF COLONY CHARACTERISTICS |  |
|---|---|
| ELEVATIONS: FLAT, RAISED, PULVINATE, CONVEX, UMBONATE, UMBILICATE  MARGINS: ENTIRE, UNDULATE, CURLED, FILAMENTOUS | |
| FORM:<br>OVERALL SHAPE OF COLONY WHEN VIEWED FROM TOP | CIRCULAR - MOSTLY ROUND, MAY BE SLIGHTLY UNEVEN<br>WRINKLED UNEVEN SURFACE TEXTURE, OFTEN DRY IN APPEARANCE<br>IRREGULAR - EDGES VERY UNEVEN<br>RHIZOIDAL - BRANCHED (UNCOMMON)<br>FILAMENTOUS - POWDERY, SPREADING LINES (FUNGI)<br>CURLED - SEPARATED EDGES, CONCENTRIC CIRCLES (UNCOMMON) |
| ELEVATION:<br>VIEW COLONY FROM SIDE | FLAT - WHEN LIGHT IS REFLECTED ACROSS SURFACE OF COLONY, NO CONVEX SHAPE IS SEEN (COMMON)<br>RAISED - ELEVATED (COMMON)<br>CONVEX - SLIGHT DOME SHAPE (COMMON)<br>PULVINATE - HAT-LIKE APPEARANCE -DOMED IN MIDDLE, SLIGHTLY RAISED AT EDGES (MOST SIGNIFICANT IN 1-2 DAY CULTURE |
| MARGIN:<br>VIEW EDGE OF COLONY | ENTIRE - SMOOTHLY CURVING EDGE (COMMON)<br>UNDULATE - WAVY EDGE (COMMON)<br>LOBATE - VERY IRREGULAR AMOEBA-LIKE EDGES (UNCOMMON)<br>FILAMENTOUS - POWDERY LINES (FUNGI)<br>CURLED - SEPARATE EDGES (UNCOMMON) |
| CONSISTENCY:<br>TEXTURE OF COLONY WHEN LOOP IS INSERTED INTO IT | BUTYROUS - BUTTER-LIKE, CAN PICK US PASTE EASILY<br>MUCOID - SLIMY (<3MM OF SLIME THAT ATTACHES TO END OF LOOP WHEN SAMPLING) (COMMON)<br>VISCID- STICKY, RESISTANT TO PICK UP OF PASTE, SOME ELASTICITY OF COLONY HAS BEEN LOST (UNCOMMON)<br>WAXLIKE - COLONY FRAGMENTS WHEN BEING PICKED UP (UNCOMMON)<br>POWDERY - LIGHT FILAMENTS (FOUND MOSTLY IN MOLDS) |
| PIGMENT (COLOR) | OFF-WHITE - ANY VARIATION ON WHITE, INCLUDING GREY, TAN, CREAM, IVORY VERY PALE YELLOW<br>WHITE - PORCELAIN WHITE ONLY (UNCOMMON) |
| APPEARANCE (REFLECTED LIGHT) | TEXTURE AS YOU TILT PLATE AND VIEW AT AN ANGLE FROM THE TOP UNDER A BRIGHT LIGHT |
| APPEARANCE (TRANSMITTED LIGHT) VIEW WHILE HOLDING UP TO BRIGHT LIGHT AND LOOK THROUGH COLONIES. | TRANSPARENT - COMPLETELY SEE-THROUGH, COLONIES HARD TO SEE (UNCOMMON).<br>TRANSLUCENT - CAN SEE MODEST REDUCTION OF LIGHT PASSING THROUGH COLONY (COMMON)<br>OPAQUE - ALMOST NO LIGHT PASSES THROUGH COLONY (COMMON) |
| DIAMETER OF COLONY | COLONIES NEED TO BE WELL SEPARATED. FUNCTION OF TIME |

FIG. 11
Prior Art

TABLE OF CELLULAR MORPHOLOGY BY LIGHT MICROSCOPE OBSERVATION (400X-600X).
MOTILITY WILL BE OBSERVED WITH SOME OF THESE.

| Spherical cells (COCCI) | Rod-shaped cells (BACILLI) | Spiral-shaped cells (SPIRILLA) |
|---|---|---|
| Streptococci | Coccobacilli (short rods) | Borrelia-type spirillum |
| Staphylococci | Coryneform bacilli (club shaped rods) | Treponema-type spirillum |
| Diplococci | Vibrio (comma shaped rods) | Leptospira-type spirillum |

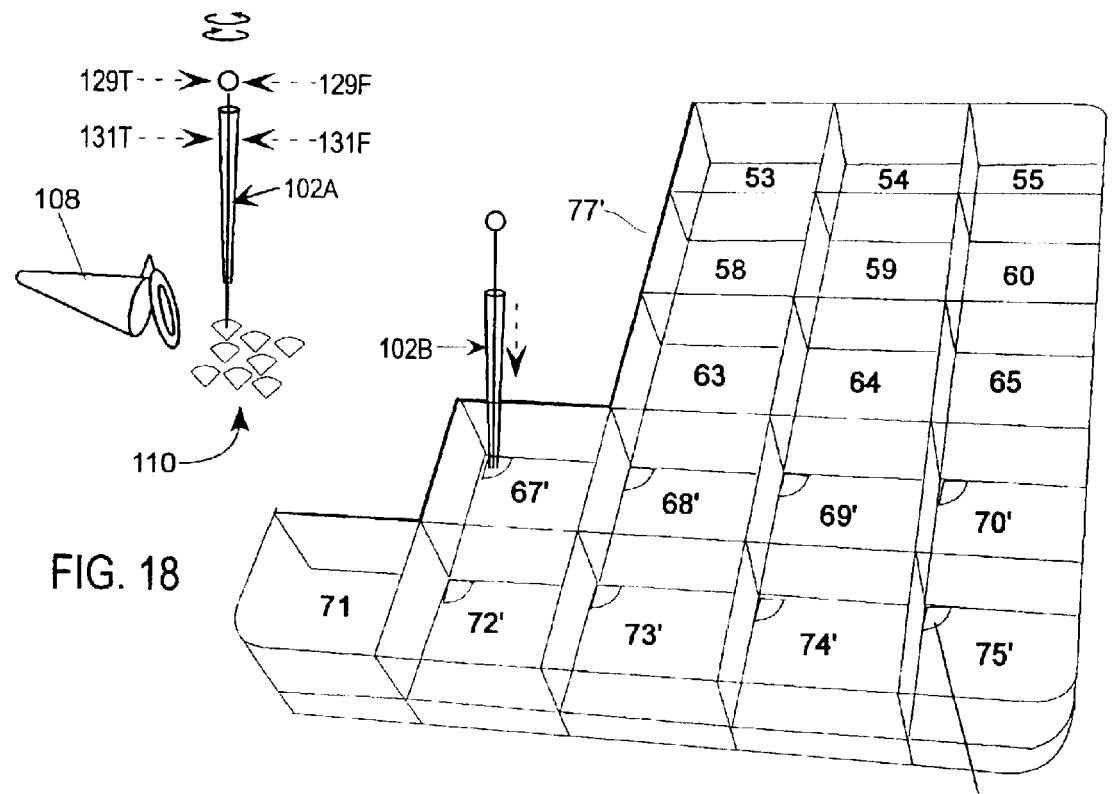
FIG. 18
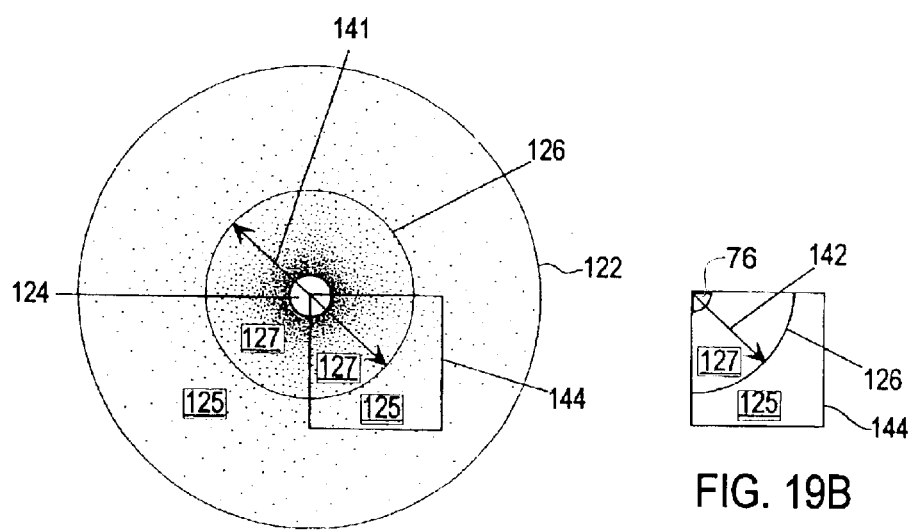
FIG. 19A
FIG. 19B

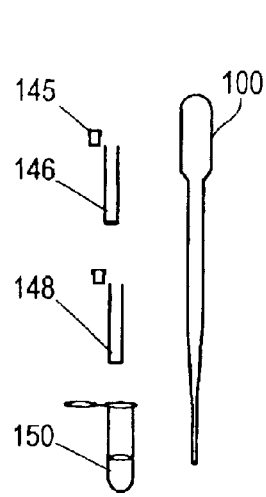
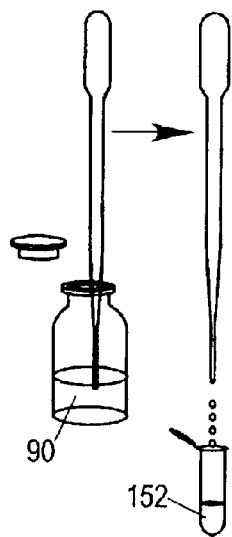
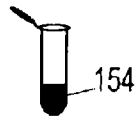
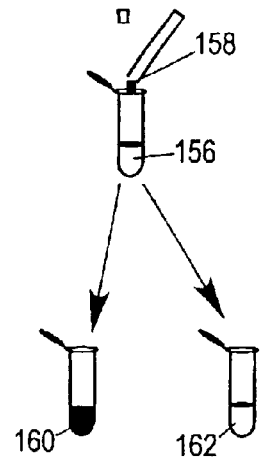
FIG. 20A　　FIG. 20B　　FIG. 20C　　FIG. 20D
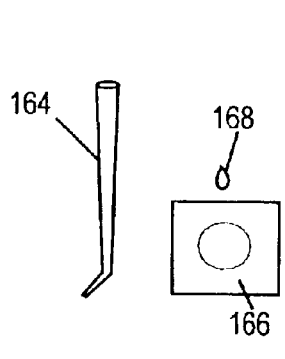
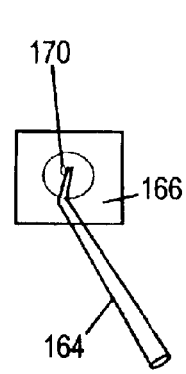
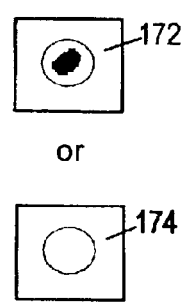
FIG. 21A　　FIG. 21B　　FIG. 21C

FIG. 22

| | TABLE OF CULTURE PLATE MEDIA AND THEIR PURPOSES | |
|---|---|---|
| 51 | | Used for isolating a wide variety of microorganisms. Contains 5% sheep red blood cells. Will grow all non-fastidious gram negative and gram positive organisms. |
| 56 | | Used for isolating, differentiating and presumptively identifying group D streptococcus and Enterococcus These organisms cause the formation of a dark brown or black complex in the agar. |
| 61 | Mannitol salt agar | Staphylococci will grow in this medium while the growth of most other bacteria will be inhibited. |
| 66 | | This medium permits the isolation of coagulase positive staphylococcus. Coagulase negative staph. and other bacteria are completely inhibited. Coagulase positive staph. reduce tellurite and produce black colonies. |
| 71 | | Used for isolation of fungi. Suitable for growth of pathogenic fungi. Incubate for several days. Molds and yeasts form non-spreading, discrete colonies. |
| 52 | | Used in the isolation of gram positive organisms from clinical and non-clinical specimens. Azide suppresses the growth of gram negative bacteria. Useful in determining hemolytic reactions. |
| 62 | | Gram negative organisms that are able to metabolize citrate will grow luxuriantly. The medium is alkalinized and changes from its initial green to deep blue. |
| 63 | Pseudomonas agar F | Used for differentiating Pseudomonas aeruginosa from other pseudomonads based on fluorescein production. Visible with UV lamp at 365nm. |
| 64 | Pseudomonas agar P | Used for differentiating Pseudomonas aeruginosa from other pseudomonads based on the production of pyocyanin, a non-fluorescent blue pigment. |
| 60 | | Used to isolate and differentiate Salmonella. Colonies are greenish blue, with black centers |
| 65 | | MacConkey agar with an added substrate(MUG) that becomes fluorescent when E.coli is present. The E.coli's beta-glucuronidase enzyme cleaves the colorless MUG to fluorescent product that is detected with UV light 365nm |
| 53 | | MacConkey agar with lactose. Selective and differential medium for growing gram negative bacilli. Lactose fermenting strains grow as red or pink colonies. |
| 54 | | MacConkey agar with glucose. Selective and differential medium for growing gram negative bacilli. Glucose fermenting strains grow as red or pink colonies. |
| 55 | | MacConkey agar with mannitol. Selective and differential medium for growing gram negative bacilli. Mannitol fermenting strains grow as red or pink colonies. |
| 57 | | MacConkey agar with inositol. Selective and differential medium for growing gram negative bacilli. Inositol fermenting strains grow as red or pink colonies. |
| 58 | | MacConkey agar with Sucrose. Selective and differential medium for growing gram negative bacilli. Sucrose fermenting strains grow as red or pink colonies. |
| 59 | | MacConkey agar with arabinose. Selective and differential medium for growing gram negative bacilli. Arabinose fermenting strains grow as red- pink colonies. |
| 67-70 72-75 | | Considered to be the best media for routine susceptibility testing of non-fastidious bacteria. Eight chambers are set aside for this purpose. |

FIG. 23

TABLE OF PREFERRED EMBODIMENT OF CULTURE PLATE MEDIA

| 51 | 52 | 53 | 54 | 55 |
|---|---|---|---|---|
| 56 | 57 | 58 | 59 | 60 |
| 61 | 62 | 63 | 64 | 65 |
| 66 | 67 | 68 | 69 | 70 |
| 71 | 72 | 73 | 74 | 75 |

Fig. 24A

| TABLE FOR IDENTIFICATION OF NON-FASTIDIOUS GRAM NEGATIVE BACTERIA USING KIT RESULTS PAGE 1 OF 3 ||||||||||||
|---|---|---|---|---|---|---|---|---|---|---|---|
| IDENTIFICATION CRITERIA: | CIT | ARA | GLU | INO | LAC | MAN | SUC | OXI | NO2 | MOT | MAC |
| | | | | | | | | | | | |
| OBSERVE EACH CHAMBER OF PLATE REFERRING TO THE "TABLE OF CULTURE PLATE MEDIA AND THEIR PURPOSES". WHEN THE ORGANISM IS GRAM NEGATIVE (I.E. GROWTH ON MAC AND/OR OXIDASE POSTIVE) A LIST OF IDENTIFICATION CRITERIA CAN BE ASSEMBLED: CIT=UTILIZES CITRATE? ARA=FERMENTS ARABINOSE?; GLU=FERMENTS GLUCOSE?; INO=FERMENTS INOSITOL?; LAC=FERMENTS LACTOSE?; MAN=FERMENTS MANNITOL?; SUC=FERMENTS SUCROSE?; MAC=GROWS ON ANY MAC MEDIA; SEE ACCESSORY RESULTS FOR OXI=OXIDASE ACTIVITY, NO2=NITRATE REDUCTASE ACTIVITY,AND MOT=IS BACTERIA MOTILE? LET 1 = YES AND 0 = NO. FILL IN BOXES ACCORDINGLY AND THEN SEARCH DATABASE BELOW FOR BEST MATCH (MANUALLY OR USING DATABASE FILTER SOFTWARE) ||||||||||||

| GRAM NEGATIVE ORGANISM | INCUBATION | CIT | ARA | GLU | INO | LAC | MAN | SUC | OXI | NO2 | MOT | MAC |
|---|---|---|---|---|---|---|---|---|---|---|---|---|
| GRAM NEGATIVE ORGANISM | INCUBATION | CIT | ARA | GLU | INO | LAC | MAN | SUC | OXI | NO2 | MOT | MAC |
| Cedecea davisae | 12-20h | 0 | 0 | 1 | 0 | 0 | 1 | 1 | 0 | 1 | 1 | 1 |
| Cedecea lapagei | 12-20h | 1 | 0 | 1 | 0 | 0 | 1 | 0 | 0 | 1 | 1 | 1 |
| Cedecea neteri | 12-20h | 1 | 0 | 1 | 0 | 0 | 1 | 1 | 0 | 1 | 1 | 1 |
| Cedecea sp. 3 | 12-20h | 1 | 0 | 1 | 0 | 0 | 1 | 1 | 0 | 1 | 1 | 1 |
| Cedecea sp.5 | 12-20h | 0 | 0 | 1 | 0 | 0 | 1 | 1 | 0 | 1 | 1 | 1 |
| Citrobacter amalonaticus | 12-20h | 1 | 1 | 1 | 0 | 1 | 1 | 0 | 0 | 1 | 1 | 1 |
| Citrobacter diversus | 12-20h | 1 | 1 | 1 | 0 | 1 | 1 | 0 | 0 | 1 | 1 | 1 |
| Citrobacter freundii | 12-20h | 1 | 1 | 1 | 0 | 1 | 1 | 1 | 0 | 1 | 1 | 1 |
| Edwardsiella tarda | 12-20h | 0 | 0 | 1 | 0 | 0 | 0 | 0 | 0 | 1 | 1 | 1 |
| Enterobacter aerogenes | 12-20h | 1 | 1 | 1 | 1 | 1 | 1 | 1 | 0 | 1 | 1 | 1 |
| Enterobacter agglomerans | 12-20h | 1 | 1 | 1 | 0 | 1 | 1 | 1 | 0 | 1 | 1 | 1 |
| Enterobacter amnigenus 1 | 12-20h | 1 | 1 | 1 | 0 | 1 | 1 | 1 | 0 | 1 | 1 | 1 |
| Enterobacter amnigenus 2 | 12-20h | 1 | 1 | 1 | 0 | 1 | 1 | 0 | 0 | 1 | 1 | 1 |
| Enterobacter cloacae | 12-20h | 1 | 1 | 1 | 0 | 1 | 1 | 1 | 0 | 1 | 1 | 1 |
| Enterobacter gergoviae | 12-20h | 1 | 1 | 1 | 0 | 1 | 1 | 1 | 0 | 1 | 1 | 1 |
| Enterobacter intermedium | 12-20h | 1 | 1 | 1 | 0 | 1 | 1 | 0 | 0 | 1 | 1 | 1 |
| Enterobacter sakazakii | 12-20h | 1 | 1 | 1 | 1 | 1 | 1 | 1 | 0 | 1 | 1 | 1 |
| Enterobacter taylorae | 12-20h | 1 | 1 | 1 | 0 | 1 | 1 | 0 | 0 | 1 | 1 | 1 |
| Escherichia coli | 12-20h | 0 | 1 | 1 | 0 | 1 | 1 | 0 | 0 | 1 | 1 | 1 |
| Escherichia fergusonii | 12-20h | 0 | 1 | 1 | 0 | 1 | 1 | 0 | 0 | 1 | 1 | 1 |
| Escherichia hermannii | 12-20h | 0 | 1 | 1 | 0 | 1 | 1 | 1 | 0 | 1 | 1 | 1 |
| Escherichia vulneris | 12-20h | 0 | 1 | 1 | 0 | 1 | 1 | 0 | 0 | 1 | 1 | 1 |
| Ewingella americana | 12-20h | 0 | 0 | 1 | 0 | 0 | 1 | 0 | 0 | 1 | 1 | 1 |
| Hafnia alvei | 12-20h | 0 | 1 | 1 | 0 | 0 | 1 | 0 | 0 | 1 | 1 | 1 |
| Klebsiella oxytoca | 12-20h | 1 | 1 | 1 | 1 | 1 | 1 | 1 | 0 | 1 | 0 | 1 |
| Klebsiella ozaenae | 12-20h | 0 | 1 | 1 | 1 | 1 | 1 | 0 | 0 | 1 | 0 | 1 |
| Klebsiella pneumoniae | 12-20h | 1 | 1 | 1 | 1 | 1 | 1 | 1 | 0 | 1 | 0 | 1 |
| Klebsiella Rhinoscleromatis | 12-20h | 0 | 0 | 1 | 1 | 1 | 1 | 0 | 0 | 1 | 0 | 1 |
| Kluyvera sp. | 12-20h | 1 | 1 | 1 | 0 | 0 | 1 | 1 | 0 | 1 | 1 | 1 |
| Moellerella wisconsensis | 12-20h | 0 | 0 | 1 | 0 | 0 | 0 | 1 | 0 | 1 | 0 | 1 |
| Morganella morganii | 12-20h | 0 | 0 | 1 | 0 | 0 | 0 | 0 | 0 | 1 | 1 | 1 |
| Presumptive Yersinia pestis | 12-20h | 0 | 0 | 1 | 0 | 0 | 1 | 0 | 0 | 1 | 0 | 1 |
| Proteus mirabilis | 12-20h | 1 | 0 | 1 | 0 | 0 | 0 | 0 | 0 | 1 | 1 | 1 |

Fig. 24B

| TABLE FOR IDENTIFICATION OF NON-FASTIDIOUS GRAM NEGATIVE BACTERIA USING KIT RESULTS PAGE 2 OF 3 |||||||||||||
|---|---|---|---|---|---|---|---|---|---|---|---|---|
| GRAM NEGATIVE ORGANISM | INCUBATION | CIT | ARA | GLU | INO | LAC | MAN | SUC | OXI | NO2 | MOT | MAC |
| Proteus penneri | 12-20h | 0 | 0 | 1 | 0 | 0 | 0 | 1 | 0 | 1 | 1 | 1 |
| Proteus vulgaris | 12-20h | 0 | 0 | 1 | 0 | 0 | 0 | 1 | 0 | 1 | 1 | 1 |
| Providencia alcalifaciens | 12-20h | 1 | 0 | 1 | 0 | 0 | 0 | 0 | 0 | 1 | 1 | 1 |
| Providencia rettgeri | 12-20h | 1 | 0 | 1 | 1 | 0 | 1 | 0 | 0 | 1 | 1 | 1 |
| Providencia stuartii Ure- | 12-20h | 1 | 0 | 1 | 1 | 0 | 0 | 0 | 0 | 1 | 1 | 1 |
| Providencia stuartii Ure+ | 12-20h | 1 | 0 | 1 | 1 | 0 | 0 | 1 | 0 | 1 | 1 | 1 |
| Salmonella cholerae suis | 12-20h | 0 | 0 | 1 | 0 | 0 | 1 | 0 | 0 | 1 | 1 | 1 |
| Salmonella enteritidis | 12-20h | 1 | 1 | 1 | 0 | 0 | 1 | 0 | 0 | 1 | 1 | 1 |
| Salmonella paratyphi A | 12-20h | 0 | 1 | 1 | 0 | 0 | 1 | 0 | 0 | 1 | 1 | 1 |
| Salmonella subgroup 3 | 12-20h | 1 | 1 | 1 | 0 | 0 | 1 | 0 | 0 | 1 | 1 | 1 |
| Salmonella typhi | 12-20h | 0 | 0 | 1 | 0 | 0 | 1 | 0 | 0 | 1 | 1 | 1 |
| Salmonella typhimurium | 12-20h | 1 | 1 | 1 | 0 | 0 | 1 | 0 | 0 | 1 | 1 | 1 |
| Serratia fonticola | 12-20h | 0 | 1 | 1 | 1 | 1 | 1 | 0 | 0 | 1 | 1 | 1 |
| Serratia odorifera 1 | 12-20h | 1 | 1 | 1 | 1 | 1 | 1 | 1 | 0 | 1 | 1 | 1 |
| Serratia odorifera 2 | 12-20h | 1 | 1 | 1 | 1 | 1 | 1 | 0 | 0 | 1 | 1 | 1 |
| Serratia plymuthica | 12-20h | 0 | 1 | 1 | 1 | 1 | 1 | 1 | 0 | 1 | 1 | 1 |
| Serratia rubidaea | 12-20h | 1 | 1 | 1 | 0 | 1 | 1 | 1 | 0 | 1 | 1 | 1 |
| Serratia liquefaciens | 12-20h | 1 | 1 | 1 | 1 | 1 | 1 | 1 | 0 | 1 | 1 | 1 |
| Serratia marcescens | 12-20h | 1 | 0 | 1 | 1 | 1 | 1 | 1 | 0 | 1 | 1 | 1 |
| Tatumella ptyseos | 12-20h | 0 | 0 | 1 | 0 | 0 | 0 | 1 | 0 | 1 | 0 | 1 |
| Yersinia enteroclitica | 12-20h | 0 | 1 | 1 | 0 | 0 | 1 | 1 | 0 | 1 | 0 | 1 |
| Yersinia frederiksenii /intermedia | 12-20h | 0 | 1 | 1 | 0 | 0 | 1 | 1 | 0 | 1 | 0 | 1 |
| Yersinia kristensenii | 12-20h | 0 | 1 | 1 | 1 | 0 | 1 | 0 | 0 | 1 | 0 | 1 |
| Yersinia pseudotuberculosis | 12-20h | 0 | 0 | 1 | 0 | 0 | 1 | 0 | 0 | 1 | 0 | 1 |
| Yersinia ruckeri (AN) | 12-20h | 0 | 0 | 1 | 0 | 0 | 1 | 0 | 0 | 1 | 0 | 1 |
| Achromobacter spp. (Vd) | 24h | 0 | 0 | 0 | 0 | 0 | 0 | 0 | 1 | 1 | 1 | 1 |
| Achromobacter spp. (Vd) | 48h | 1 | 0 | 0 | 0 | 0 | 0 | 0 | 1 | 1 | 1 | 1 |
| Achromobacter xylosoxidans | 24h | 0 | 0 | 0 | 0 | 0 | 0 | 0 | 1 | 1 | 1 | 1 |
| Achromobacter xylosoxidans | 48h | 1 | 0 | 0 | 0 | 0 | 0 | 0 | 1 | 1 | 1 | 1 |
| Acinetobacter calcoaceticsv.lwoffi | 24h | 0 | 0 | 0 | 0 | 0 | 0 | 0 | 0 | 0 | 0 | 1 |
| Acinetobacter calcoaceticsv.lwoffi | 48h | 0 | 0 | 0 | 0 | 0 | 0 | 0 | 0 | 0 | 0 | 1 |
| Acinetobacter calcoaceticus v.anitratus | 24h | 0 | 1 | 1 | 0 | 0 | 0 | 0 | 0 | 0 | 0 | 1 |
| Acinetobacter calcoaceticus v.anitratus | 48h | 1 | 1 | 1 | 0 | 0 | 0 | 0 | 0 | 0 | 0 | 1 |
| Aeromonas hydrophila group | 24h | 0 | 1 | 1 | 0 | 0 | 1 | 1 | 1 | 1 | 1 | 1 |
| Aeromonas salmonicida (25c) | 24h | 0 | 0 | 1 | 0 | 0 | 1 | 0 | 1 | 1 | 0 | 1 |
| Agrobacterium radiobacter | 24h | 0 | 0 | 0 | 0 | 0 | 0 | 0 | 1 | 0 | 1 | 1 |
| Agrobacterium radiobacter | 48h | 1 | 0 | 0 | 0 | 0 | 0 | 0 | 1 | 0 | 1 | 1 |
| Alcaligenes spp. | 24h | 0 | 0 | 0 | 0 | 0 | 0 | 0 | 1 | 0 | 1 | 1 |
| Alcaligenes spp. | 48h | 1 | 0 | 0 | 0 | 0 | 0 | 0 | 1 | 0 | 1 | 1 |
| Bordetella bronchiseptica | 24h | 0 | 0 | 0 | 0 | 0 | 0 | 0 | 1 | 1 | 1 | 1 |
| Bordetella bronchiseptica | 48h | 1 | 0 | 0 | 0 | 0 | 0 | 0 | 1 | 1 | 1 | 1 |
| CDC Group II J | 24h | 0 | 0 | 0 | 0 | 0 | 0 | 0 | 1 | 0 | 0 | 0 |
| CDC Group II J | 48h | 0 | 0 | 0 | 0 | 0 | 0 | 0 | 1 | 0 | 0 | 0 |
| CDC Group IV C-2 | 24h | 0 | 0 | 0 | 0 | 0 | 0 | 0 | 1 | 0 | 1 | 1 |
| CDC Group IV C-2 | 48h | 1 | 0 | 0 | 0 | 0 | 0 | 0 | 1 | 0 | 1 | 1 |
| CDC Group IV E | 24h | 0 | 0 | 0 | 0 | 0 | 0 | 0 | 1 | 1 | 0 | 1 |
| CDC Group IV E | 48h | 0 | 0 | 0 | 0 | 0 | 0 | 0 | 1 | 1 | 0 | 1 |
| CDC Group V E-1 | 24h | 1 | 1 | 1 | 0 | 0 | 0 | 0 | 0 | 0 | 1 | 1 |
| CDC Group V E-1 | 48h | 1 | 1 | 1 | 0 | 0 | 0 | 0 | 0 | 1 | 1 | 1 |

Fig. 24C

| TABLE FOR IDENTIFICATION OF NON-FASTIDIOUS GRAM NEGATIVE BACTERIA USING KIT RESULTS PAGE 3 OF 3 | | | | | | | | | | | |
|---|---|---|---|---|---|---|---|---|---|---|---|
| GRAM NEGATIVE ORGANISM | INCUBATION | CIT | ARA | GLU | INO | LAC | MAN | SUC | OXI | NO2 | MOT | MAC |
| CDC Group V E-2 | 24h | 1 | 1 | 1 | 0 | 0 | 0 | 0 | 0 | 0 | 1 | 1 |
| CDC Group V E-2 | 48h | 1 | 1 | 1 | 0 | 0 | 0 | 0 | 0 | 0 | 1 | 1 |
| CDS Group II F | 24h | 0 | 0 | 0 | 0 | 0 | 0 | 0 | 1 | 0 | 0 | 0 |
| CDS Group II F | 48h | 1 | 0 | 0 | 0 | 0 | 0 | 0 | 1 | 0 | 0 | 0 |
| Chromobacterium | 24h | 1 | 0 | 1 | 0 | 0 | 0 | 0 | 1 | 1 | 1 | 1 |
| Chromobacterium | 48h | 1 | 0 | 1 | 0 | 0 | 0 | 0 | 1 | 1 | 1 | 1 |
| Eikenella corrodens | 24h | 0 | 0 | 0 | 0 | 0 | 0 | 0 | 1 | 0 | 0 | 0 |
| Eikenella corrodens | 48h | 0 | 0 | 0 | 0 | 0 | 0 | 0 | 1 | 0 | 0 | 0 |
| Flavobactierum breve | 24h | 0 | 0 | 0 | 0 | 0 | 0 | 0 | 1 | 0 | 0 | 1 |
| Flavobactierum breve | 48h | 1 | 0 | 0 | 0 | 0 | 0 | 0 | 1 | 0 | 0 | 1 |
| Flavobactierum meningosepticum | 24h | 0 | 0 | 0 | 0 | 0 | 0 | 0 | 1 | 0 | 0 | 1 |
| Flavobactierum meningosepticum | 48h | 1 | 0 | 0 | 0 | 0 | 0 | 0 | 1 | 0 | 0 | 1 |
| Flavobactierum Multivorum | 24h | 0 | 0 | 1 | 0 | 0 | 0 | 0 | 1 | 0 | 0 | 1 |
| Flavobactierum Multivorum | 48h | 1 | 0 | 1 | 0 | 0 | 0 | 1 | 1 | 0 | 0 | 1 |
| Flavobactierum odoratum | 24h | 0 | 0 | 0 | 0 | 0 | 0 | 0 | 1 | 0 | 0 | 1 |
| Flavobactierum odoratum | 48h | 1 | 0 | 0 | 0 | 0 | 0 | 0 | 1 | 0 | 0 | 1 |
| Flavobactierum spiritivorum | 24h | 0 | 0 | 0 | 0 | 0 | 0 | 0 | 1 | 0 | 0 | 0 |
| Flavobactierum spiritivorum | 48h | 0 | 0 | 0 | 0 | 0 | 0 | 0 | 1 | 0 | 0 | 0 |
| Flavobactierum spp. (IIB) | 24h | 0 | 0 | 0 | 0 | 0 | 0 | 0 | 1 | 0 | 0 | 1 |
| Flavobactierum spp. (IIB) | 48h | 1 | 0 | 0 | 0 | 0 | 0 | 0 | 1 | 0 | 0 | 1 |
| Moraxella spp. | 24h | 0 | 0 | 0 | 0 | 0 | 0 | 0 | 1 | 1 | 0 | 0 |
| Moraxella spp. | 48h | 0 | 0 | 0 | 0 | 0 | 0 | 0 | 1 | 1 | 0 | 0 |
| Other Psudomonas spp. | 24h | 0 | 0 | 0 | 0 | 0 | 0 | 0 | 1 | 1 | 1 | 1 |
| Other Psudomonas spp. | 48h | 1 | 0 | 0 | 0 | 0 | 0 | 0 | 1 | 1 | 1 | 1 |
| Pasteurella aerogenes | 24h | 0 | 1 | 1 | 1 | 0 | 0 | 1 | 1 | 1 | 0 | 1 |
| Pasteurella aerogenes | 48h | 0 | 1 | 1 | 1 | 0 | 0 | 1 | 1 | 1 | 0 | 1 |
| Pasteurella multocida | 24h | 0 | | | | | | | 1 | 1 | 0 | 0 |
| Pasteurella multocida | 48h | 0 | | | | | | | 1 | 1 | 0 | 0 |
| Pasteurella-Actinobaccilus spp. | 24h | 0 | 0 | 0 | 0 | 0 | 0 | 0 | 1 | 1 | 0 | 0 |
| Pasteurella-Actinobaccilus spp. | 48h | 0 | 0 | 0 | 0 | 0 | 0 | 0 | 1 | 1 | 0 | 0 |
| Plesiomonas shigelloides | 24h | 0 | 0 | 1 | 1 | 0 | 0 | 0 | 1 | 1 | 1 | 1 |
| Pseudomonas cepacia | 24h | 1 | 0 | 1 | 0 | 0 | 0 | 0 | 1 | 0 | 1 | 1 |
| Pseudomonas cepacia | 48h | 1 | 0 | 1 | 0 | 0 | 0 | 0 | 1 | 0 | 1 | 1 |
| Pseudomonas fluorescens | 24h | 0 | 0 | 0 | 0 | 0 | 0 | 0 | 1 | 1 | 1 | 1 |
| Pseudomonas fluorescens | 48h | 1 | 0 | 0 | 0 | 0 | 0 | 0 | 1 | 1 | 1 | 1 |
| Pseudomonas maltophilia | 24h | 1 | 0 | 0 | 0 | 0 | 0 | 0 | 0 | 0 | 1 | 1 |
| Pseudomonas maltophilia | 48h | 1 | 0 | 0 | 0 | 0 | 0 | 0 | 0 | 0 | 1 | 1 |
| Pseudomonas Paucimobilis | 24h | 0 | 0 | 0 | 0 | 0 | 0 | 0 | 1 | 0 | 0 | 0 |
| Pseudomonas Paucimobilis | 48h | 1 | 0 | 0 | 0 | 0 | 0 | 0 | 1 | 0 | 0 | 0 |
| Pseudomonas putida | 24h | 1 | 0 | 0 | 0 | 0 | 0 | 0 | 1 | 0 | 1 | 1 |
| Pseudomonas putida | 48h | 1 | 0 | 0 | 0 | 0 | 0 | 0 | 1 | 0 | 1 | 1 |
| Pseudomonas putrefaciens | 24h | 1 | 0 | 0 | 0 | 0 | 0 | 0 | 1 | 1 | 1 | 1 |
| Pseudomonas putrefaciens | 48h | 1 | 0 | 0 | 0 | 0 | 0 | 0 | 1 | 1 | 1 | 1 |
| Pseudomonas Stutzeri | 24h | 0 | 0 | 0 | 0 | 0 | 0 | 0 | 1 | 1 | 1 | 1 |
| Pseudomonas Stutzeri | 48h | 1 | 0 | 0 | 0 | 0 | 0 | 0 | 1 | 1 | 1 | 1 |
| Pseudomonas aeruginosa | 24h | 1 | 0 | 1 | 0 | 0 | 0 | 0 | 1 | 1 | 1 | 1 |
| Pseudomonas aeruginosa | 48h | 1 | 0 | 1 | 0 | 0 | 0 | 0 | 1 | 1 | 1 | 1 |
| Pseudomonas pseudomallei | 24h | 0 | 1 | 0 | 1 | 0 | 1 | 1 | 1 | 1 | 1 | 1 |
| Pseudomonas pseudomallei | 48h | 0 | 0 | 1 | 1 | 0 | 1 | 1 | 1 | 1 | 1 | 1 |

Table: Syneresis with (1) Control, (2) 0.2% Iota Carrageenan or
(3) 0.2% Iota Carrageenan Plus 1mM Calcium, Added to Four different
Agar-based Media: Blood, Chocolate, MacConkey and Azide Blood.

|  | BA1 | BA2 | BA3 | CHO1 | CHO2 | CHO3 | MAC1 | MAC2 | MAC3 | ABA1 | ABA2 | ABA3 |
|---|---|---|---|---|---|---|---|---|---|---|---|---|
| 28 day, | 0.070 | 0.035 | 0.025 | 0.066 | 0.049 | 0.029 | 0.079 | 0.042 | 0.040 | 0.081 | 0.029 | 0.020 |
| grams | 0.079 | 0.028 | 0.022 | 0.055 | 0.039 | 0.016 | 0.075 | 0.048 | 0.047 | 0.068 | 0.023 | 0.017 |
| water | 0.080 | 0.021 | 0.029 | 0.060 | 0.027 | 0.010 | 0.084 | 0.039 | 0.042 | 0.065 | 0.030 | 0.016 |
| of syneresis | 0.084 | 0.029 | 0.016 | 0.057 | 0.035 | 0.011 | 0.090 | 0.043 | 0.039 | 0.071 | 0.031 | 0.015 |

Above values multiplied by 1000, to express results in milligrams below:

|  | BA,1 | BA,2 | BA,3 | CHO,1 | CHO,2 | CHO,3 | MAC,1 | MAC,2 | MAC,3 | ABA,1 | ABA,2 | ABA,3 |
|---|---|---|---|---|---|---|---|---|---|---|---|---|
| 28 day, | 70 | 35 | 25 | 66 | 49 | 29 | 79 | 42 | 40 | 81 | 29 | 20 |
| milligrams | 79 | 28 | 22 | 55 | 39 | 16 | 75 | 48 | 47 | 68 | 23 | 17 |
| water | 80 | 21 | 29 | 60 | 27 | 10 | 84 | 39 | 42 | 65 | 30 | 16 |
| of syneresis | 84 | 29 | 16 | 57 | 35 | 11 | 90 | 43 | 39 | 71 | 31 | 15 |

T Statistics

|  | BA,1 | BA,2 | BA,3 | CHO,1 | CHO,2 | CHO,3 | MAC,1 | MAC,2 | MAC,3 | ABA,1 | ABA,2 | ABA,3 |
|---|---|---|---|---|---|---|---|---|---|---|---|---|
| mean (n=4) | 78 | 28 | 23 | 60 | 38 | 17 | 82 | 43 | 42 | 71 | 28 | 17 |
| standard dev. | 6 | 6 | 5 | 5 | 9 | 9 | 6 | 4 | 4 | 7 | 4 | 2 |
| p-value | 1.0000 | <.0001 | <.0001 | 1.0000 | 0.0053 | 0.0001 | 1.0000 | <.0001 | <.0001 | 1.0000 | <.0001 | <.0001 | p-values are relative to zero controls("1's") using pooled variances

Statistics performed using WebStat 3.0 and without removal of any outliers

Figure 40A

Table: The Effect of Iota Carrageenan, Without Added Calcium, on Syneresis of Mueller-Hinton Agar

| | Final concentration of Iota Carrageenan (%w/v) added to Mueller-Hinton agar | | | | | | |
|---|---|---|---|---|---|---|---|
| | 0% | 0.1% | 0.2% | 0.4% | 0.6% | 0.8% | 1.0% |
| 29 day, | 0.051 | 0.023 | 0.013 | 0.019 | 0.028 | 0.030 | 0.008 |
| grams | 0.052 | 0.023 | 0.022 | 0.015 | 0.025 | 0.015 | 0.006 |
| water | 0.062 | 0.022 | 0.015 | 0.014 | 0.030 | 0.035 | 0.004 |
| of syneresis | 0.051 | 0.030 | 0.025 | 0.020 | 0.020 | 0.024 | 0.006 |

Above values multiplied by 1000, to express results in milligrams:

| | Final concentration of Iota Carrageenan (%w/v) added to Mueller-Hinton agar | | | | | | |
|---|---|---|---|---|---|---|---|
| | 0% | 0.1% | 0.2% | 0.4% | 0.6% | 0.8% | 1.0% |
| 29 day, | 51 | 23 | 13 | 19 | 28 | 30 | 8 |
| milligrams | 52 | 23 | 22 | 15 | 25 | 15 | 6 |
| water | 62 | 22 | 15 | 14 | 30 | 35 | 4 |
| of syneresis | 51 | 30 | 25 | 20 | 20 | 24 | 6 |

T Statistics

| | 0% | 0.1% | 0.2% | 0.4% | 0.6% | 0.8% | 1.0% |
|---|---|---|---|---|---|---|---|
| mean (n=4) | 54.0 | 24.5 | 18.8 | 17.0 | 25.8 | 26.0 | 6.0 |
| standard dev. | 5.4 | 3.7 | 5.7 | 2.9 | 4.3 | 8.6 | 1.6 |
| p-value | 1.0000 | 0.0001 | 0.0001 | <.0001 | 0.0002 | 0.0015 | <.0001 | p-values are relative to zero controls using pooled variances

Figure 41A

Table: The Effect of Iota Carrageenan, With 1mM Added Calcium, on Syneresis of Mueller-Hinton Agar

| | Final concentration of Iota Carrageenan (%w/v) added to Mueller-Hinton agar | | | | | | |
|---|---|---|---|---|---|---|---|
| | 0% | 0.1% | 0.2% | 0.4% | 0.6% | 0.8% | 1.0% |
| 29 day, | 0.061 | 0.027 | 0.014 | 0.004 | 0.002 | 0.005 | 0.002 |
| grams | 0.054 | 0.021 | 0.031 | 0.010 | 0.004 | 0.004 | 0.003 |
| water | 0.050 | 0.017 | 0.025 | 0.008 | 0.002 | 0.007 | 0.007 |
| of syneresis | 0.054 | 0.028 | 0.020 | 0.006 | 0.003 | 0.006 | 0.004 |

Above values multiplied by 1000, to express results in milligrams:

| | Final concentration of Iota Carrageenan (%w/v) added to Mueller-Hinton agar | | | | | | |
|---|---|---|---|---|---|---|---|
| | 0% | 0.1% | 0.2% | 0.4% | 0.6% | 0.8% | 1.0% |
| 29 day, | 61 | 27 | 14 | 4 | 2 | 5 | 2 |
| milligrams | 54 | 21 | 31 | 10 | 4 | 4 | 3 |
| water | 50 | 17 | 25 | 8 | 2 | 7 | 7 |
| of syneresis | 54 | 28 | 20 | 6 | 3 | 6 | 4 |

T Statistics

| | 0% | 0.1% | 0.2% | 0.4% | 0.6% | 0.8% | 1.0% |
|---|---|---|---|---|---|---|---|
| mean (n=4) | 54.8 | 23.3 | 22.5 | 7.0 | 2.8 | 5.5 | 4.0 |
| standard dev. | 4.6 | 5.2 | 7.2 | 2.6 | 1.0 | 1.3 | 2.2 |
| p-value | 1.0000 | 0.0001 | 0.0001 | <.0001 | 0.0002 | 0.0015 | <.0001 | p-values are relative to zero controls using pooled variances

Figure 42A

TABLE I--INTERPRETATIVE STANDARDS TABLE

| Antimicrobial Agent | Color code | apply to BA/CHO | Zone radius match with value below for R, I or S |||
|---|---|---|---|---|---|
| | | | Resistant | Intermediate | Susceptible |
| Ampicillin(AM) | orange | either | ≤ 5.5 | 6-6.5 | ≥ 7 |
| | | | gram neg. enteric & enterococci |||
| | | | ≤ 10 | 5.5-14 | ≥ 14.5 |
| | | | staph & pen G susceptible organisms |||
| Amox./Clav.(AMC) | green | either | ≤ 6.5 | 7-8.5 | ≥ 9 |
| | | | gram neg. enteric & enterococci |||
| | | | ≤ 9.5 | - | ≥ 10 |
| | | | staph & pen G susceptible organisms |||
| Amikacin(AN) | brown | BA | ≤ 7 | 7.5-8 | ≥ 8.5 |
| Cephalothin(CF) | violet | either | ≤ 7 | 7.5-8.5 | ≥ 9 |
| Doxycycline(D) | yellow | BA | ≤ 6 | 6.5-7.5 | ≥ 8 |
| Enrofloxacin(ENO) | blue | either | ≤ 7.5 | 8-10 | ≥ 10.5 |
| Gentamicin(GM) | red | BA | ≤ 5 | 5.5-6.5 | ≥ 7 |
| Septra(TMP/SMX) | white | BA | ≤ 5 | 5.5-7.5 | ≥ 8 |
| Pipericillin(PIP) | green dot | either | ≤ 8.5 | 9-10 | ≥ 10.5 |
| | | | gram neg. enteric & enterococci |||
| | | | ≤ 8.5 | - | ≥ 9 |
| | | | Pseudomonas aeruginosa |||
| Ciprofloxicin(CIP) | black | either | ≤ 7.5 | 8-10 | ≥ 10.5 |
| Marbofloxacin(MAR) (Pfizer values) | blue dot | either | ≤ 6.5 | 7-8 | ≥ 8.5 |
| | | | (values suggested by manufacturer) |||

Figure 47

MICROBIAL CULTURE MEDIUM CONTAINING AGAR AND IOTA CARRAGEENAN

RELATED APPLICATIONS

This application claims the benefit and is a continuation-in part, of U.S. patent application Ser. No. 10/036,042, filed Nov. 9, 2001, now abandoned entitled "Method and Kit for Rapid Concurrent Identification and Antimicrobial Susceptibility Testing of Microorganisms from Broth Culture," which is incorporated herein by reference.

BACKGROUND OF THE INVENTION

1. Field of the Invention

The present invention relates to the identification and microbial susceptibility testing of an unknown microorganism or microorganisms. More specifically, the present invention relates to methods, apparatus, and media for use in the concurrent identification and susceptibility testing of a sample of a microorganism.

2. Description of Related Art

Throughout history, humanity has fallen victim to pandemics of cholera, plague, influenza, typhoid, tuberculosis and other infectious maladies so widespread that few people survived into what is now considered "middle age." As recently as the $19^{th}$ century, the average life span in Europe and North America was about 50 years. It was a world in which the likelihood of dying prematurely from infectious diseases was as high as 40%, and where women routinely succumbed to infections during childbirth which are now easily curable by today's standards. In underdeveloped nations, the situation was even worse. Unfortunately, however, unlike many industrialized nations, medical conditions in many underdeveloped nations have never really improved. Indeed, in poorer nations today, infectious diseases, both major and seemingly minor, still contribute to premature death and to the ongoing misery of underprivileged populations.

The emergence of multi-resistant, or "antibiotic-resistant" bacteria, has threatened the security of developed nations and further shaken the citizens of less-developed countries, and is now a worldwide concern. In many nations, antibiotics are used indiscriminately, further contributing to the rise of antibiotic resistance in a variety of bacteria, including species of *Enterococcus, Staphylococcus, Pseudomonas,* and the Enterobacteriaceae family. The emergence of antibiotic-resistant organisms is very often a result of the over-use of broad-spectrum antibiotics. There is also concern that inappropriate veterinary use of antibiotics may lead to development of antibiotic resistant bacteria. In some cases, these bacteria could then, in turn, infect humans.

The diagnosis of infectious diseases has traditionally relied upon various microbiological culture methods to identify the organism responsible for an infection and then to determine the appropriate antimicrobial treatment for the patient. These methods continue to be important for analysis, despite recent advances in molecular and immunological diagnostics. While the development of rapid and automated methods has served to increase the efficiency of microbiological analysis, traditional quantitative culture methods remain critical for definitive diagnosis of infections. See, Baron & Finegold, Diagnostic Microbiology, $8^{th}$ ed. C. V. Mosby, (1990), p. 253. Further, these traditional methods are even more valuable in countries unable to afford newer methods, such as automated identification and susceptibility-testing methods. In addition, many areas of the world are devoid of adequate clinical microbiology facilities capable of providing access to newer diagnostic methods. Indeed, in some cases, even traditional culture-based methods are only narrowly available.

Traditional culture-based diagnostic methods share a general set of method steps. A first group of these steps involves the collection and transport of a specimen. The specimen must be material from the actual infection site. Once collected, it is necessary to maintain the sample as near to its original state as possible with minimum deterioration. Transport systems often consist of a protective container, transport medium and a culture swab, as illustrated in FIG. 7. A problem with the use of a holding or transport medium is that it may jeopardize the recovery of certain strains. A major task is to reduce the time delay between collection of specimens and inoculation onto microbiological culture media. The transport container is constructed to minimize hazards to specimen handlers. It is best to minimize adverse environmental conditions, such as rapid changes in pressure, exposure to extremes of heat and cold or excessive drying. The transport of fluid specimens to the laboratory must be done as quickly as possible. It is recommended that a 2-hour maximum time limit be imposed between collection and delivery of specimens to the laboratory. This limit poses a problem for specimens collected any distance from a clinical microbiology laboratory.

In addition to the above difficulties, under some conditions, traditional microbiological culture media suffer from several weaknesses. First, satisfactory microbiological culture media must generally contain many components to successfully support bacterial life. More specifically, satisfactory media must include available sources of water, vitamins, inorganic phosphate and sulfur, trace metals, carbon and nitrogen. These needs may be supplied from a number of sources. In addition, various media may include agents which selectively allow the growth of specific organisms while preventing the growth of others. Media may often include compounds that enhance the ability of a user to identify the bacteria growing thereon. The following is a list of common media constituents with their sources in parenthesis: (1) Amino-nitrogen (peptone, protein hydrolysate, infusions and extracts), (2) Growth factors (blood, serum, yeast extract or vitamins, NAD), (3) Energy sources (sugar, alcohols, and carbohydrates), (4) Buffer salts (Phosphates, acetates and citrates), (5) Mineral salts and metals (phosphate, sulfate, magnesium, calcium, iron), (6) Selective agents (chemicals, antimicrobials and dyes), (7) Indicator dyes (phenol red, neutral red), and (8) Solidifying agents (agar, gelatin, alginate, silica gel, etc.).

Culture media is commonly available in both liquid and solid forms. Solid media provides for the isolation of microorganisms contained in a mixture of different microorganisms. Liquid media, often referred to as "broth", can provide a nutritionally rich environment which is more accessible to individual cells than solid media. This allows the microorganisms to grow rapidly but does not isolate them from each other. Brain Heart Infusion Broth is one such rich liquid media supplying many of the compounds that the cell would otherwise have to synthesize. This allows the cell to devote more of its energy to growth, which is another reason for their faster growth in liquid media.

A selection of the appropriate solid culture media for microbiological test(s) is generally made according to the particular specimen type. Several hundred standard culture media are commercially available. Various culture media have been developed to serve specific purposes, including the identification of bacteria and antibiotic susceptibility testing. One medium used in antibiotic susceptibility testing is Mueller Hinton agar. The media used as identification testing media can generally be divided into five groups: enriched media, differential media, selective media, differential-selective media, and single purpose media. Enriched media have special additives to support pathogens having fastidious growth needs. Examples of enriched media include sheep blood agar and brain heart infusion broth. Differential media allows the differentiation of groups of microorganisms based on color changes of an indicator (sensitive to a property such as pH) in the culture medium that take place as a result of biochemical reactions associated with microorganism growth. Separating organisms that ferment the sugar lactose, for example, from those that do not, is one example of the utility of differential media.

Selective media support the growth of certain microorganisms of interest while suppressing the growth of others. Azide blood agar is an example. Gram-positive organisms grow on this media whereas gram-negative organisms do not. Differential-selective media combine the characteristics of both selective media and differential media, thus allowing the selective growth and rapid differentiation of major groups of bacteria. These media are widely used in tests for gram-negative bacilli (rods). MacConkey and Hektoen media are examples. Single-purpose media isolate one specific type of microorganism. Bile esculin azide agar is an example of this media. *Enterococcus* and group D *streptococcus* grow and cause the formation of a dark brown or black complex in the agar.

In modern microbiology laboratories, every attempt is made to use well-trained personnel, working under close supervision, in the processing of specimens. Errors or misjudgments made during laboratory processing, such as improper choice of culture media, can negate all the expertise one may apply in later processing steps such as the reading and interpretation of cultures. Expert microbiologists may often be caught short in making definitive diagnoses because of the selection and use of inadequate or incorrect media in culturing a specimen.

The equipment required for the primary inoculation of specimens includes several microbiological agar-based media plates and a nichrome or platinum inoculating wire or loop (see FIGS. 8B–8E). Plates currently used in the field generally have a shelf life of from one to two months. Specimens are "streaked out" on the surface of the plates to spread the microorganisms across the surface of the culture medium. This results in isolated colonies. As illustrated in FIGS. 8A–8E the first step in "streaking" is to touch and roll the tip of the swab 84 containing the specimen 116 on the surface of the medium (FIG. 8A). Then, using an inoculating loop 118 that has been flamed to sterilize it (FIG. 9), streak the primary inoculum 116 by spreading it out in the first quadrant (FIG. 8B). Re-sterilize the loop 118 and cool. Streak the inoculum from the first quadrant into the second quadrant (FIG. 8C). Repeat the process for the other two quadrants (FIG. 8D–8E). Incubate the plate following the placement of a lid for 18 to 24 hours. The preceding method is the standard prior art method for isolating microorganisms where at each new streaking they become further diluted until they finally become isolated from one another.

As the isolated microorganisms grow on the solid medium, they form a mass called a colony. This mass of cells originated from a single cell and now may consist of hundreds of thousands of cells. These colonies have distinct characteristics that are a clue in the process of identifying the microorganism (see FIG. 10). The sub-culturing of the isolated colonies to additional media produces pure cultures. The microscopic examination of a suspension of bacteria from a colony reveals (a) cellular morphology, (b) cellular arrangement, and (c) motility. These features (See FIG. 11) add additional pieces to the ID puzzle. A gram stain of the sample may also assist the analyst in getting closer to a characterization of the organism. The gram stain is not foolproof however, and can be occasionally misleading because the staining is frequently dependent upon the age of the colony.

The testing of certain enzyme systems unique to each species provides further clues to the ID of an unknown organism. Another basis for ID is the culture requirements, which include the atmospheric needs of the organism, as well as nutritional requirements and ability to grow on different kinds of media. A further basis of ID in regards to the biochemical characteristics includes the mode of carbohydrate utilization, catalase reactions of gram-positive bacteria and oxidase reactions of gram-negative bacteria. ID to the species level is based on a set of physiological and biochemical characteristics including the degradation of carbohydrates, amino acids, and a variety of other substrates.

Commercial kits perform a number of various biochemical reactions. The results of these reactions can reveal unique patterns for ID. Some systems are automated and others are manual. A problem with manual systems is the limited scope in terms of the organisms they target for ID. Additionally it is necessary to first isolate the organism of interest from other microorganisms in an 18 to 24 hour isolation step as described above before applying the organism to the manual or automated ID system. For example, the manufacturer bioMerieux Vitek® markets the following manual systems (listing the target organisms): API 20C AUX (yeasts), API 20E (Enterobacteriaceae and non-fermenting gram-negative bacteria), API 30 Strep. (*Streptococcus* and *Enterococcus*), API Coryne (Corynebacteria and coryne-like-organisms), API 20 NE (Gram-negative non-Enterobacteriaceae), API Rapid 20E (Enterobacteriaceae), and API Staph (*Staphylococcus* and *micrococcus*). Judgment must be made by the microbiologist as to which isolate to test and the proper ID system to use. This is another source of possible error.

Current microbial testing methods call for initial isolation and identification of the organism first and then, if deemed appropriate, i.e. where a pathogen is identified, performing an antimicrobial susceptibility test. In addition, the analyst must decide which microorganism is responsible for the clinical disease in mixed cultures. There are a number of different ways of doing antimicrobial susceptibility testing (AST). Two of them are disk-diffusion and micro dilution.

In recent years, there has been a trend toward the use of commercial broth micro dilution and automated instrument methods instead of the disk-diffusion procedure. However, there may be renewed interest in the disk-diffusion test because of its inherent flexibility in drug selection and low cost. The availability of numerous antimicrobial agents and the diversity in antibiotic formularies in different institutions has made it difficult for manufactures of commercial test systems to provide standard test panels that fit every facility's needs. Thus, the inherent flexibility of drug selection provided by the disk-diffusion test is an undeniable asset of the method. It is also one of the most established and best proven of all AST tests and continues to be updated and refined through frequent National Committee for Clinical Laboratory Standards (NCCLS) publications. Furthermore, clinicians readily understand the qualitative interpretive category results of susceptible, intermediate, and resistant provided by the disk test. It is an ideal method when doing manual diagnostic microbiology The initial isolation step results in colonies formed from a single microorganism. The analyst then transfers like colonies into growth broth. The broth is incubated at 35° C. for 2 to 8 hours until growth reaches the turbidity at or above that of a McFarland 0.5 standard 94. This turbidity is equivalent to $1.5 \times 10^8$ colony forming units (CFU)/ml. McFarland standards are prepared using different amounts of barium sulfate in water. This salt is insoluble in water and forms a very fine suspension when shook. Within 15 minutes of adjusting turbidity, a cotton swab 85 transfers this inoculum to a Standard Susceptibility Dish 122. The entire surface of the Mueller-Hinton plate is swabbed three times; rotating the plate approximately 60 degrees between streaking to ensure even distribution (FIG. 12A). The plate stands for 3 to 15 minutes before AST disk 124 is applied. Apply to the agar surface with a dispenser or manually with sterile forceps. Apply gentle pressure to ensure complete contact of the disk with the agar. (FIG. 12B showing one disk added). Incubate for 16 to 18 hours at 35° C. in an ambient-air incubator.

FIG. 12C illustrates the basic principle of the disk-diffusion method of AST. As soon as the antibiotic-impregnated AST disk 124 is exposed to the moist agar surface, water is absorbed into the filter paper and the antibiotic 128 diffuses into the surrounding medium. The rate of extraction of the antibiotic out of the disk is greater than its outward diffusion into the medium, so that the concentration immediately adjacent to the disk may exceed that in the disk itself. As the distance from the disk increases, however, there is a logarithmic reduction in the antibiotic concentration. If the plate has been previously inoculated with a bacterial suspension, simultaneous growth of bacteria occurs on the surface of the agar. When a critical cell mass of bacteria is reached, the inhibitory activity of the antibiotic is overcome and microbial growth occurs. The time (critical time) required to reach the critical cell mass (4 to 10 hours for commonly tested bacteria) is characteristic of each species but is influenced by the composition of the medium and temperature of incubation. The depth of the agar will affect the lateral extent of antimicrobial diffusion before the critical time is reached because diffusion occurs in three dimensions.

The points at which the critical cell mass is reached appears as a sharply marginated circle (margin 126), of microorganism growth 125, with the middle of the disk forming the center of the circle if the test has been performed properly (see FIG. 12D). The concentration of diffused antibiotic at this margin 126 of growing and non-growing bacteria 127 is known as the critical concentration. This concentration approximates the minimal inhibitory concentration (MIC) obtained in dilution tests. The Minimal inhibitory concentration (MIC) is the lowest concentration of a chemotherapeutic agent that will prevent growth of the test microorganisms. The disk-diffusion test that has become standard in the United States is based on the work of Bauer, Kirby and coworkers. The zone size observed in a disk-diffusion test has no meaning in and of itself. The interpretative standards provided by the NCCLS show the correlation between zone sizes and MICs of those species tested by disk-diffusion method.

FIG. 13 shows a poorly prepared AST plate with objectionable overlapping of the zones of growth inhibition from adjacent disks. FIG. 14 shows a poorly streaked AST plate with uneven growth. The zone margins are indistinct, compromising accurate measurement.

A distinct disadvantage of the above prior art is the total time that it takes from obtaining the culture through performing ID and AST. At least three days transpire before results are available. Another disadvantage is the expense to process the specimen using prior art. A further disadvantage of the prior art is the number of steps involved in performing the tests, which increases the likelihood of human error.

A further disadvantage is raised by the limited shelf life of the agar-based microbiology media that is currently used in the art. Specifically, most currently-available agar-based media have a shelf life of from about one to about two months at most. One problem which reduces the shelf life of such media is syneresis, a condition in which the liquid component of the agar media separates from the gel component. This dramatically reduces the utility of the media by segregating the moisture and nutrients needed in all portions of the agar in a liquid phase, rendering the agar uneven in its ability to support sample growth. This restricts the ability of facilities to maintain an inventory of suitable media and complicates the manufacture, distribution, and sale of diagnostic kits utilizing agar-based media currently known and used in the art.

SUMMARY OF THE INVENTION

The compounds, methods, and apparatus of the present invention have been developed in response to the present state of the art, and in particular, in response to the problems and needs in the art that have not yet been fully solved by currently available methods, apparatus, and media for use in the concurrent identification and susceptibility testing of microorganisms.

This invention thus relates to methods, apparatus, and media for use in the concurrent identification and antimicrobial susceptibility testing of an unknown microorganism or microorganisms. More specifically, the invention provides specialized media, bacterial identification and antibiotic-susceptibility testing kits constructed using the specialized media, and methods for their use in providing diagnosis of and recommended treatment regimens for infections. The media, kits, and methods of the invention may allow manual determination of the type of infection present in a specimen in periods of about 24 hours. The invention further provides stabilized culture media useful in a broad variety of applications.

The present method, kit, and media of the invention relate in part to the identification (or "ID") of microorganisms as well as to the concurrent or consecutive determination of antimicrobial susceptibilities (antibiotic susceptibility testing or "AST"). The methods of the invention may allow testing directly from an initial broth culture without requiring an isolation step. The method and kit offer quick characterization of microorganisms, in some situations as quickly as one-third of the time required in standard manual methods.

The culture media of the invention may be used in the above kits as well as in many other applications. The agar-based media are fonnulated using carrageenan to extend the useful shelf life of the media, as well as the useful shelf life of kits using the media of the invention. The carrageenan-infused culture media of the invention result in a reduction of syneresis, thus providing potential improved performance of the media. The kits of the invention produced with the carrageenan-stabilized culture media may have a shelf life of from about 3 to about 12 months. In some embodiments, the kits may have a shelf life of at least about 5 months from date of manufacture when stored at 4° C.

The kits of the invention may employ a disposable multi-chambered plate (kit plate) with carrageenan-formulated media including: enriched, differential, selective, and differential-selective media in addition to AST medium. Broth medium may be provided with the kit for increasing the volume of microorganisms present in a sample in preparation for eventual dilution and inoculation onto the kit plate. AST disk-quarters may be included in the kit, as may biochemical reagents for additional testing.

The invention thus comprises specialized media, methods, and kits for in-house or in-the-field characterization and/or antibiotic susceptibility testing of unknown microorganisms. The kit may be provided such that it comes complete with all components and equipment needed to perform the testing except for an incubator and a simple microscope. A portable incubator can be operated from any direct current source such as an automobile battery. As a result, the kit is well suited in areas where microbiology laboratories are scarce or unavailable. In addition, the kit serves to obtain rapid AST information. Microorganisms such as Anthrax (Bacillus anthracis) can be determined concurrently with drug susceptibility testing within 24 hours.

Use of the media, methods, and kits of the invention may improve the situation throughout our world in regards to rising resistance to antibiotics. As discussed above, many antibiotics are no longer effective against certain strains of bacteria. AST is useful and important for the common microorganism species that are not predictably susceptible to drugs of choice because of acquired resistance mechanisms (e.g., members of the Enterobacteriaceae, the *Pseudomnonas* species, *Staphylococcus* species, *Enterococcus* species, *Streptococcus pneumoniae, Haemophilus influenzae,* and *Neisseria gonorrhoeae*). A recent editorial in the British Journal of Medicine states: "Research is also a cornerstone in the fight against bacterial resistance. We have to improve our understanding of microorganism flora, the evolution of resistance, and the mechanisms of transmissibility of resistant bacteria. New diagnostic technologies to enable rapid ID of viral and bacterial infections are also necessary: for too long it has been easier for clinicians to prescribe an antibiotic than to make a specific diagnosis". P. Huovinen & O. Cars, *BMJ* 317:613–614 (1998). The media, method, and kit accomplish the rapid ID of microorganism infections needed for making a specific diagnosis. The results of antimicrobial susceptibilities complete the picture, and allow use of proper treatments.

The media, methods, and kits of the invention may provide a method and kit where an ideal specimen from the site of infection or a microorganism-containing sample can be immediately applied to broth culture media. This may render the use of transport media unnecessary. Therefore, the specimen is not subjected to time delays; possible adverse environmental conditions or excessive drying that would compromise its integrity. Fluid specimens can also be immediately processed. In addition, a more rapid result is realized with this system due to immediate inoculation of the specimen to broth culture. The microorganism sample is ready for dilution and inoculation onto the multi-chambered kit plate within 4 to 8 hours following broth culture incubation.

The invention may further provide a method and kit comprising a multi-chambered, easily visualized culture kit plate comprising a battery of different media with diagnostic functionality. The miniaturization of the media is very cost effective. The multi-kit plate media performs the ID and AST of gram-negative and gram-positive organisms. In some embodiments, one chamber may be devoted to fungal determination. Errors or misjudgments in the prior art of media selection may be avoided with the present system. An appropriate selection of medium is already incorporated in the design of the multi-chambered kit plate. This may assure that the user of the kit will not be caught short in making a definitive diagnosis due to incorrect media selection.

The invention may additionally provide a more basic kit and method using a multi-chambered culture plate using a more limited range of media configured to provide presumptive identification to a genus level while allowing antimicrobial susceptibility testing.

A special dilution method utilized with the kits of the invention simplifies the inoculation of the microorganism sample to the various media of the kit plates. Time is very often of the essence with an infection. The prior art of streaking each diagnostic plate for isolation of the organisms becomes unnecessary. The present kits may utilize a liquid dilution to a standard equivalent from a starting broth culture. A further dilution added to the kit may result in individual colonies in the various media test chambers. A magnifying lens such as a microscope 10× objective turned backwards may be included to provide a good view of the morphology and chemistry of the microorganism's colony on the various media. This makes the prior art isolation step unnecessary. Isolation and ID may thus take place together in the same chamber at the same time. The method of the invention is very reproducible and the faster growing organisms such as members of the Enterobacteriaceae family can produce discernable colonies within 12 to 18 hours.

Thus the invention provides methods, and kits for determination of unlike microorganisms, such as gram-negative as well as gram-positive, at the same time. Thus, it may become unnecessary to use different manual ID systems as described in the prior art. This may save money as well as time. Another advantage is that errors in judgment may be avoided with regards to the selection of the appropriate kit or kits, for analysis. This prior art selection process would follow an initial isolation step (streaking, incubating and assessing) on a microbiological plate.

The invention may further provide a method and kit for concurrent ID and AST. The Kirby-Bauer disk-diffusion method used with this kit allows for flexibility in terms of choice of antimicrobial agents. The method of placing the antibiotics into the AST test chambers is quick, using a novel method. The resultant zone size is measured as radius whereas in a prior art standard method, zone size is measured as diameter which is exactly twice the value of the miniature assay. This allows the use of the NCCLS interpretative standards charts divided by 2. A third advantage is that the test chambers containing the AST media are well covered with a uniform inoculum of bacteria and produce a lawn of microorganism growth unlike the larger dishes that are prone to unevenness. In addition, since each antimicrobial is in its own chamber, there is no overlapping of the zones of growth inhibition from adjacent disks. A forth-important advantage is manifest when there is more than one organism on the kit plate. When more than one zone is evident, morphology of the more resistant organism (inner zone) can be observed by taking a sample of inner zone bacteria and observing microscopically. It has been observed that routine cultures that grow three or more organism types should be discounted. Specimens obtained from non-sterile sites most commonly represent colonization or contamination.

The invention may additionally provide a kit and method for ID and AST that can yield results in as little as one-third the time of the prior art methods. This method and kit can accomplish both rapid, straightforward ID and AST of an unknown microorganism or microorganisms from a single sample, where a prior isolation step is not required. Therefore, the patient can start on the correct antibiotic by the next day and avoid having to take an incorrect empirical antibiotic for a 3-day period, as would be the case in the prior art. Where the infection is life threatening, it is a powerful approach to the problem.

The invention further provides a kit and method for ID and AST where the kit plate component has a shelf life of from about 3 months to about 12 months, or in some specific embodiments at least 5 months when stored at 4° C. As noted above, the invention provides media incorporating carrageenan which exhibit enhanced shelf-stability, and thus an expanded shelf life. In some embodiments, the media of the invention incorporate up to about 0.5% iota carrageenan. In other embodiments, the agar-based media of the invention include up to about 0. 1% to about 1.0% iota carrageenan. In still other embodiments of the invention, the media of the invention include up to about 0.2% iota carrageenan.

Further objects and advantages of the media and kits f the invention will become apparent from a consideration of the drawings and ensuing description.

These and other features and advantages of the present invention will become more fully apparent from the following description and appended claims, or may be learned by the practice of the invention as set forth hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 shows a perspective view of a multi-chambered kit plate of the invention with square test chambers. Eight of the test chambers show antimicrobial disk-quarters in the corners of the test chambers;

FIG. 2 shows a kit plate and lid of the invention with various selective, differential and non-selective agar-based solid carrageenan-stabilized media. In addition, the lower right eight test chambers contain Mueller Hinton agar;

FIG. 3 shows a method of inoculation of Brain Heart infusion broth from a specimen and subsequent incubation called the initial broth culture;

FIG. 4 shows three McFarland turbidity standards with a dilution of the incubated broth;

FIG. 5 shows a method of applying a 0.5 McFarland equivalent dilution of incubated microorganisms to the bottom three rows of the kit plate;

FIG. 6 shows a device used to apply the antimicrobial disk-quarters to the susceptibility test chambers and a depiction of a set of antimicrobial disk-quarters;

FIG. 7 shows a typical culture transport system;

FIGS. 8A to 8E show the prior art steps for the addition of a microorganism sample to a standard solid media plate and subsequent streaking process which dilutes out the microorganism;

FIG. 9 shows a Bunsen burner;

FIG. 10 shows a table of various microorganism colony characteristics from the prior art;

FIG. 11 shows a table of various microorganism cell morphologies as observed with light microscope from the prior art;

FIG. 18 shows a method of applying antimicrobial diskquarters to the corners of the Mueller Hinton test chambers using the placement device;

FIGS. 19A and 19B show the principle of the standard Kirby-Bauer disk-diffusion test and illustrates how the system of the invention measures exactly one-half of the measurement of the prior art standard method;

FIGS. 20A to 20D show a method for determining nitrate reductase activity as part of the kit;

FIGS. 21A to 21C show a method for determining cytochrome oxidase activity as part of the kit, FIG. 22 shows a table of media components of this embodiment of the multi-chambered kit plate of the invention and associated reference numerals;

FIG. 23 shows a table of a kit plate media layout of the invention with the associated reference numerals;

FIGS. 24A to 24C show a table for identifying non-fastidious gram-negative bacteria using kit results;

FIG. 41A includes a table entitled "The Effect of Iota Carrageenan, Without Added Calcium on Syneresis of Mueller-Hinton agar";

FIG. 42A includes a table entitled "The Effect of Iota Carrageenan on Syneresis of Mueller-Hinton agar with 1 mM Calcium Added;"

FIG. 47 contains a table comprising data explaining how to determine susceptibility of a bacterium to a specific antibiotic.

DETAILED DESCRIPTION OF THE INVENTION

Figure 12A:
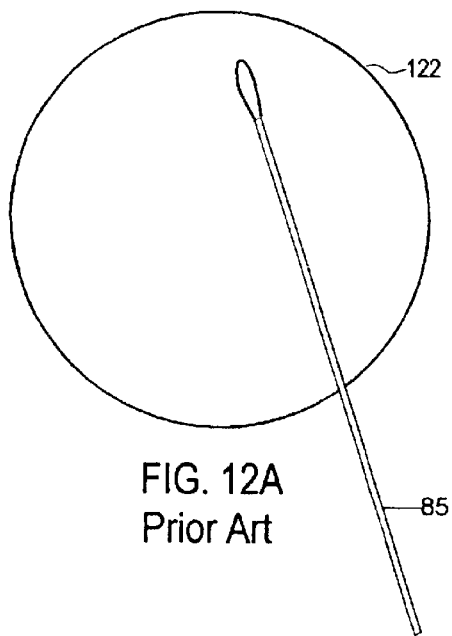
FIGS. 12A to 12D show the method and principle of the prior art AST Kirby-Bauer disk-diffusion test.
Figure 12B:
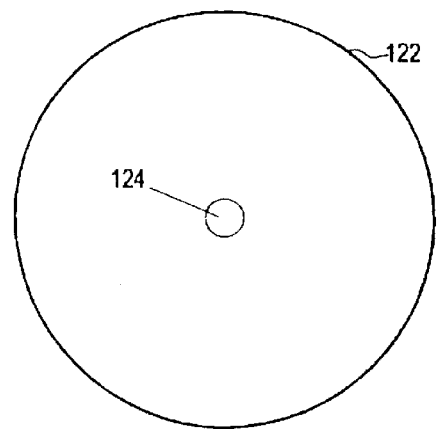
Figure 12C:
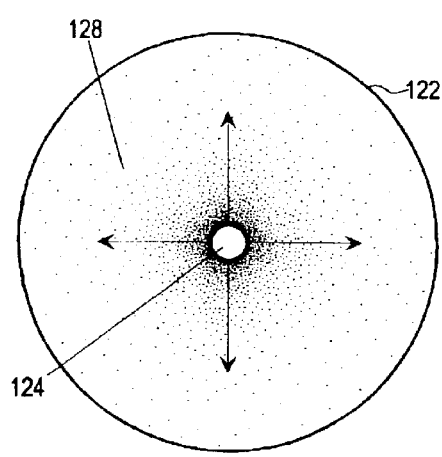
Figure 12D:
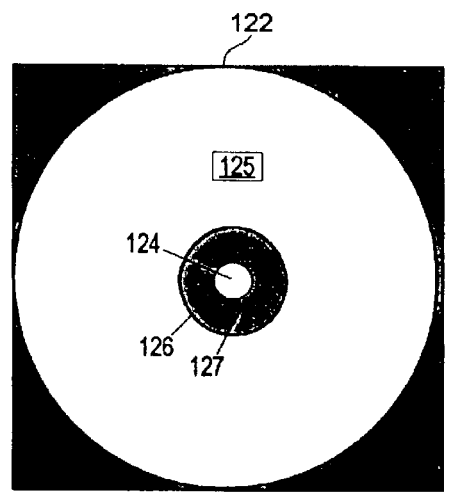
Figure 13:
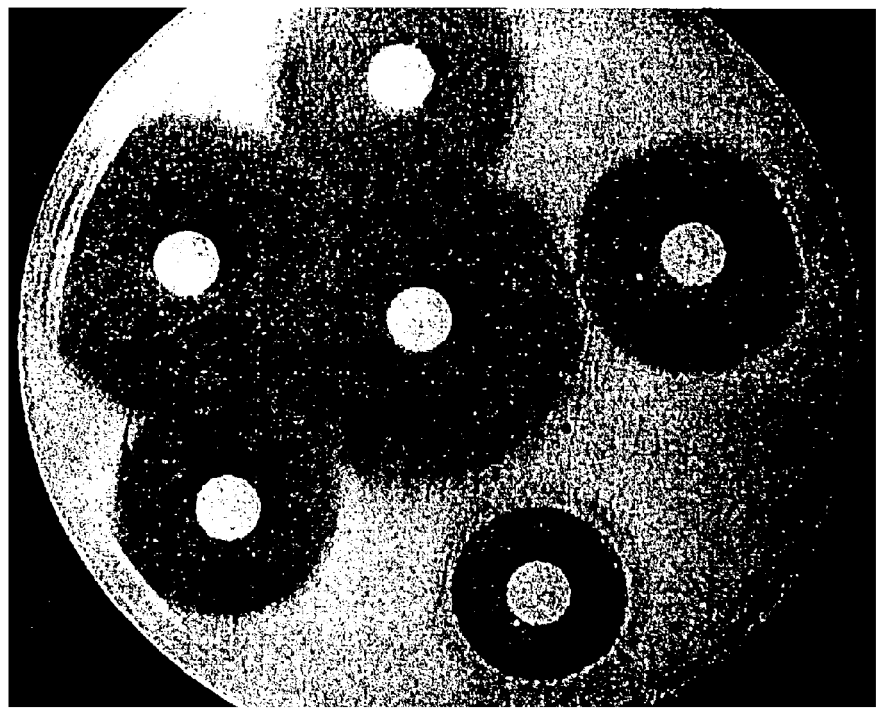
FIG. 13 shows a poorly prepared Kirby-Bauer disk diffusion test with overlapping zones from prior art.
Figure 14:
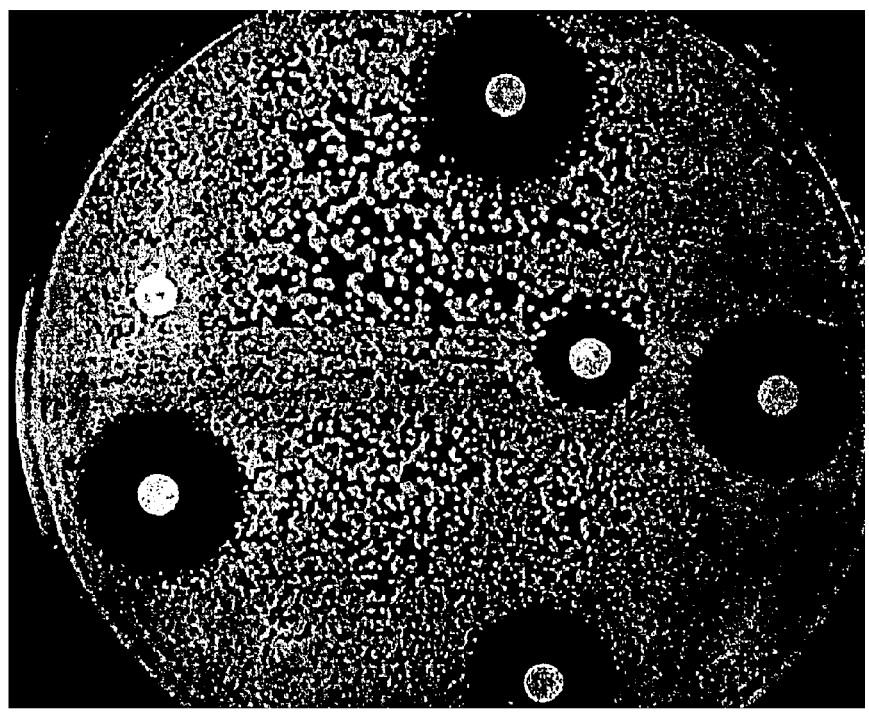
FIG. 14 shows a poorly prepared AST test with under applied bacteria from prior art.

The present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 47, is not intended to limit the scope of the invention, as claimed, but is merely representative of presently preferred embodiments of the invention.

The following section lists the static physical structure and components of a kit within the scope of the invention. An overview of the principal components of the kit is illustrated in FIG. 1. FIG. 1 shows a perspective view of an embodiment of a portion of the present invention, an ethylene oxide sterilized polypropylene multi-chambered kit plate 77 with square test chambers. Eight of the test chambers (67'–70' and 72'–75') are shown to include antimicrobial disk-quarters 76 in the corners of the test chambers. Quartering Standard Kirby-Bauer AST disks using a plastic jig and a razor blade is one way of preparing the disk-quarters. Labeling the disk-quarters may be done by hand. Media in the test chambers may be placed to a depth of 4 mm, thus occupying a volume of 1.6 milliliters and a surface area of 4 $cm^2$. Different types of diagnostic agar-based media may be used in the test chambers of the kit plate: Blood agar 51 (Enriched); Simmons citrate 62 (Differential); Azide blood agar 52 (Selective); Lactose MacCorney agar 53, Glucose MacConkey agar 54, Mannitol MacConkey agar 55, Inositol MacConkey agar 57, Sucrose MacConkey agar 58, Arabinose MacConkey agar 59, Hektoen enteric agar 60, Mannitol salt agar 61, Pseudomonas agar F 63, Pseudomonas agar P 64, and MUG MacConkey agar 65, (Differential-Selective); Bile esculin azide agar 56, Tellurite Glycine agar 66, Littman oxgall agar 71, and Mueller Hinton agar 67–70 and 72–75 (Single purpose). FIG. 2 shows a color view of the illustrated embodiment of the kit plate before antimicrobial disk-quarters are applied to the kit plate 80. Lid 78 is also shown.

FIG. 3 illustrates Brain Heart infusion broth (BHIB) 82 and a specimen containing culture swab 84. The breakaway cap 86 and stopper 88 are associated with the broth 82 container. Incubator 135 and Inoculated incubated Brain Heart infusion broth (IIBHIB) 90 are also illustrated.

FIG. 4 illustrates a dilution 96 of the Inoculated incubated Brain Heart infusion 90, to a concentration that is equivalent to a 0.5 McFarland turbidity standard 94. Other standards are zero McFarland turbidity standard 92 and 1 McFarland turbidity standard 98.

FIG. 5 illustrates an embodiment of the kit plate 80 ready to receive dilution 96, one of two dilutions used for kit plate inoculation. A disposable sterile pipette 100 is also shown.

FIG. 6 shows a device 102A shown in the charging position which may be used in the placement of antimicrobial disk-quarters 110. The device may comprise two parts: a quilter's pin 104 and a push-off slider 106 made from a small pipette tip. The antimicrobial storage container 108 is also shown. FIG. 18 illustrates the placing device in the discharge position 102B. The process of applying the antimicrobial agents on the kit plate may be done with other devices than the one shown in the illustrated embodiment such as tweezers, forceps, vacuum devices, static electricity, air driven applicators or any other method or mechanism of placement.

Figure 37A:
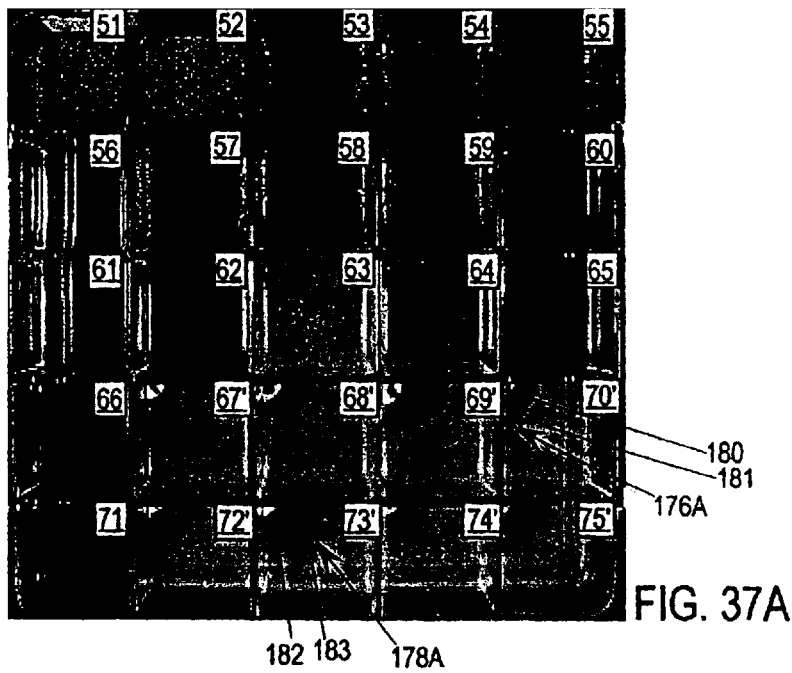
FIG. 37A shows an example of an incubated kit plate consisting of a mixture of *E.coli* and *Staphylococcus aureus;*

FIG. 37A illustrates an incubated kit plate containing two microorganisms and will be described in more detail below.

Figure 15:
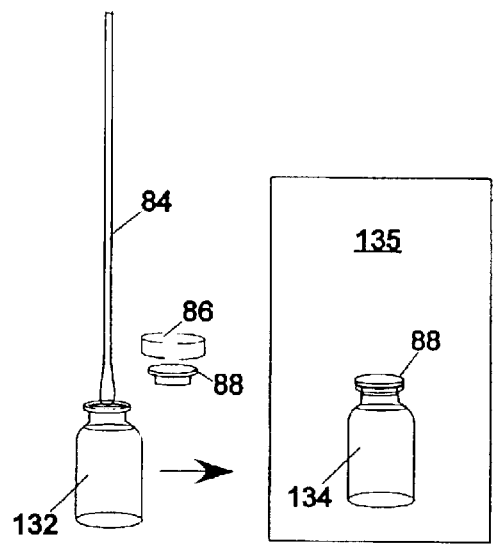
FIG. 15 shows one embodiment of the inoculation of Thioglycolate broth and subsequent incubation.

FIG. 15 illustrates Thioglycolate broth (Thio) 132 and a culture swab containing an initial specimen sample 84. The breakaway cap 86 and stopper 88 may be associated with the broth 132 container. Incubator 135 and inoculated incubated Thioglycolate broth 134 is also illustrated.

FIGS. 16A–16D illustrates components for preparation of dilutions from the Inoculated incubated Brain heart infusion broth (IIBHIB) 90: pipette 100, sterile diluent 136, cap 142, McFarland turbidity standards: "0" Standard 92, 0.5 Standard 94, and "1.0" Standard 98 and additional diluents 138 and 140.

Figure 17:
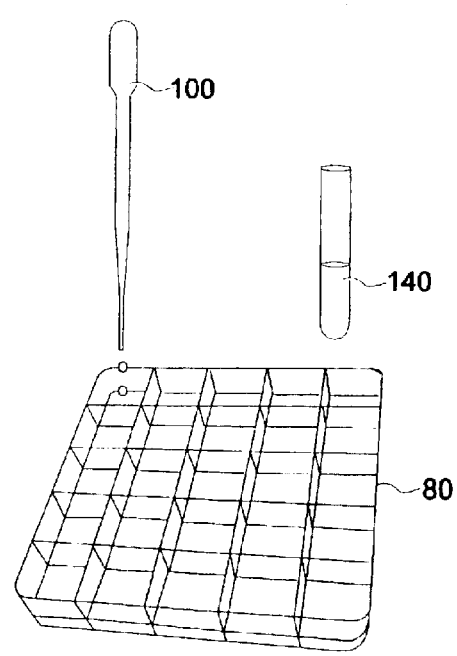
FIG. 17 shows a method of applying a further microorganism suspension dilution (1to 1000 of the 0.5 McFarland equivalent dilution) of to the top two rows of the kit plate.

FIG. 17 illustrates a kit plate 80, ready to receive dilution #140, second of two dilutions. Also shown is a disposable sterile pipette 100.

FIG. 18 shows a cut away view of a multi-chambered kit plate 77' with antimicrobial disk-quarters 76 placed in Mueller Hinton-containing test chambers (67', 68', 69', 70', 72', 73', 74', and 75'). The antimicrobial disk-quarter placement device is at discharge position 102B. Also shown is device in charge position 102A, a set of antimicrobial disk-quarters 110 (representing 8 different antimicrobial agents), container 108, and sample finger and thumb placement positions for manipulating the placement device: position 129T, position 129F, position 131T, and position 131F.

FIGS. 19A–19B illustrate the differences of the invention from prior art and an AST chamber 144 from the kit multi-chambered kit plate 77. The principal of the standard Kirby-Bauer disk-diffusion AST test is illustrated in FIG. 19A (review FIGS. 12C–12D). This illustration shows how the shown embodiment of the kit (FIG. 19B, zone radius 142) measures exactly one-half of the measurement of zone diameter 141, the prior art standard method. The zone of inhibition radius measurement 142 is measured from the corner of the chamber containing disk-quarter 76 to a margin 126 located at the interface between growing microorganisms 125 and inhibited microorganisms 127.

FIGS. 20A–20D show the components of a modified nitrate reductase assay: reagent vial lid 145, Griess reagent sulfanilamide 146, Griess reagent N- (1-napthyl) ethylenediamine 148, and phosphoric acid diluent 150. When the three are combined, they make up the Griess working reagent 152. FIG. 20C illustrates a positive griess reaction 154 or a negative griess reaction 156. FIG. 20D illustrates the addition of zinc powder 158 and either a positive griess reaction after zinc 160 or a negative griess reaction after zinc 162.

FIGS. 21A–21C shows the components of a cytochrome oxidase assay: applicator 164, oxidase test paper 166, and water 168. FIG. 21B shows sample 170 addition and FIG. 21C illustrates a positive oxidase test 172 or a negative oxidase test 174.

FIG. 22 shows a table of the media components of an embodiment of the multi-chambered kit plate and associated reference numerals as described earlier this section.

FIG. 23 illustrates a kit plate media layout with the associated reference numerals as described previously in this section.

FIGS. 24A to 24C show the table used for ID) of non-fastidious gram negative bacteria using the results from the incubated kit plate, the nitrate reductase test, the oxidase test, and morphology and motility observations.

The following figures (FIG. 25–FIG. 36) show results of incubations with a number of different microorganisms. As used herein, the term "microorganism" is understood to include, in particular, microbes, bacteria and yeasts. The "Operation of the Invention" section below will describe the details of bacterial identification and antibiotic susceptibility testing for each kit plate.

Figure 37B:
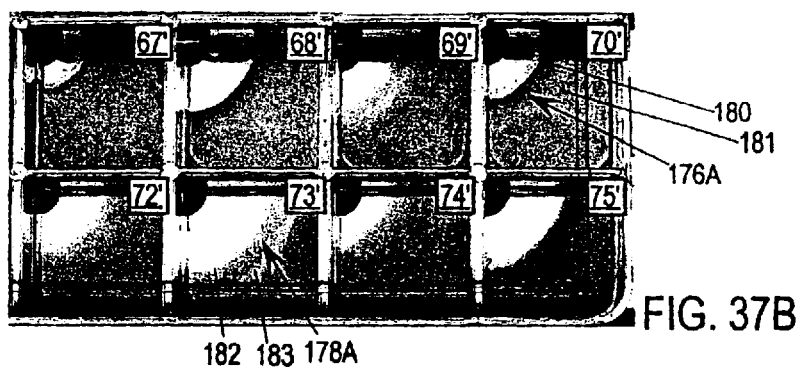
FIGS. 37B to 37C illustrate the microorganisms in FIG. 37A being differentiated on the kit plate in terms of ID as well as AST.
Figure 38:
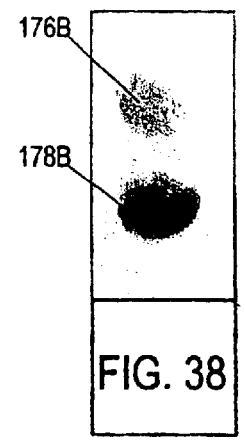
FIG. 38 shows a gram stained slide of the two microorganisms from FIG. 37 separated by their difference in AST to two antimicrobial agents.
Figure 37C:
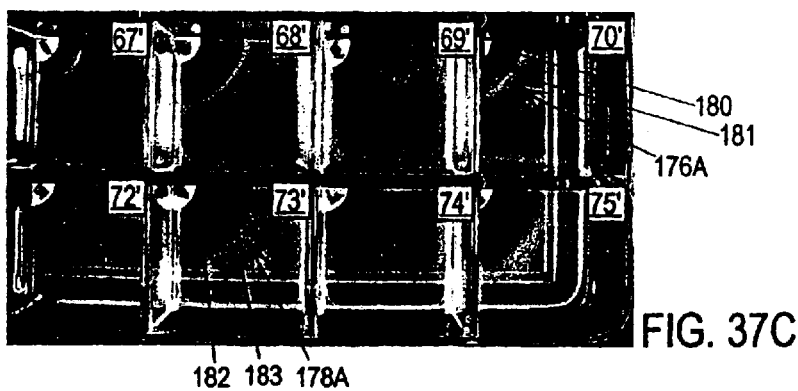

FIGS. 37A to 37C illustrate the growth of two microorganisms, *Staph. aureus* and *E. coli,* on the same kit plate of the invention. FIGS. 37B and 37C are two different views of an enlargement of the AST test chambers (67'–70' and 72'–75'). FIG. 37B shows the test chambers viewed with back lighting. FIG. 37C shows the test chambers viewed with front lighting. Two AST test chambers are featured in these figures: Mueller Hinton agar plus antimicrobial Cephalothin chamber 70' and Mueller Hinton agar plus antimicrobial Enrofloxicin chamber 73'. Two margins are observable in each chamber: *E coli* & cephalothin margin 180 and *Staph. aureus* & cephalothin margin 181 for Cephalothin chamber 70'; and *Staph. aureus* & Enrofloxicin margin 182 and *E. coli* & Enrofloxicin margin 183 for Enrofloxicin chamber 73'. The region 176A is between the *E.coli* margin 180 and *Staph. aureus* margin 181 in Cephaloihin chamber 70'. The region 178A is between the *Staph. aureus* margin 182 and the *E.coli* margin 183 in Enrofloxicin chamber 73'. Illustrated in FIG. 38 are two gram stains 176B and 178B of a sample from regions 176A and 178A respectively.

Figure 39A:
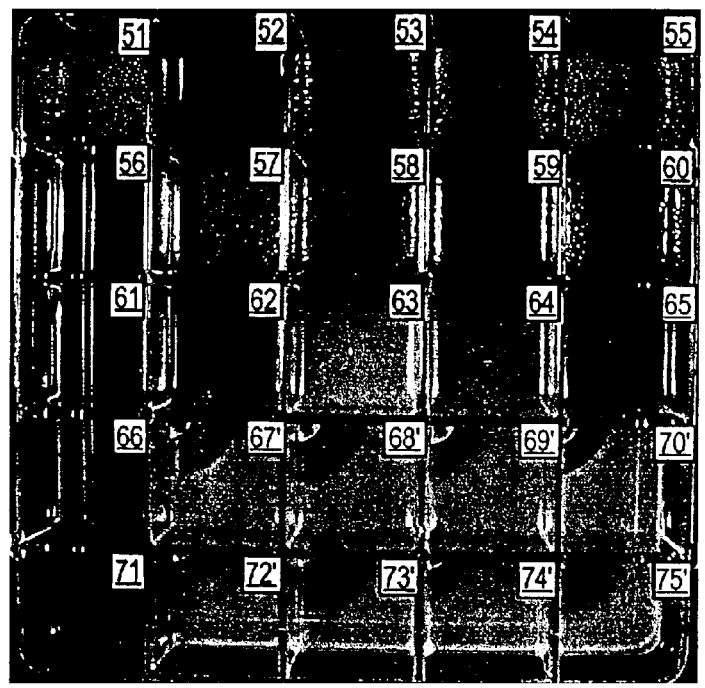
FIGS. 39A to 39E illustrate two microorganisms being differentiated on the kit plate in terms of differences in medium selectivity, fermentation and production of fluorescent product formation.
Figure 39B:
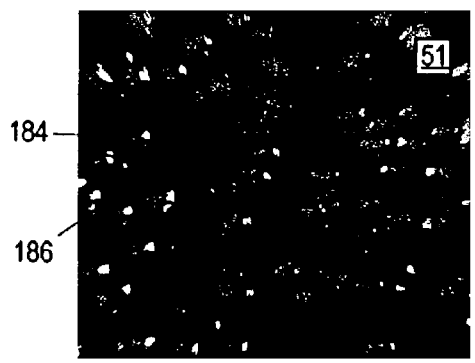
Figure 39C:
Figure 39D:
Figure 39E:

FIGS. 39A to 39E are examples of kit plates of the invention inoculated with a mixture of two microorganisms *E. coli* and *Salmonella typhimurium*. These sets of figures illustrate the utility of the method and kit when several microorganism types are present. FIG. 39A shows the kit plate of the invention and the result of growth and biochemistry of the organisms on the various media. FIG. 39B is a 10× magnification view of Blood agar chamber 51. The view shows two different types of colonies based on size: An *E. coli* colony 184 and a *Salmonella typhimurium* colony 186. FIG. 39C is a 10× magnification view of Hektoen enteric agar chamber 60, illustrating the result of the growth of Salmonella upon the agar. FIG. 39D shows two colony types in the Lactose MacConkey chamber 53, differentiated in terms of their ability to ferment lactose. The pink centered lactose fermenting, *E.coli* 188 is contrasted to the non-lactose fermenting *Salmonella* 190. FIG. 39E illustrates the fluorescence in the MUG MacConkey chamber 65, due to the action of a specific enzyme found in *E. coli.*

The agar-based media of the invention differ from those known in the art in that they are modified to incorporate carrageenan. More specifically, the media of the invention include a carrageenan such as iota carrageenan to extend the useful shelf life of products such as kits produced using the media of the invention. Carrageenan is a compound including mixtures of sulfated polysaccharides which are obtained as extracts of certain species of red seaweed (Rhodophyceae). Carrageenan is most commonly marketed commercially for use in food products. Commercial grades of carrageenan generally range in molecular weight from 100,000 to about 1,000,000. Carrageenan is generally sold as a powder, and is used in the production of food products, cosmetics, and pharmaceuticals. Most commonly, carrageenans are used to stabilize milk proteins and to form water gels.

Carrageenan is generally available commercially in three forms: kappa carrageenan, iota carrageenan, and lambda carrageenan. According to the invention, iota carrageenan may be used to reduce the watering out of hydrocolloid agar gels (termed "syneresis"). In addition, the incorporation of iota carrageenan into agar gels renders agar gels more stable, while increasing the shelf life of the gels produced. Further, according to the invention, the addition of ions such as potassium ions and calcium ions to the iota carrageenan-supplemented agar gels of the invention may further increase the stability of the gels produced. In some embodiments of the invention, iota carrageenan is used to produce stable agar gels. In some embodiments, calcium ions are also added to the gels to further increase their stability.

Agar gels are typically prepared by suspending the agar product in cool water and then heating to boiling. The resulting solution is then allowed to cool to the hydrocolloid gel state. Agar is generally soluble in hot or boiling water. Carrageenan is similarly used by mixing first in cool water and then heating to boiling. The resulting solution is then allowed to cool to the hydrocolloid gel state. Thus, gels according to the invention may be formed by combining powdered agar and carrageenan and dissolving them together, by mixing agar and carrageenan solutions, or using other methods commonly known in the art.

Stable agar gels according to the invention include agar gels such as blood agar, chocolate agar, MacConkey agar, and azide blood agar which further include carrageenan. In some embodiments of the invention, the agar gels include carrageenan in an amount of less than about 1% of the solution by weight. In other embodiments of the invention, the agar gels include from about 0.1% to about 0.8% carrageenan. In still other embodiments of the invention, the agar gels include from about 0.2% to about 0.4% carrageenan. In specific embodiments, the agar gels include 0.2% carrageenan.

In still other embodiments of the invention, stable agar gels are included which incorporate carrageenan and alkaline earth metal ions such as calcium ions. In some such embodiments, the agar gels include alkaline earth metal ions at a concentration of less than about 10 mM. In other embodiments of the invention, the agar gels include from about 0.01 mM to about 1.0 mM alkaline earth metal ion. In still other embodiments of the invention, the agar gels include about 1 mM ion. In some specific embodiments of the agar gels of the invention, the agar gels include about 1 mM calcium ion. Several series of tests were conducted to characterize the carrageenan-infused agar gels of the invention. The results of these tests follow.

EXAMPLE 1

Reduction of Syneresis in Agar-based Media

In a first example, the ability of iota carrageenan to stabilize agar-based media was assessed. The media chosen for this example were used in several of the embodiments of the agar-based media of the invention listed in this application. More specifically, in this example, Blood agar, Chocolate agar, MacConkey agar, and Azide blood agar were each prepared three different ways: (1) without any additions, to serve as a control, (2) with the addition of 0.2% (final concentration) Iota Carrageenan, and (3) with the addition of 0.2% Iota Carrageenan plus 1 mM Calcium chloride. These additions were made at time of hydration as described above, and prior to autoclaving. Following the sterilization step (autoclaving), the processes of preparing blood agar, chocolate agar and azide blood agar from the base media were performed using standard microbiology methods. Defibrinated sterile sheep red blood cells and sodium azide were two of the reagents used. The complete MacConkey medium was prepared using all three ways prior to autoclaving. Each of the twelve different media were dispensed at 50° C. into four polystyrene sterile T-flasks (25 cm$^2$) with tight-fitting screw caps and stored for 28 days at refrigerator temperature (5° C.), at which point the amount of water of syneresis was measured.

The results are summarized in the table entitled: "Syneresis with (1) control, (2) 0.2% iota carrageenan or (3) 0.2% iota carrageenan plus 1 mM calcium, Added to four different agar-based media: Blood, Chocolate, MacConkey, and Azide Blood" which follows. These results are also summarized in FIG. 40.

Referring now to the table of FIG. 40A entitled "Syneresis with (1) Control, (2) 0.2% Iota Carrageenan or (3) 0.2% Iota Carrageenan Plus 1 mM Calcium, Added to Four Different Agar-based media: Blood, Chocolate, MacConkey, and Azide Blood," it is seen that the addition of carrageenan and a combination of carrageenan and calcium reduces syneresis of the hydrocolloid gels. The results shown in FIG. 40A are represented graphically in FIG. 40B. FIG. 40A shows the mean amounts of water of syneresis observed and measured for each set of samples after 28 days. The results shown are expressed in milligrams. As is observed with reference to FIGS. 40A and 40B, in each type of agar tested, the addition of carrageenan decreased the amount of syneresis observed. As shown in FIG. 40A, these results are statistically significant. Indeed, in many cases, syneresis was reduced by at least about 50%. In addition, it was also observed that in each type of agar tested, the addition of calcium further reduced the amount of syneresis observed.

EXAMPLE 2

The Effect of Calcium and Iota Carrageenan Concentration on the Stabilization of Syneresis in the Agar-based Medium, Mueller-Hinton Agar.

In a second example, research was conducted to determine the ability of iota carrageenan to stabilize agar gels at a variety of concentrations of carrageenan with and without calcium. The results of this research are summarized in the tables of FIG. 41A entitled: "The Effect of Iota Carrageenan, Without Added Calcium, on Syneresis of Mueller-Hinton Agar," and in FIG. 42A, entitled: "The Effect of Iota Carrageenan, with 1 mM added Calcium, on Syneresis of Mueller-Hinton Agar. The graphs associated with the above two figures found in FIG. 41B and 42B pictorially illustrate the syneresis-reducing-effect of iota carrageenan and the synergistic effects of adding calcium with certain concentrations of iota carrageenan As seen in the two tables, syneresis is greatly reduced in the agar samples prepared with the addition of iota carrageenan. At several of the concentrations of iota carrageenan the effect of adding calcium is also apparent. Specifically, compare the results shown in FIGS. 41B and 42B with regard to the media containing 0.4%, 0.6% and 0.8% iota carrageenan with and without calcium, respectively.

The configuration, preparation, and manner of use of a first embodiment of a test kit according to the invention is described below. This first embodiment is shown in FIG. 1, which illustrates a testing kit plate of the invention comprising wells filled with enriched, differential, selective, differential-selective and single purpose media. Common base formulations of media and methods of their preparation are known available from the Eleventh edition of the *Difco Manual*. For use in the invention, these formulations are modified by the addition of carrageenan, and in some embodiments, alkaline earth metal ions, to provide a more stable agar gel. According to the invention, the multi-chambered kit plate 80 and associated lid 78 are packed under nitrogen atmosphere in a low oxygen-permeable sealed bag to extend the shelf life.

The process of kit plate media preparation follows standard practices of sterile technique. Envisioned but not illustrated is a process that could be used to produce the kit plates in an efficient fashion. The system conceptually would comprise a temperate regulated box with lid, large enough to hold the individual kit plate chamber medium vessels at 50° C. plus. The distribution of that media to the test chambers of the multi-chambered kit plate would be accomplished by using a dispensing pump able to dispense the correct amount-of media into each test chamber. The pump would drive a multi-channeled pump head with the same number of channels as the number of test chambers in the kit plate allowing for a relatively simple method for manufacturing the multi-chambered kit plates.

A description of the diagnostic usefulness of each of the medium of the multi-chambered kit plate is as follows:

Blood agar 51 is used in the isolation of a wide variety of microorganisms. All non-fastidious gram-negative and gram-positive organisms will grow on this medium. The majority of the aerobic gram-positive and gram-negative bacterial pathogens of domestic animals and man will grow on blood agar when incubated in air at 35° C. Blood agar also allows for determination of hemolytic patterns. The hemolytic patterns adjacent to bacterial colonies are classified as non-hemolytic (gamma hemolysis), complete (beta-hemolysis), and partial (alpha-hemolytic).

Bile esculin azide agar 56 is used for isolating, differentiating and presumptively identifying group D *streptococcus* and *Enterococcus*. These organisms cause the formation of a dark brown or black complex in the agar.

Mannitol salt agar 61 allows staphylococci to grow while the growth of most other bacteria is inhibited.

Tellurite Glycine agar 66 permits the isolation of coagulase positive staphylococci whereas coagulase negative staphylococci and other bacteria are completely inhibited. Coagulase positive staphylococci reduce tellurite and produce black colonies.

Littman oxgall agar 71 is used for the isolation of fungi and is suitable for growth of pathogenic fungi. Incubation is for several days. Molds and yeasts form non-spreading, discrete colonies.

Azide blood agar 52 is used in the isolation of gram-positive organisms from clinical and non-clinical specimens. Azide suppresses the growth of gram-negative bacteria and is useful in determining hemolytic reactions.

Simmons citrate agar 62 is used in the ID of gram-negative organisms that are able to metabolize citrate. The citrate-utilizing organisms grow luxuriantly and the medium becomes alkalinized and changes from its initial green to deep blue.

*Pseudomonas* agar F 64 is used for differentiating *Pseudomonas aeruginosa* from other pseudomonads based on fluorescein production and is visible with UV lamp at 365 nm.

*Pseudomonas* agar P 64 is used for differentiating *Pseudomonas aeruginosa* from other pseudomonads based on the production of pyocyanin, a non-fluorescent blue pigment.

Hektoen enteric agar 60 is used to isolate and differentiate *Salmonella*. Colonies are greenish blue, with black centers.

MUG MAC 65 is a MacConkey agar with lactose plus an added substrate 4-methylumbelliferyl-b-D-glucuronide (MUG). MUG becomes fluorescent when *E.coli* is present. The *E.coli* beta-glucuronidase enzyme cleaves the colorless MUG to a fluorescent product detected with UV light at 365 nm.

MacConkey agar, which contains bile salts, is a selective media for the majority of gram-negative pathogens. The media inhibits gram-positive bacteria and a few gram-negative pathogens. Almost 100% of the genera from the family Enterobacteriaceae (all being gram negative), and nearly 80% of other gram-negative genera grow on Mac-Conkey agar. The following MAC media contain six different sugars to allow for ID of microorganisms based on their fermentation patterns:

Lactose MAC 53 is MacConkey agar with lactose, a selective and differential medium for growing gram-negative bacilli. Lactose fermenting strains grow as red or pink colonies.

Glucose MAC 54 is MacConkey agar with glucose, a selective and differential medium for growing gram-negative bacilli. Glucose fermenting strains grow as red or pink colonies.

Mannitol MAC 55 is MacConkey agar with mannitol, a selective and differential medium for growing gram-negative bacilli. Mannitol fermenting strains grow as red or pink colonies.

Inositol MAC 57 is MacConkey agar with inositol, a selective and differential medium for growing gram-negative bacilli. Inositol fermenting strains grow as red or pink colonies.

Sucrose MAC 58 is MacConkey agar with sucrose, a selective and differential medium for growing gram-negative bacilli. Sucrose fermenting strains grow as red or pink colonies.

Arabinose MAC 59 is MacConkey agar with arabinose, a selective and differential medium for growing gram-negative bacilli. Arabinose fermenting strains grow as red-pink colonies.

Mueller Hinton agar (67–70, 72–75) is considered the best media for routine AST of non-fastidious bacteria. Eight test chambers are set-aside for this purpose.

Each of the above-described agar-based media and others known to those of ordinary skill in the art may be modified to include carrageenan according to the invention. Generally, the carrageenan is mixed with the agar while dry, and then sterilized water is added. The resulting mixture may then be heated to dissolve the components and prepare for addition of any other gel-specific components, such as azide, defibrinated, sheep blood, etc.

FIG. 3 illustrates a crucial part of the method and kit. Instead of the 24 hour prior art method of streaking to isolate individual organisms, a relatively short 4 to 8 hour incubation in Brain-Heart Infusion broth may be utilized. A swab specimen 84 inoculates the broth for growth to a stationary phase 90 in incubator 135. Thioglycolate broth is also included for growth of potential anaerobic microorganisms 134.

The isolation of the microorganisms may be concurrent with a 12 to 20 hour ID testing on the kit plate. Specifically, isolated colonies become visible in the top two rows of the kit plate. These rows received the higher dilution (lower concentration) of microorgarnism(s) 140. The bottom three rows of the kit plate seeded with a higher concentration of microorganisms 96 performs the AST in addition to other tests as described below.

Figures 16A, 16B, 16C, 16D:
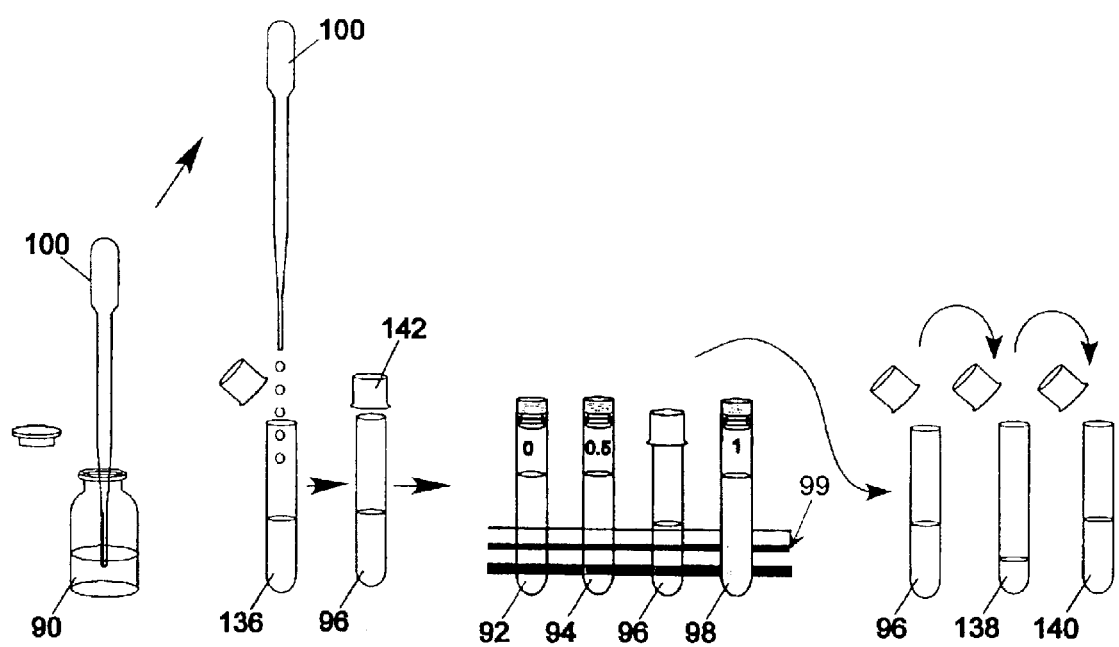
FIGS. 16A to 16D show a method of preparing dilutions directly from initial broth culture (without an isolation step) for inoculating the kit plate.

FIGS. 16A, 16B, 16C, and 16D show the process of preparing the two dilutions (dilution 96 and dilution 140) from the IIBHIB90 for the kit plate inoculation steps as shown in FIG. 5 and FIG. 17. This accomplishes the same thing as the streaking out on a microbiological agar plate as described in the prior art but is much simpler, especially configurations in which there are multiple test chambers involved. The result is that in the top two rows of the kit plate the microorganisms grow up into individual colonies for the purpose of ID. The more concentrated 0.5 McFarland equivalent dilution 138 produces a lawn of microorganisms for the AST test chambers and the other test chambers in the bottom three rows. For the initial kit plate inoculation, a sterile-forty microliter/drop-pipette 100 removes a portion of the grown up (usually to stationary phase) microorganisms (IIBHIB90). Five drops into sterile diluent 136 results in a 1 to 11 dilution. The dilution 96 created is generally close to a 0.5 McFarland turbidity standard as shown in FIG. 16C. Dilution 96 and standard 94 are compared against a black lined background and adjustments made so dilution 96 will be close in turbidity to standard 94. The 0.5 McFarland equivalent dilution 96 is in turn diluted 1 to 1000 by making a 1 to 20 and then a 1 to 50 dilution that becomes the 1 to 1000 dilution 140.

FIG. 5 shows an addition of dilution 96 to the first of fifteen test chambers of the bottom three rows of the kit plate. Eighty milliliters of this dilution is added per chamber. FIG. 17 illustrates the first chamber of the top two rows inoculated using dilution 140. Eighty micro liters of dilution 140 is added per chamber to the ten upper test chambers. Following the additions of the 2 dilutions, the microorganisms may be spread out on the surface of the media by briefly shaking the kit plate in a back and forth motion in both directions. The excess liquid may then be removed by tapping the kit plate upside down into the lid containing an absorbent tissue. The kit plate may then be allowed to air-dry for approximately 10 minutes before the addition of antimicrobial disk-quarters 76.

The method design and placement of antimicrobial agents on the AST portion of the kit plate is a novel and unique modification of the standard Kirby-Bauer disk-diffusion method for AST. FIGS. 19A–19B distinguish the prior art (FIG. 19A) from an AST chamber 144 from the kit plate. One-fourth of an AST disk 124, referred to herein as a "disk-quarter" 76, is placed in the corner of chamber 144, giving exactly the same result multiplied by 2 as the standard disk-diffusion method (inhibition radius 142×2=inhibition diameter 141). FIG. 18 illustrates the placement of disk-quarters 76 into the test chambers using placement device 102. The thumbs and index fingers of both hands may hold the device as shown by the position 129T(right thumb), 129F(right-index finger), 131T(left thumb), and 131F(left -index finger). The hands can be switched if desired. The disk-quarter 76 is picked up with the placement device 102A using a piercing motion into the disk-quarter. The disk-quarter 76 is rotated and placed in the corner of the test chamber. The disk-quarter is then removed by pushing off with the slider as shown by device discharge position 102B.

The kit may also include a modified Nitrate Reductase determination system illustrated in FIGS. 20A–20D as well as a Cytochrome oxidase test as shown in FIGS. 21A–21C. One of ordinary skill in the art will be able to perform these tests, results of which will add additional pieces to the ID puzzle. See FIGS. 24A–24C below for a mechanism of ID. The Nitrate Reductase is determined on the IIBHIB 90 whereas the Oxidase test is run on the individual colonies.

FIG. 22 and FIG. 23 show an embodiment of the kit plate layout and a listing of the culture kit plate media and their purposes. FIGS. 24A to 24C show a database table for identifying non-fastidious gram-negative bacteria using kit results. This database is supplied with the kit and can be searched. After filling in the criteria, search the database for the best match. In some cases, the result is unique. Other cases result in several presumptive choices. However, if other criteria are included, such as colony morphology or cellular morphology, a more definitive ID is possible. Additionally several of the kit plate medium allow for definitive ID such as Hektoen enteric agar for *Salmonella*, MUG MAC for *E. coli* and *Pseudomonas* agar F for the expression of fluorescein in identifying *Pseudomonas aeruginosa*. When the microorganisms form colonies on the MAC media and/or are oxidase positive, the criteria that are utilized for the above database include the following: Citrate utilization; arabinose fermentation; glucose fermentation; inositol fermentation; lactose fermentation; mannitol fermentation; sucrose fermentation; growth on MacConkey based agar; oxidase activity, nitrate reduction; and microorganism motility. All but the last three criteria are obtained from an analysis of the cultured multi-chambered kit plate. The oxidase test and nitrate reductase test are done separately as mentioned above. A discussion of bacterial motility takes place in the next paragraph. The criteria are keyed in as "0" for a negative result and "1" for a positive result and then the database is filtered using a spreadsheet software program. Alternatively, the database can be manually searched.

Motility of bacteria is an important characteristic in the ID of unknown bacteria. To test bacterial motility, a drop of incubation broth is placed on a clean glass slide, a cover slip is added, and the cells are viewed directly for motility. Three types of motion are seen under a microscope: (1) Brownian motion, which is the result of the bombardment of water molecules, (2) Fluid-movement that is due to capillary action, and (3) Motility, which is self-propulsion. The difference between Brownian movement and motility is that motile bacteria move through the liquid whereas in Brownian motion the bacteria just vibrate.

The following figures (FIG. 25–FIG. 36) show results of incubations with a number of different single microorganisms. FIGS. 37A–37C, FIG. 38, and FIGS. 39A–39E illustrate results where more than one organism exists on the same kit plate. This situation highlights the utility of this embodiment of the Kit and method when two microorganisms are present from the same specimen.

Figure 25:
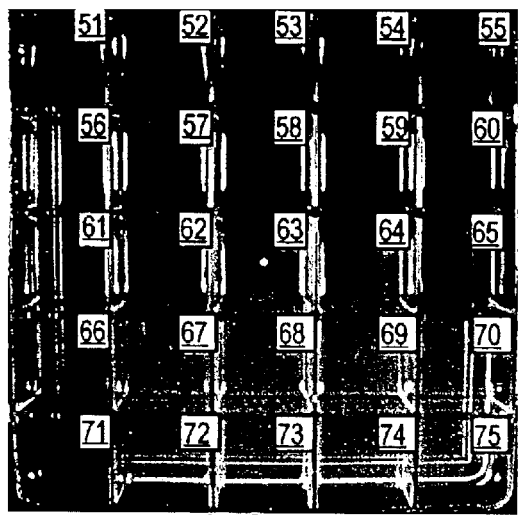
FIG. 25 shows a blank kit plate before addition of microorganisms.

FIG. 25 shows a blank kit plate with media before the addition of microorganisms. This figure provides the initial baseline for appearance and color reactions that take place in the kit plate with various organisms.

Figure 26:
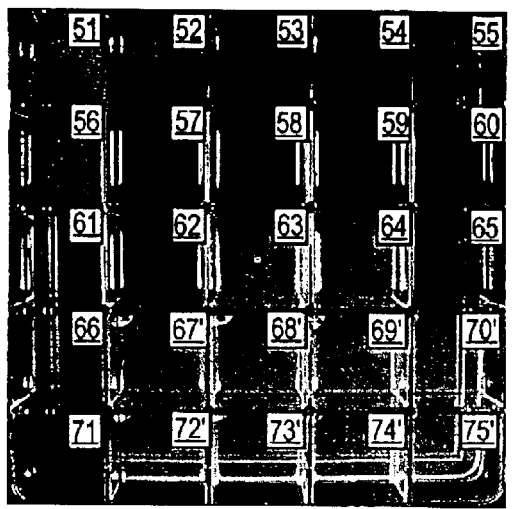
FIG. 26 shows an example of a kit plate incubated for 16 hours following inoculation with the gram-positive organism *Enterococcus faecalis* ATCC 29212.

FIG. 26 shows an example of a kit plate of the invention inoculated and incubated for 16 hours at 35° C. with the gram-positive organism Enterococcus faecalis, ATCC 29212. Blood agar chamber 51 supports the growth of this organism as well as all non-fastidious gram-negative and gram-positive organisms. Shown are non-hemolytic colonies. Azide blood agar chamber 52 also supports the growth of this organism and is non-hemolytic. Gram-negative organisms do not grow on this medium. Bile esculin azide agar chamber 56 shows the formation of a dark brown or black complex in the agar, which is unique to the growth of group D *streptococcus* and *Enterococcus* organisms. Test chambers (67'–70', 72'–75') are the Mueller Hinton AST test chambers containing eight different antimicrobial agents (see the Drawings-reference numerals for the antimicrobial used). The pattern of AST is only faintly evident from this depiction and will not be discussed here.

Figure 27:
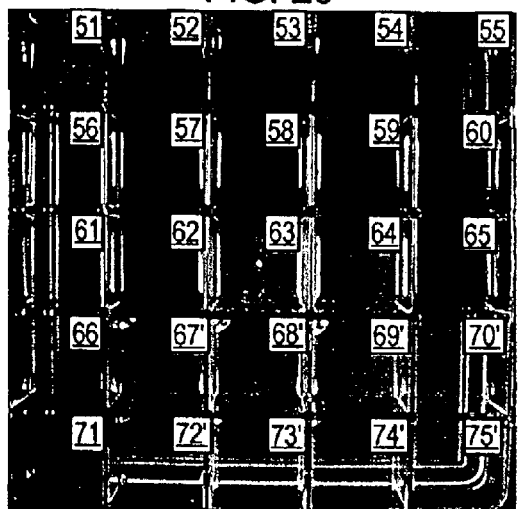
FIG. 27 shows an example of the kit plate incubated for 20 hours following inoculation with the gram-positive organism *Streptococcus pyogenes* ATCC 19615.

FIG. 27 shows an example of a kit plate of the invention inoculated and incubated for 2 hours with the gram-positive organism Streptococcus pyogenes ATCC 19615. Blood agar chamber 51 reveals beta-hemolytic small colonies. Azide blood agar chamber 52 also supports growth.

Figure 28:
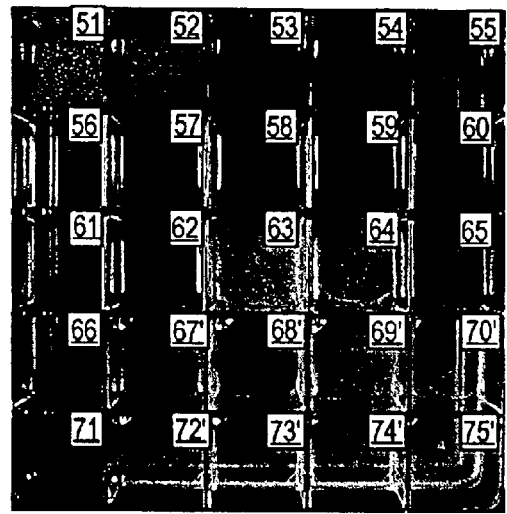
FIG. 28 shows an example of the kit plate incubated for 16 hours following inoculation with the gram-positive organism *Staph. epidermidis* ATCC 12228.

FIG. 28 shows an example of a kit plate of the invention inoculated and incubated for 16 hours with the gram-positive organism *Staph. epidermidis* ATCC 12228. Note the growth in the Blood agar chamber 51 and in the Azide blood agar chamber 52. Note the growth in the Mannitol salt agar 61. All staphylococci will grow in this medium while the growth of most other bacteria is inhibited. Note also the neutral to slightly alkaline color due to the phenol red pH indicator. This shows that the mannitol is not fermented. Fermentation would result in acid products turning the medium yellow. The tellurite Glycine agar 66 also shows no growth. The *Staph. epidermidis* is coagulase negative organism and that media only permits the growth of coagulase positive *Staphylococcus*. The coagulase-negative staph. and other bacteria are completely inhibited on this medium. The coagulase-positive staph. reduces tellurite and produce black colonies when present. *Pseudomonas* agar F chamber 63 and *Pseudomonas* agar P chamber 64, support growth of the Staph. epidermidis but no pigment is produced.

Note the different antimicrobial susceptibilities in FIG. 28, test chambers (67'–70', 72'–75'). To illustrate how AST is performed, look at, for example, FIG. 28 chamber 68', which contains the antimicrobial agent Amoxicillin/Clavulanic acid (Clavamox or Augmentin). Then refer to FIG. 19B which show a schema of a typical endpoint antimicrobial-containing Mueller Hinton chamber. A measurement 142, in millimeters using ruler or caliper, is made from the disk-quarter 76 chamber corner to the margin 126 (the interface between the growing 125 and inhibited 127 microorganisms). To then determine if the microorganisms are Resistant, Intermediate, or Susceptible to the antimicrobial agent, match the measured value to the value listed in the following Modified Interpretive Standards Table (see below).

MODIFIED INTERPRETIVE STANDARDS TABLE:

| Antimicrobial Agent | Resistant | Intermediate | Susceptible |
|---|---|---|---|
| Ampicillin when testing gram negative enteric organisms and *enterococci* | ≦5.5 | 6–6.5 | ≧7 |
| Ampicillin when testing *staphylococci* and penicillin G susceptible microorganisms | ≦10 | 10.5–14 | ≧14.5 |
| Clavamox when testing gram negative enteric organisms and *enterococci* | ≦6.5 | 7–8.5 | ≧9 |
| Clavamox when testing *staphytococci* and penicillin G susceptible microorganisms | ≦9.5 | — | ≧10 |
| Amikacin | ≦7 | 7.5–8 | ≧8.5 |
| Cephalothin (Kelfex) | ≦7 | 7.5–8.5 | ≧9 |
| Doxycycline | ≦6 | 6.5–7.5 | ≧8 |
| Enrofloxicin (Baytril) | <8 | 8–10 | >10 |
| Gentamicin | ≦5 | 5.5–6.5 | ≧7 |
| Trimethoprim-sulfamethoxazole (Septra) | ≦5 | 5.5–7.5 | ≧8 |

Distance from antibiotic corner of chamber to growth margin (mm)

Figure 29:
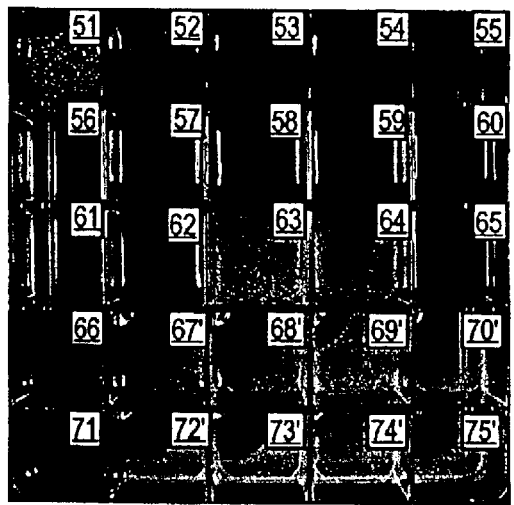
FIG. 29 shows an example of the kit plate incubated for 16 hours following inoculation with the gram-positive organism *Staph. aureus* ATCC 25923.
Figure 30:
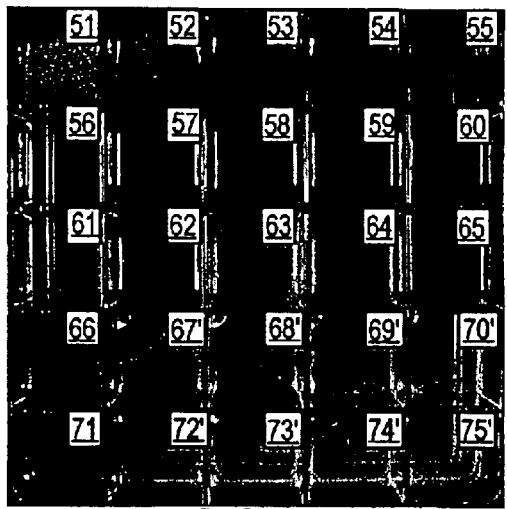
FIG. 30 shows an example of the kit plate incubated for 16 hours following inoculation with the gram-positive organism *Staph. aureus* ATCC 29213.

FIG. 29 and FIG. 30 show examples of two kit plates incubated for 16 hours following inoculation with *Staph. aureus* ATCC 25923 and *Staph. aureus* ATCC 29213 respectively. One primary difference between these two strains is their difference in AST to Ampicillin. Note Ampicillin test chamber 67' in FIG. 29 and FIG. 30. Note the Tellurite *Glycine* agar test chamber 66, illustrating the growth of *Staph. aureus* (a coagulase-positive Staph.) and reduction of the tellurite. Contrast this result to FIG. 28 test chamber 66. Also, note the growth in FIG. 29 and FIG. 30 Azide blood agar test chamber 52 reinforcing the gram-positive nature of those microorganisms.

The next five examples (FIG. 31–FIG. 35) are all gram-negative microorganisms. See the table immediately below for a description of the figures. These figures will be discussed as a group. Note the absence of growth in all Azide blood agar test chambers 52 and the growth in various MAC media (chambers 53, chambers 54, chambers 55, chambers 57, chambers 58, chambers 59, and chambers 65), indicating that all are gram-negative. MUG MAC agar test chambers 65 show growth and fermentation of the lactose containing media in FIG. 31 and FIG. 32 and no-growth in FIG. 33–FIG. 35. More importantly, FIG. 31, (the E coli inoculated kit plate), contains the only MUG-MAC agar chamber 65 that fluoresces when irradiated with UV light at 365 nm (see FIG. 39E for example). FIG. 33, which is the Pseudomonas aeruginosa inoculated kit plate, contains the only pseudomonas F agar test chamber 63 where green pigment is produced (fluorescein). Additionally, irradiation of fluorescein by UV light at 365 nm produces fluorescence (not shown). Note the Hektoen agar test chambers 60 showing growth in FIG. 32, and color change and growth in FIG. 33 and FIG. 35 characteristic of Pseudomonas aeruginosa and Salmonella species. Note the production of Pyocyanin pigment in the Mueller Hinton test chambers (67'–70' and 72'–75'), in FIG. 33 indicative of *Pseudomonas aeruginosa*.

The kit plate of the invention shown contains six test chambers (53, 54, 55, 57, 58, and 59) designed to measure the ability of the test organism to ferment a particular carbohydrate. The carbohydrates used are respectively Lactose, Glucose, Mannitol, Inositol, Sucrose and Arabinose. In addition, MacConkey agar-based media used in the kit plate is selective for the growth of gram-negative organisms only. When fermentation takes place, the medium becomes acidified resulting in red to pink colonies of the bacteria. For example, fermentation is obvious in FIG. 31 test chambers 53, 54, 55, and 59. Contrast this result to FIG. 31 test chambers 57 and 58 where there is growth but no fermentation. The table below lists the results of citrate utilization and fermentation for FIG. 31 through FIG. 35 where "1" denotes a positive result and "0" denotes a negative result. Compare to FIGS. 24A–24C.

Figure 31:
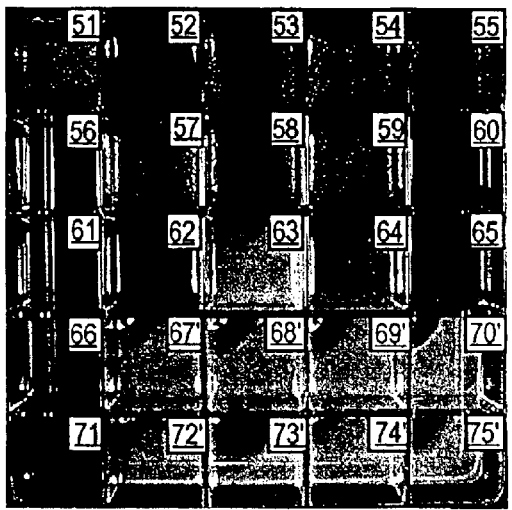
FIG. 31 shows an example of the kit plate incubated for 16 hours following inoculation with the gram-negative organism *E.coli* ATCC 25922.
Figure 32:
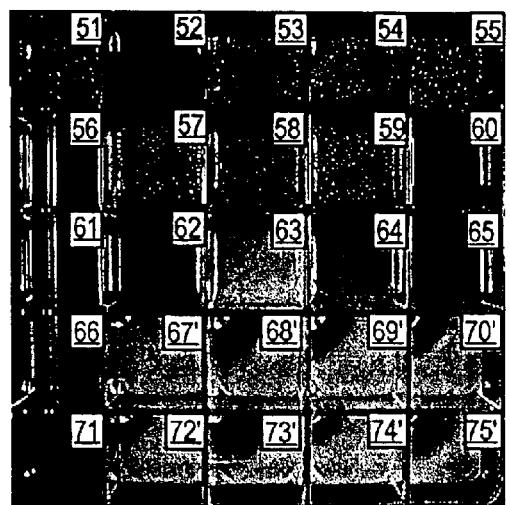
FIG. 32 shows an example of the kit plate incubated for 16 hours following inoculation with the gram-negative organism *Klebsiella pneumoniae* ATCC 13883.
Figure 33:
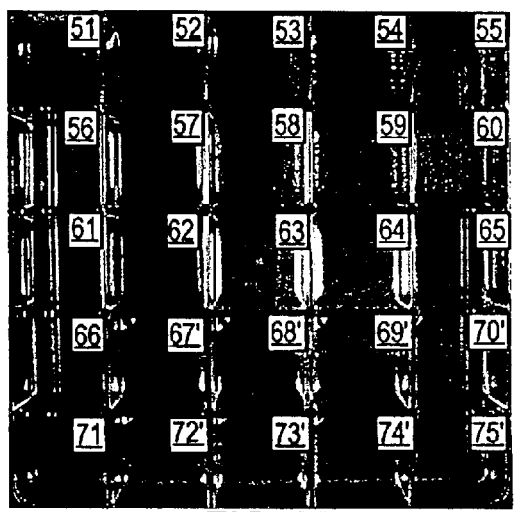
FIG. 33 shows an example of the kit plate incubated for 24 hours following inoculation with the gram-negative organism *Pseudomonas aeruginosa* ATCC 27853.
Figure 34:
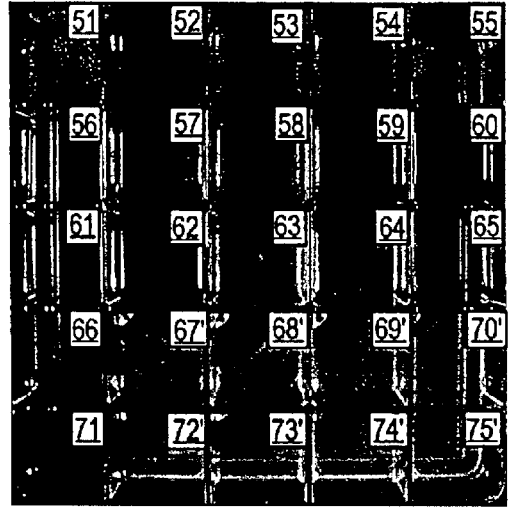
FIG. 34 shows an example of the kit plate incubated for 20 hours following inoculation with the gram-negative organism *Proteus vulgaris* ATCC 13315.
Figure 35:
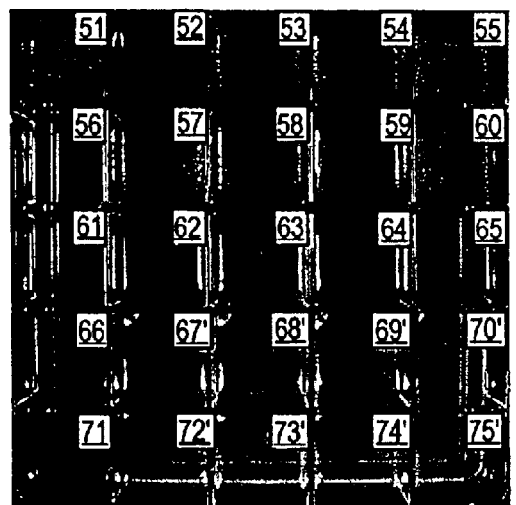
FIG. 35 shows an example of the kit plate incubated for 16 hours following inoculation with the gram-negative organism *Salmonella typhimurium* ATCC 14028.

|  |  | Test chamber number | | | | | | |
|---|---|---|---|---|---|---|---|---|
|  | Gram-negative organism | 62 CIT | 59 ARA | 54 GLU | 57 INO | 53 LAC | 55 MAN | 58 SUC |
| FIG. 31 | *E. coli* | 0 | 1 | 1 | 0 | 1 | 1 | 0 |
| FIG. 32 | *Klebsiella pneumoniae* | 1 | 1 | 1 | 1 | 1 | 1 | 1 |
| FIG. 33 | *Pseudomonas aeruginosa* | 1 | 0 | 1 | 0 | 0 | 0 | 0 |
| FIG. 34 | *Proteus vulgaris* | 0 | 0 | 1 | 0 | 0 | 0 | 1 |
| FIG. 35 | *Salmonella typhimurium* | 1 | 1 | 1 | 0 | 0 | 1 | 0 |

Figure 36:
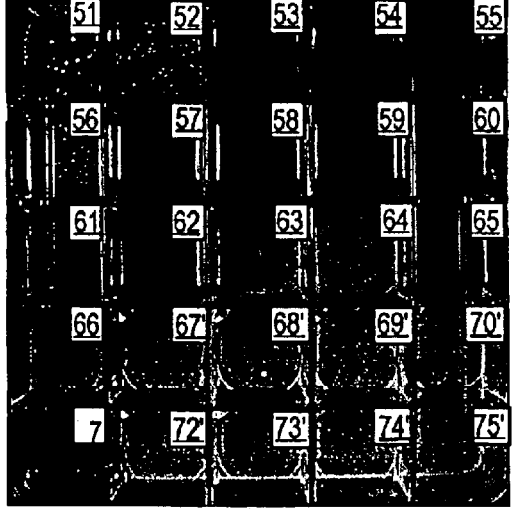
FIG. 36 shows an example of the kit plate incubated for 48 hours following inoculation with the fungus *Candida albicans* ATCC 14053.

FIG. 36 shows an example of the kit plate of the invention incubated for 48 hours after inoculation with the fungus *Candida albicans* ATCC 14053. Perhaps most obvious is the lack of inhibition by any of the eight antimicrobial agents. None of these agents is active against fungus. Note the growth of colonies in Littman oxgall agar 71. This is a useful medium for the isolation of fungi and suitable for the growth of pathogenic fungi. Molds and yeasts form non-spreading, discrete colonies as seen with the *Candida* here.

FIGS. 37A to 37C illustrate the growth of two microorganisms, *Staph. aureus* and *E. coli*, together on the same kit plate. Both organisms, from stock culture, inoculate the BHIB 82. Following a 4-hour incubation at 35° C., two different dilutions are made from the IIBHIB 90 and inoculated on the kit plate as described previously. See above for a complete description of the method. To serve as an example of how to use this kit and method for ID testing and antimicrobial testing of an unknown when more than one microorganism is present, assume that it is unknown what the microorganism or microorganisms are in FIG. 37A. The first step is to take a small volume from the IIBHIB 90, place it on a glass slide and observe the sample under a 400× to 600× microscope. Among the needed observations to be made are: What type of cellular morphology is present? Are there multiple forms? Is there motility? Motile rods and cocci in clustersarepresent. A sample from the IIBHIB 90 is gram stained. The second step is to look at the colonies on the kit plate in the different test chambers. A useful magnifier is 10× microscope eyepiece turned upside down. How many different types of colonies are there? There appears to be two types on the blood agar 51. One of the colonies is hemolytic. Refer to FIG. 10 for a review of the different colony characteristics.

If there are more than two types of microorganisms on the kit plate, consider the following: Although polymicrobic infections do occur, particularly when mixed bacterial species are recovered from deep wounds or visceral organs, this same mixture of organisms from culture of urine, the respiratory tract, or superficial skin wounds or ulcers must be interpreted differently. R. C. Bartlett (Am. J. Clinical. Pathology 61: 867–872, 1974) has recommended that routine cultures that grow three or more organism types should not be further processed. The recovery of three or more organisms from specimens obtained from non-sterile sites most commonly represents colonization or contamination. Repeat cultures may be indicated of there is clinical evidence of infection. Others have reported similar experiences to that reported by Bartlett: that repeat cultures rarely confirm isolation of the same bacterial pathogens.

The third step in the ID of the hypothetical unknown in FIG. 37A is to perform a cytochrome oxidase assays on the colonies growing on the MacConkey media. The results, from testing several colonies from the MacConkey test chambers, are negative for cytochrome oxidase. A nitrate reductase test on the IIBHIB 90 shows that nitrate is reduced during the incubation.

The forth step involves observing the test chambers. FIG. 37A reveals organisms growing on the azide blood agar 52 as well as on a number of the Mac test chambers (53, 54, 55, 57, 58, 59, and 65). This implies a gram negative and gram-positive organism on the kit plate. Neither organism utilizes citrate as seen by the non-reacted green medium in citrate test chamber 62. Mannitol salt agar 61 exhibits growth and is acidic (note yellow color of agar) indicating *Staphylococcus*. In addition, the Tellurite Glycine agar 66 also exhibits growth and is black, which identifies the Staph. as coagulase positive. One strong possibility is *Staph. aureus*.

In step 5, it is found that the MacConkey media shows only one type of colony. Since the organism is growing on the MacConkey media, it is gram negative (also recall the above gram stain results). The organism ferments the following sugars in the respective test chambers: lactose 53, glucose 54, mannitol 155, and arabinose 59. The organism does not ferment inositol 57 or sucrose 58. Step 6 takes the information obtained to this point, and applies the accumulated criteria to the database of FIGS. 24A–24C. The data are filtered to extract out the possible microorganisms with this set of criteria. Following is a copy of the results of that extraction:

| GRAM NEGATIVE ORGANISM | INCUBATION | CIT | ARA | GLU | INO | LAC | MAN | SUC | OXI | NO2 | MOT | MAC |
| --- | --- | --- | --- | --- | --- | --- | --- | --- | --- | --- | --- | --- |
| *E. coli* | 12–20 h | 0 | 1 | 1 | 0 | 1 | 1 | 0 | 0 | 1 | 1 | 1 |
| *Escherichia fergusonii* | 12–20 h | 0 | 1 | 1 | 0 | 1 | 1 | 0 | 0 | 1 | 1 | 1 |
| *Escherichia vulneris* | 12–20 h | 0 | 1 | 1 | 0 | 1 | 1 | 0 | 0 | 1 | 1 | 1 |

*E. coli* is the most common gram-negative microbe isolated and identified in clinical microbiology laboratories. Methylumbelliferyl-beta-D-glucuronide (MUG) is a substrate of the *E.coli* enzyme beta-glucuronidase. MUG becomes fluorescent when this enzyme cleaves it. Incorporating MUG directly into a modified MacConkey agar allows for the direct detection of *E. Coli*. (J. Clinical. Microbiology 1984 Feb; 19(2): 172–4). Useful embodiments of the kit plate may incorporate this medium (MUG-MAC test chamber 65. Step 7 involves irradiating test chamber 65 with UV light at 365 nm. Fluorescence is observed in FIG. 37A, MUG-MAC test chamber 65 (not specifically illustrated but see FIG. 39E for example). The fluorescence confirms *E. coli* as the other microorganism present The AST portion of the kit plate shown in FIG. 37A involves the following test chambers: Ampicillin test chamber 67', Augmentin test chamber 68', Amikacin test chamber 69', Cephalothin test chamber 70', Doxycycline test chamber 72', Enrofloxicin test chamber 73', Gentamicin test chamber 74', and Septra test chamber 75'. Since there are two microorganisms on the above kit plate, they will both be present in the AST chambers. In the event that both organisms are pathogens, the choice would be to treat with the antimicrobial agent which both organisms are sensitive to. Take measurement from the antimicrobial corners to the margins for each microorganism. Then compare these values to the values in the MODIFIED INTERPRETIVE STANDARDS TABLE (above). This allows one to determine if the organism is Sensitive, Intermediate or Resistant for each of the antimicrobial agents.

To determine which margin belongs to which microorganism the following will be helpful. For ease of viewing the margins of each microorganism, FIGS. 37B and 37C provide two different enlarged views of the FIG. 37A AST chambers (67'–70'and 72'–75'). FIG. 37B is a view with back lighting. FIG. 37C is a view with front lighting.

Two AST chambers featured in these figures are the Mueller Hinton agar plus antimicrobial Cephalothin test chamber 70' and the Mueller Hinton agar plus antimicrobial Enrofloxicin test chamber 73'. Two margins are observable in each test chamber: *E coli* margin #180 and *Staph. aureus* margin #181 for the Cephalothin test chamber 70', and *Staph. aureus* margin #182 and *E.coli* margin #183 for the Enrofloxicin test chamber 73'. The region 176A is found to consist of *E.coli* and the region 178A is found to consist of *Staph. aureus* as confirmed by gram staining (FIG. 38) both regions. 176A=176B (gram stained negative rod)=*E. coli* and 178A=178B (gram stained positive cocci)=*Staph. aureus*. Where the cellular morphology is different enough, it would be sufficient to do wet mounts of the regions between the margins to ascertain specific antimicrobial susceptibilities.

There is value in doing AST on the mixture of organisms found in an infectious site. Suppose a hypothetical organism-A possesses an enzymne that inactivates the penicillin antimicrobials. The other organism-B however is sensitive to the penicillins. If the susceptibilities had been done separately or only on organism-B perhaps penicillin would have been used to treat the infection. However, since organism-A is also present, it would inactivate the antimicrobial therapy. The fact is that in the above mixture of *Staph aureus* and *E.coli* , the Staph. does indeed possess the penicillin destroying B-lactamase enzyme.

The last example again involves a mixture of two organisms. However, this time they are both gram negative and both grow on MacConkey media. FIG. 39A is an example of a kit plate inoculated with a mixture of two microorganisms, *E. coli* and *Salmonella typhimurium*. The sets of figures illustrate the utility of the method and kit when several gram-negative is microorganisms are present. FIG. 39A shows the kit plate and the result of growth and biochemistry of the organisms on the various media. The antimicrobial susceptibilities appear to be quite similar. There is no growth in the Azide test chamber 52, which illustrates gram-negative organisms only. Citrate is utilized but it may not clear which organism is utilizing it.

FIG. 39A Hektoen test chamber 60 indicates *Salmonella* is one of the microorganisms. In a closer view, a 10× magnification of test chamber 65 shows the black centered salmonella colonies. A close 10× view of the blood agar test chamber 51 reveals two different types of colonies (FIG. 39B) based on size: An *E. coli* colony 184 and a *Salmonella typhimurium* colony 186. FIG. 39E illustrates fluorescence in the MUG MacConkey test chamber 65, due to the action of *E. coli* beta-glucuronidase enzyme on the substrate 4-methylumbelliferyl-beta-D-glucuronide. *E. coli* is shown to be the other gram-negative. A further look at test chambers glucose 54, mannitol 55, and arabinose 59 show both organisms fermenting those sugars. In addition, inositol 57 and sucrose 58 test chamber show both organisms non-fermenting the sugar substrates. So far, the results match the published criteria. Both organisms ferment glucose, mannitol and arabinose and do not ferment inositol and sucrose. The difference lies in how they handle Lactose. *E.coli* ferments it but *Salmonella typhimurium* does not. A 20× view of the MacConkey lactose test chamber 53, FIG. 39D supports the ID's. *E. coli* colony 188 is fermenting lactose whereas Salmonella typhimurium colony 190 is not fermenting lactose.

The method and kit of the invention is adaptable for the ID and AST of a broad number of microorganisms comprising gram-positive bacteria, gram-negative bacteria, higher bacteria and Mycoplasma, and fungi. The choice of broth used for the initial inoculation may be selected from a number of media that support the growth of the specific type of microorganism in question. In addition, the specimen may be inoculated into any number of growth media and not necessarily a broth type medium. In certain circumstances, such as when a particular organism is suspect, the broth may be rendered selective at the onset with the addition of any number of agents. For example, a specimen possibly containing the gram-positive Bacillus anthracis (Anthrax) needs ID and AST. Let the broth be selective such as Brain-Heart infusion broth plus 50 units/ml of Polymyxin B. This initial incubation media will inhibit most of the gram-negative microorganisms that could be present in a specimen, and favor growth of gram-positive microorganisms. Within 4 to 8 hours, there will be a sufficient number of microorganisms to inoculate the kit plate.

As another embodiment, the multi-chambered kit plate media can include several selective and differential media useful for *Bacillus*: *Bacillus cereus* selective agar (BCA) and/or Phenylethanol agar with 5% defibrinated sheep blood. Anthrax (*Bacillus anthracis*) is a large spore-forming gram-positive rod (1–1.5×3–10 micron) that forms oval, central to sub-terminal spores (1×1.5 micron) that do not cause swelling of the cell. It grows in culture as gray-white colonies, generally flat or slightly convex with characteristic comma-shaped protrusions. The edges are slightly undulate and have a ground glass appearance. Anthrax is differentiated from other gram-positive rods on culture by lack of hemolysis, lack of motility and by preferential lack of growth on Phenylethyl alcohol blood agar. Other Bacilli are generally hemolytic, motile and grow on Phenylethyl alcohol blood agar.

FIG. 1 illustrates an embodiment of one of the kit components, a multi-chambered polystyrene plate having 25 square test chambers and ethylene oxide sterilized. In other embodiments, it is possible for the kit plate to have test chambers of any number and dimension and any composition of plastic material such as polypropylene where the plastic can be formed into a multi-chambered kit plate that can be sterilized. In the case of polypropylene, the kit plate can be steam sterilized instead of ethylene oxide sterilized. Other numbers of test chambers per kit plate can be produced and utilized. In another embodiment, the kit plate may include test chambers of any geometry or shape which provides sufficient surface area for observing bacterial growth.

In an alternative embodiment of the invention, a testing kit is provided having reduced dimensions and a reduced number of agar chambers. In this embodiment of the testing kit within the scope of the invention, the kit plate may be a four-chambered plate. One such suitable plate is a petri dish divided into substantially equal quarters. According to this embodiment of the invention, the four-chambered plate is prepared by partially-filling one chamber with blood agar, another chamber with chocolate agar, another chamber with MacConkey agar, and the final chamber with azide blood agar. According to the invention, the agar preparations used in the testing kit may be the carrageenan-stabilized agar-based gels of the invention to provide a longer shelf life and a more syneresis-resistant agar.

Figure 40:
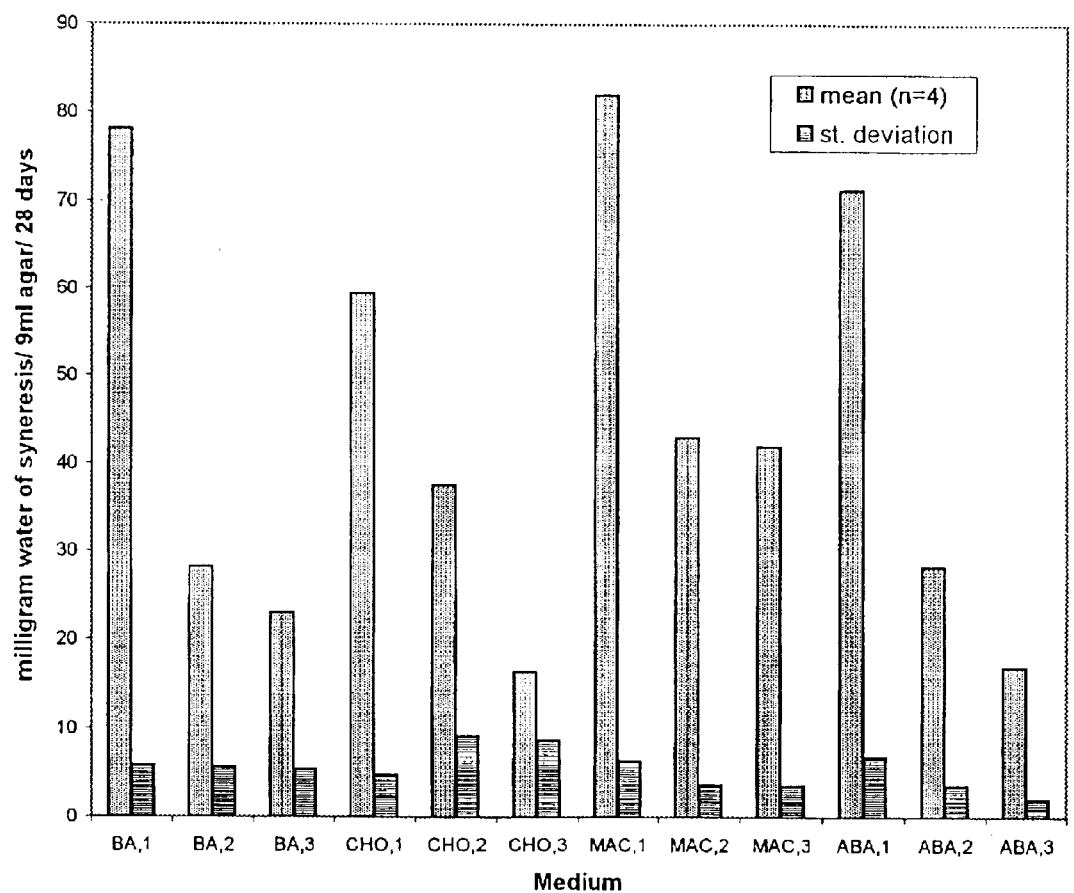
FIG. 40A includes a table entitled "Syneresis with (1) Control, (2) 0.2% Iota Carrageenan or (3) 0.2% Iota Carrageenan Plus 1 mM Calcium, Added to Four Different Agar-based media: Blood, Chocolate, MacConkey, and Azide Blood"
FIG. 40B includes a graphical representation of the table of 40A.
Figure 41B:
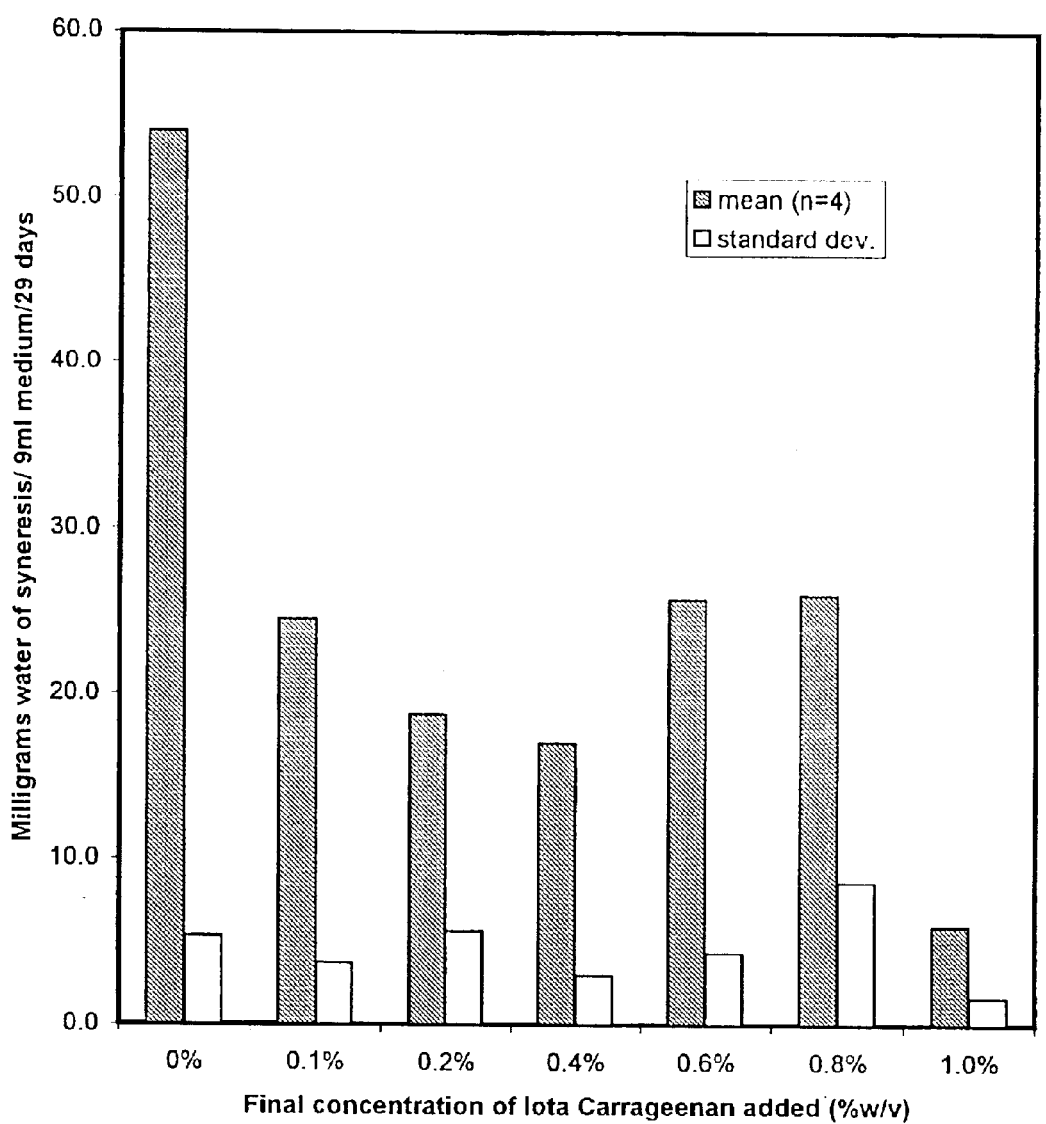
FIG. 41B includes a graphical representation of the table of 41A.
Figure 42B:
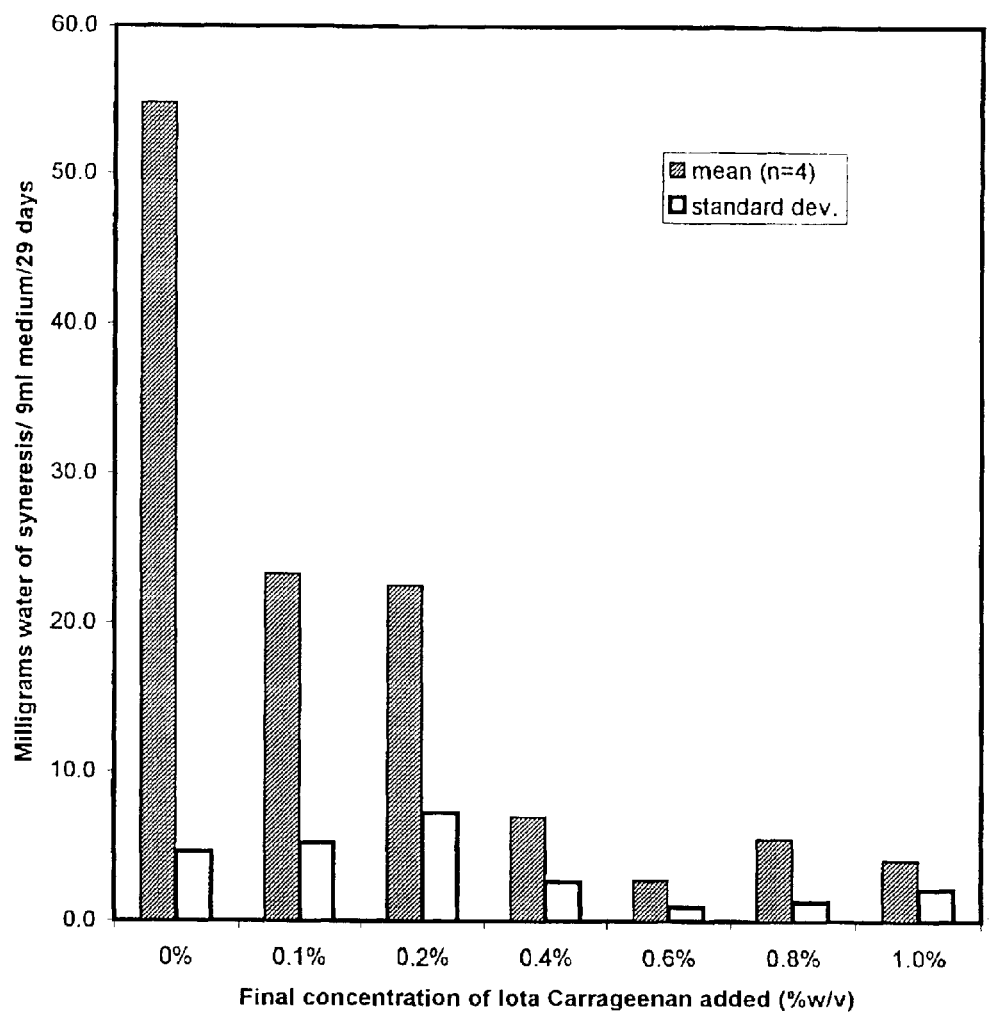
FIG. 42B includes a graphical representation of the table of 42A.

The particular carrageenan-stabilized agars used in the kit may be chosen to allow identification of a wide variety of organisms. Blood agar may be used to culture the majority of aerobic gram-positive and gram-negative bacteria. Chocolate agar grows a similar range of microorganisms, but also supports the growth of several fastidious organisms such as *Haemophilus* and *Neisseria*. MacConkey agar may commonly be provided in a formulation including lactose. In such formulations, MacConkey agar will support the growth of 100% of *Enterobacteriaceae genera* and 80% of other gram-negative genera, while inhibiting the growth of gram-positive organisms. When lactose is provided in the medium, MacConkey agar may allow the determination of whether the bacteria ferment lactose based on the red or pink color of the colony. Azide blood agar allows the growth of gram-positive organisms while inhibiting the growth of gram-negative organisms. Azide blood agar also allows discernment of various types of hemolysis conducted by the bacteria: alpha hemolysis results in greenish discoloration of the culture medium, beta hemolysis is exhibited by the lysis of red blood cells in the media, resulting in a clear zone surrounding the colony, gamma shows no hemolysis, and alpha-prime hemolysis is shown by a small zone of complete hemolysis surrounded by a second zone of partial hemolysis. One example of a kit plate comprising carrageenan-fortified blood agar (BA), chocolate agar (CHO), MacConkey agar (MAC), and azide blood agar (ABA) is shown in FIG. 40.

The testing kit plate thus produced may be used to identify bacteria to the gram (+)/gram (−) level, tests for anaerobes, and allows susceptibility testing against at least about 8 antimicrobial agents. This kit is typically used with 18–24 hour incubation periods. This particular embodiment of the testing kit plate may comprise a portion of a kit including the kit plate, a tube containing sterile water for dilution, a vial of thioglycollate broth, a sterile culture stick, eight antimicrobial disk-quarters, a disk-quarter applicator, and a spreading loop. Alternatively, the kit plate may be sold alone, with subsets of the above-listed equipment, or with additional equipment.

As noted above, the kit plate is used in assays to identify microbes and determine their susceptibility to eight antimicrobial agents. According to one method of using the kit plate, a sample of interest may be diluted using a diluent such as sterile water. A portion of the diluted sample may then be used to inoculate thioglycollate broth, which is subsequently incubated. The diluted sample may then be applied to the blood agar chamber. Proper application of the diluted sample to the chamber generally involves streaking the sample across the plate, and then distributing the streak evenly across the entire chamber using a tool such as a spreading loop. These stepsarethen repeated for the chocolate agar, MacConkey, and azide blood agar chambers.

Following this preparation of the kit plate, antibiotic disk quarters are applied to regions of the plate in order to allow antibiotic susceptibility testing. The "disk quarters" referred to herein are made by dividing Kirby-Bauer susceptibility testing disks into fourths. In other embodiments of the invention, other fractional portions of such Kirby-Bauer disks may be used, including full Kirby-Bauer disks. Other fractional portions, such as "disk-halves" could be used, but may increase the cost of the resulting assay.

In methods of the invention, a number of disk quarters are applied to the blood agar chamber, and a number of disk quarters are applied to the chocolate agar chamber. In some methods of the invention, four disks are applied to each of the blood agar and chocolate agar chambers. In some methods of the invention, amikacin, doxycycline, gentamicin, and septra disks are fractionally divided, and fractions of these disks are applied to the chamber containing blood agar. Similarly, in some methods of the invention, ampicillin, amoxicillin/clavulanate, cephalothin, and enrofloxacin disk fractions may be applied to the chamber containing the chocolate agar. Three of the disk quarters are placed in each of the corners of the agar chamber, and the fourth may be placed along the outside arc-shaped wall of the kit plate. A kit plate of the invention comprising the carrageenan-fortified agars of the invention and demonstrating one potential pattern for placement of the disk-fractions is shown in FIG. 41. The antibiotics subsequently diffuse from the disk quarters into the media, where they may inhibit the growth of bacteria if the bacteria are susceptible to the particular antibiotic agent. Following placement of the disk fractions onto the kit plate; the plate may be incubated for a period of at least 12 hours. In some embodiments of the invention, the incubation period is from about 18 to about 24 hours.

Figure 43:
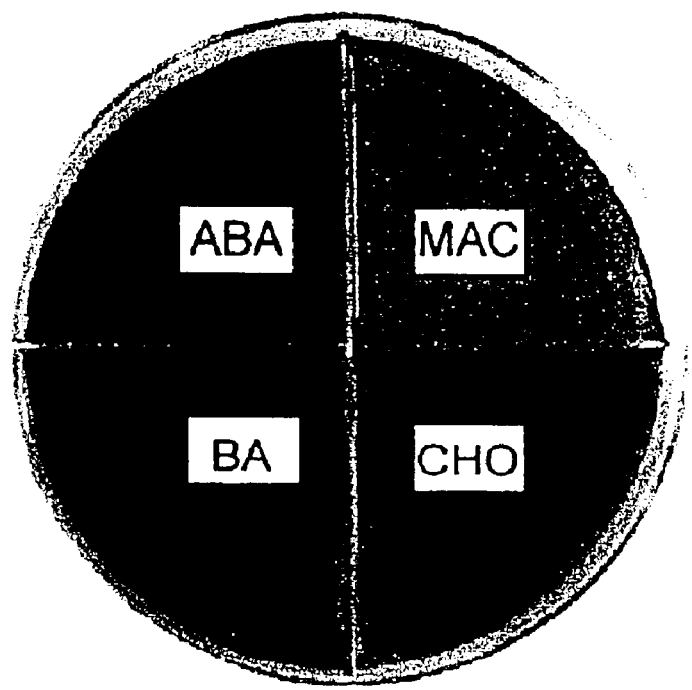
FIG. 43 shows an alternate kit plate comprising carrageenan-fortified agars prepared according to the invention.
Figure 44:
FIG. 44 shows a kit plate of the invention including Kirby-Bauer disk-fractions placed according to some of the methods of the invention.
Figure 45:
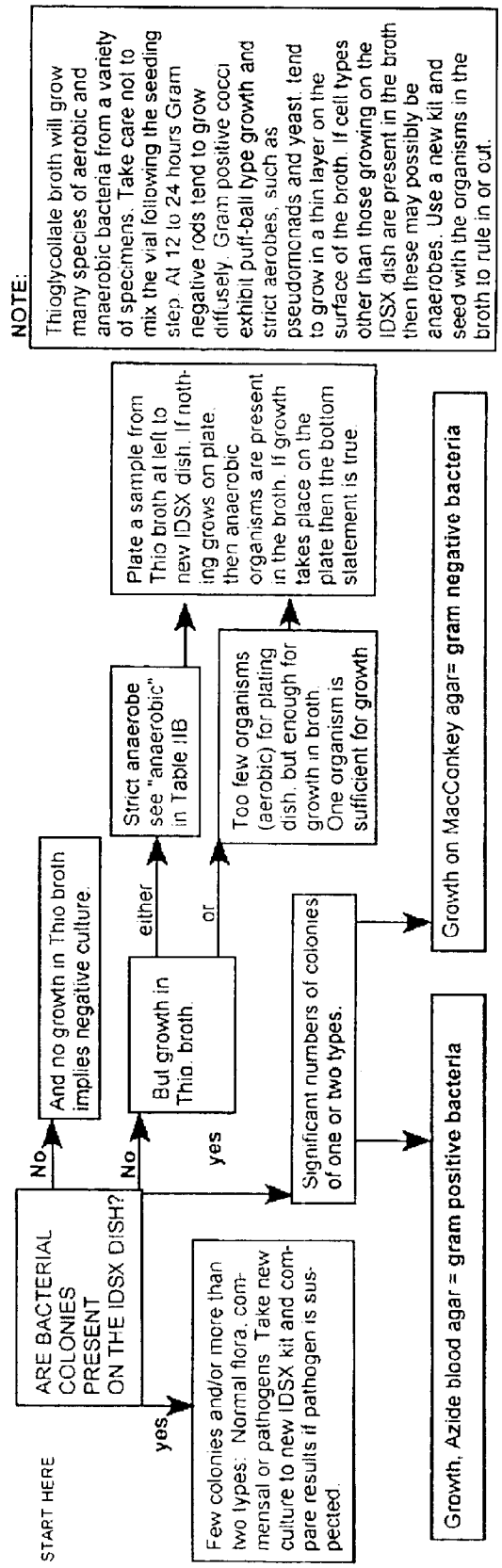
FIG. 45 shows a flow chart which may be used in the methods of the invention to identify bacterial colonies present on the kit plate following incubation.
Figure 46:
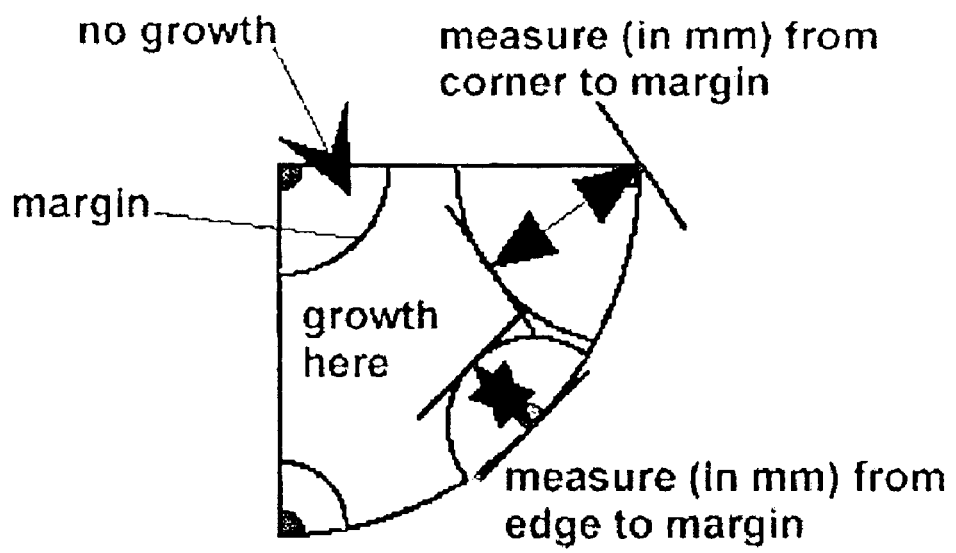
FIG. 46 contains a diagram of a chamber of a kit plate of the invention showing an example of placement of the disk-fractions in the chamber.

Following incubation of the kit, the kit and the thioglycollate broth may be observed to identify the microorganism(s) present and identify compounds to which identified organisms are susceptible. In some methods of the invention, identification of bacteria on the kit and media of the invention may proceed according to methods known in the art. In other methods of the invention, bacterial identification may proceed as shown in the flow chart shown in FIG. 42, entitled "Post incubation (18-hour–48 hour) flow chart ID determination." Following this, susceptibility of the bacteria may be determined by measuring a radius of a zone of no growth of the bacteria from an antibacterial disk fraction. This radius is measured as shown in FIG. 43, and used to determine susceptibility as illustrated in FIG. 44, containing an interpretative standards table. Generally, the larger the zone of growth inhibition, the more effective the antibiotic is against the bacteria present. The zone may be measured as a radius in millimeters from the edge of the dish to the margin. The determined values may be compared with those in the table of FIG. 44, to determine whether the bacterium is resistant, intermediate, or sensitive to a specific antibiotic. The antimicrobial disk quarter placement can be observed to be similar to a standard Kirby-Bauer AST. See FIGS. 19A and 19B.

Microorganism pathogens of animals are frequently classified into two groups: extra cellular and facultative intracellular bacteria and the obligate intracellular and cell associated bacteria. Over 50 genera of extra cellular and facultative intracellular bacteria are listed in the following table (entitled "Characteristics of Genera of Extra Cellular and Facultative Intracellular Bacteria") with their staining reactions, cellular characteristics, and oxygen requirements. Currently all of the non-fastidious microorganisms (marked with "-" under "Fastidious growth requirements") will grow on the illustrated embodiment of the kit plate of the invention. Those that have fastidious growth requirements and/or are anaerobic in their requirement for oxygen will not grow on the illustrated embodiment of the kit plate of the invention. Additional embodiments with different media and/or different gas environments will allow for growth and characterization of these fastidious organisms. The second table (entitled "Table of Media and their Usefulness") lists additional media which may be substituted for the media used in the illustrated kit plate of the invention. Other embodiments would comprise different combinations of the medium listed below as well as newly developed formulations. Mueller Hinton medium, used in this embodiment, may be enriched with other nutrients in another embodiment. Any other suitable AST medium can be used that will allow for reliable AST. In another embodiment, an AST media can be utilized that comprises a selective agent to eliminate unimportant microorganisms, allowing only for the AST of particular pathogens. Further, as taught herein, the agar-based gels used may be stabilized by the addition of carrageenan, and in some embodiments, alkaline earth metal ions.

An embodiment where anaerobic microorganisms are AST tested would utilize a set of antimicrobial agents with clinical indications against anaerobic bacteria. Examples are Clindamycin, Imipenem, Ampicillin-Sublactam, and Metronidazole. It is important to note, concerning anaerobes, that resistance among the B. fragilis group is increasing, while certain Clostridia species are frankly resistant, and therefore AST of anaerobes is very desirable. In another embodiment, additional wells or test chambers are utilized for AST with any available antimicrobial agent under any atmosphere.

In addition to the use of different media, is the option of culturing in different gas atmospheres. These other gas environments are possible with commercial systems. Anaerobic incubators of any brand and make will suffice. A convenient alternative is the pouch systems for the anaerobic incubation of up to two of the kit plates of the invention. These systems comprise a plastic see-through pouch and a paper gas-generating sachet. The paper sachet contains ascorbic acid and activated carbon that react on contact with air. Oxygen is rapidly absorbed and carbon dioxide produced. When the paper sachet is placed in a sealed plastic pouch, the reaction creates ideal atmospheric conditions for the growth of anaerobes.

TABLE

CHARACTERISTICS OF GENERA OF EXTRA CELLULAR AND FACULTATIVE INTRACELLULAR BACTERIA

| Genus | Cell shape | Gram stain | Motility | Oxygen requirement | Fastidious growth requirements |
|---|---|---|---|---|---|
| Micrococcus | Cocci | + | − | Aerobic | − |
| Staphylococcus | Cocci | + | − | Aerobic | − |
| Streptococcus | Cocci | + | − | Aerobic | − |
| Bacillis (has endospores) | Rods | + | − | Aerobic | − |
| Corynebacterium | Rods | + | − | Aembic | − |
| Dermatophilus | Rods | + | + | Aerobic | − |
| Erysipelothrix | Rods | + | − | Aerobic | − |
| Listeria | Rods | + | + | Aerobic | − |
| Nocardia | Rods | + | − | Aerobic | − |
| Propionibacterium | Rods | + | − | Aerobic | − |
| Rhodococcus | Rods | + | − | Aerobic | − |
| Acinetobacter | Rods | − | − | Aerobic | − |
| Actinobacillus | Rods | − | − | Aerobic | − |
| Aeromonas | Rods | − | + | Aerobic | − |
| Alcaligenes | Rods | − | + | Aerobic | − |
| Bordetella | Rods | − | + | Aerobic | − |
| Citrobacter | Rods | − | + | Aerobic | − |
| Edwardsiella | Rods | − | + | Aerobic | − |
| Enterobacter | Rods | − | + | Aerobic | − |
| Escherichia | Rods | − | + | Aerobic | − |
| Klebsiella | Rods | − | − | Aerobic | − |
| Moraxella | Rods | − | − | Aerobic | − |
| Morganella | Rods | − | + | Aerobic | − |
| Pasteurella | Rods | − | − | Aerobic | − |
| Proteus | Rods | − | + | Aerobic | − |
| Providencia | Rods | − | + | Aerobic | − |
| Pseudomonas | Rods | − | + | Aerobic | − |
| Salmonella | Rods | − | + | Aerobic | − |
| Serratia | Rods | − | + | Aerobic | − |
| Shigella | Rods | − | − | Aerobic | − |
| Vibrio | Rods | − | + | Aerobic | − |
| Yersinia | Rods | − | + | Aerobic | − |
| Neisseria | Cocci | − | − | Aerobic | + |
| Mycobacterium | Rods | + | − | Aerobic | + |
| Borrelia | Rods | − | + | Aerobic | + |
| Brucella | Rods | − | − | Aerobic | + |
| Campylobacter | Rods | − | + | Aerobic | + |
| Francisella | Rods | − | − | Aerobic | + |
| Haemophilus | Rods | − | − | Aerobic | + |
| Legionella | Rods | − | + | Aerobic | + |
| Leptospira | Rods | − | + | Aerobic | + |
| Mycoplasma | Rods | − | − | Aerobic | + |
| Taylorella | Rods | − | − | Aerobic | + |
| Peptococcus | Cocci | + | − | Anaerobic | + |
| Peptostreptococcus | Cocci | + | − | Anaerobic | + |
| Veillonella | Cocci | − | − | Anaerobic | + |
| Antinomies | Rods | + | − | Anaerobic | + |
| Bifidobacterium | Rods | + | − | Anaerobic | + |
| Clostridium (has endospores) | Rods | + | + | Anaerobic | + |
| Eubacterium | Rods | + | − | Anaerobic | + |
| Bacteroides | Rods | − | − | Anaerobic | + |
| Fusobacterium | Rods | − | − | Anaerobic | + |
| Treponema | Rods | − | + | Anaerobic | + |

| Medium | TABLE OF MEDIA AND THEIR USEFULNESS<br>Usefulness |
|---|---|
| AS agar | Isolating and differentiating genital strains of mycoplasmas. |
| Actinomycete Isolation Agar | Isolating Actinomycete from soil and water |
| Agar Medium No. F | Detecting Enterobacteriaceae and other gram-negative bacteria in pharmaceutical products |
| American trudeau Society medium | Cultivation of acid-fast bacteria (mycobacteria) |
| Anaerobic Agar | Cultivating anaerobic microorganisms |
| Azide Blood Agar | Isolating streptococci and staphylococci; for use with blood in determining |

-continued

| TABLE OF MEDIA AND THEIR USEFULNESS | |
|---|---|
| Medium | Usefulness |
| Base | hemolytic reactions |
| *Bacillus cereus* selective agar (BCA) | Isolating and differentiating *Bacillus anthracis* in meat and tissue |
| Bacteroides Bile-Esculin agar | Isolation and ID of *Bacteroides fragilis* group and *Biophilia* spp. |
| BG Sulfa Agar | Isolating *salmonella* |
| Baird-Parker Agar Base | Isolating and enumerating *staphylococci* in foods and other materials |
| BIGGY Agar | Isolating and differentiating *Candida* spp. |
| Bile Esculin Agar Base | Isolating and presumptively identifying group D *streptococci* |
| Bile Esculin Agar | Isolating and presumptively identifying group D *streptococci* and *Enterococcus* spp. |
| Bile Esculin Azide Agar | Isolating, differentiating and presumptively identifying group D *streptococci* |
| Bismuth sulfite agar | Selective for *Salmonella* spp. |
| Blood agar, anaerobic (CDC) | General growth medium for anaerobic bacteria |
| Blood agar, anaer. W K & Val (CDC) | Isolation of *Bacteroides* spp. And other obligately anaerobic bacteria |
| Blood Agar Base | Isolating and cultivating a wide variety of microorganisms. Plus blood, fastidious organisms |
| Blood Agar Base No. 2 | Isolating and cultivaling fastidious microorganisms with or without added blood |
| Blood Agar, Laked, anaerobic with K & VA | Isolation of *Bacteroides* spp. And other obligatory anaerobic bacteria with enhanced *Prevotella* pigment production |
| Blood Agar, Phenylethyl alcohol, anaerobic | Isolation of *Bacteroides* spp., *Prevotella* spp., and other obligately anaerobic bacteria from facultative anaerobes. |
| Bordet Gengou Agar Base | Isolating *Bordetella pertussis* and other *Bordetella* species |
| Brain Heart Infusion Agar | Cultivating fastidious microorganisms, especially fungi and yeasts |
| Brain Heart CC Agar | Isolating and cultivating fastidious fungi |
| Brain Heart Infusion w/PAB and Agar | Cultivating fastidious organisms, particularly from blood containing sulfonamides |
| Brewer Anaerobic Agar | Cultivating anaerobic and microaerophilic bacteria |
| Brilliant Green Agar | Isolating *Salmonella* other than *Salmonella typhi* |
| Brilliant Green Agar Modified | Isolating *Salmonella* from water, sewage and foodstuffs |
| Brilliant Green Bile Agar | Isolating, differentiating and enumerating coliform bacteria |
| *Brucella* Agar | Isolating and cultivating *Brucella* |
| Campylobacter Agar Base | Isolating and cultivating *Campylobacter* |
| *Candida* BCG Agar Base | Isolating and differentiating *Candida* from primary specimens |
| *Candida* Isolation Agar | Isolating and differentiating *Candida albicans* |
| Cetrimide Agar | Isolating and cultivating *Pseudomonas aeruginosa* |
| Base Charcoal Agar | Cultivating fastidious organisms, especially *Bordetella pertussis* fro vaccine production |
| Chocolate Agar | Supports growth of *Neisseria* and *Haemophilus* |
| *Clostridium difficile* selective media | Isolating *C. difficile* from fecal specimens of patients |
| Columbia Blood Agar Base EH | Isolating and cultivating fastidious microorganisms when used with blood |
| Columbia Blood Agar Base | Cultivating fastidious microorganisms with or without the addition of blood |
| Columbia Blood Agar Base No. 2 | Isolating and cultivating fastidious microorganisms when used with blood |
| Cooke Rose Bengal Agar | Isolating fungi from environmental and food specimens |
| Corn Meal Agar | Stimulating the production of *chlamydospores* by *Candida albicans* |
| Cystine Heart Agar | Cultivating *Francisella tularensis* when used witb blood |
| Cystine | Used with added carbohydrates in differentiating microorganisms based on |

-continued

TABLE OF MEDIA AND THEIR USEFULNESS

| Medium | Usefulness |
|---|---|
| Tryptic Agar | fermentation reactions |
| Czapek Solution Agar | Cultivating fungi and bacteria capable of using inorganic nitrogen |
| DCLS Agar | Isolating gram-negative enteric *bacilli* |
| D/E Neutralizing Agar | Used for neutralizing and determining the bactericidal activity of antiseptics and disinfectants |
| DNase Test Agar w/Methyl Green | Identify potentially pathogenic *staphylococci* based on deoxyribonuclease activity |
| DRBC Agar | Enumeration of yeasts and molds |
| Desoxycholate Agar | Isolating and differentiating gram-negative enteric *bacilli* |
| Desoxycholate Citrate Agar | kolating enteric *bacilli*, particularly Salmonella and many Shigella species |
| Desoxycholate Lactose Agar | Isolating and differentiating gram-negative enteric *bacilli* and enumerating coliforms from water, wastewater, diary |
| Dextrose Agar | Cultivating a wide variety of microorganisms with or without added blood |
| Dextrose Starch Agar | Cultivating pure cultures of *Neisseria gonorrhoeae* and other fastidious microorganisms |
| Dextrose Tryptone Agar | Cultivating thermophilic "flat-sour" microorganisms associated with food spoilage |
| Differential Reinforced Clostridial Agar | Cultivating and enumerating sulfite-reducing *clostridia* |
| Dubos Oleic Agar Base | Isolating and determining the susceptibility of *Mycobacterium tuberculosis* |
| Egg Yolk Agar | Differentiate species of anaerobic and aerobic bacteria based on detection of lecithinase, lipase, and protease activity |
| M E Agar | Isolating and differentiating *enterococci* from water by membrane filtration |
| Esculin Iron Agar | Enumerating *enterococci* from water by membrane filtration based on esculin hydrolysis |
| EMB Agar | Isolating and differentiating gram-negative enteric *bacilli* |
| Emerson YpSs Agar | Cultivating Allomyces and other fungi |
| Endo Agar | Confirming the presence of coliform organisms |
| *M Enterococcus* Agar | Isolating and enumerating *enterococci* in water and other materials by membrane or pour plate techniques |
| Eugon Agar | Cultivating a wide variety of microorganisms, particularly in mass cultivation procedures. |
| M FC Agar | Cultivating and enumerating fecal coliforms by membrane filter technique at elevated temperatures |
| HC Agar Base | Enumerating molds in cosmetic products |
| M HPC Agar | Enumerating heterotrophic organisms in treated potable water and other water samples by membrane filtration |
| Heart Infusion Agar | Cultivating a wide variety of fastidious microorganisms and as a base for preparing blood agar |
| Hektoen Enteric Agar | Isolating and differentiating gram-negative enteric *bacilli* |
| KF *Streptococcus* Agar | Isolating and enumerating fecal *streptococci* according to APHA |
| LPM Agar Base | Isolating and cultivating *Listeria monocytogenes* |
| *Lactobacilli* MRS Agar | Isolation, enumeration and cultivation of *Lactobacillus* species |
| Letheen Agar | Evaluating the bactericidal activity of quaternary, ammonium compounds |
| Lima Bean Agar | Cultivating fungi |
| Littman Oxgall Agar | Isolating and cultivating fungi, especially dermatophytes |
| Liver Infusion Agar | Cultivating *Brucella* and other pathogenic organisms |
| Liver Veal Agar | Cultivating anaerobic microorganisms |
| M 17 Agar | Enumerating lactic *streptococci* in yogurt, cheese starters and other dairy products |
| MYP Agar | Enumerating *Bacillus cereus* from foods |
| MacConkey Agar | Isolating and differentiating lactose fermenting from non-fermenting gram-negative enteric *bacilli* |
| MacConkey Agar Base | Used with added carbohydrates in differentiating microorganisms based on fermentation reactions |
| MacConkey Agar CS | Isolating and differentiating gram-negative enteric *bacilli* from specimens containing swarming strains of *proteus* |
| MacConkey Agar w/o Salt | Isolating and differentiating gram-negative *bacilli* while suppressing the swarming of most *proteus* species |
| MacConkey Agar w/o CV | Isolating and differentiating enteric microorganisms while permitting growth of *staphylococci* and *enterococci* |
| MacConkey Sorbitol Agar | Isolating and differentiating enteropathogenic *E. coli* serotypes |
| Malt Agar | Isolating and cultivating yeasts and molds from food, and for cultivating yeast and mold stock cultures |
| Malt Extract Agar | Isolating, cultivating and enumerating yeasts and molds |

-continued

TABLE OF MEDIA AND THEIR USEFULNESS

| Medium | Usefulness |
| --- | --- |
| Mannitol Salt Agar | Isolating and differentiating *staphylococci* |
| McBride Listeria Agar | Isolating *Listeria monocytogenes* with or without the addition of blood |
| McClung Toabe Agar Base | Isolating and detecting *Clostridium perfringens* in foods based on the lecithinase reaction |
| Microbial Content Test Agar | Detection of microorganisms on surfaces sanitized with quaternary ammonium compounds |
| Mueller-Hinton medium plain | Testing bacteria for susceptibility to antimicrobial agents |
| Mueller-Hinton m. with 5% sheep B. | As above with MH plain plus testing strains of *Streptococcus* spp. And other fastidious bacteria |
| Mueller-Hinton m. chocolatized | As above for MH plain, MH with 5% sheep blood plus testing *Haemophilus* and *Neisseria* |
| Mycobacteria 7H1 I Agar | Isolating, cultivating and AST testing of fastidious strains of mycobacteria |
| Milk Agar | Enumeration of microorganisms in liquid milk, ice cream, dried milk and whey |
| *Mitis Salivarius* Agar | Isolating *Streptococcus mitis, S. salivrius* and *enterococci,* particularly from grossly contaminated specimens |
| Modified Letheen Agar | Microbiological testing of cosmetics |
| Mycobiotic Agar | Isolating pathogenic fungi |
| Mycological Agar | Cultivating fungi at a neutral pH |
| Mycological Agar w/Low pH | Isolating and cultivating fungi and aciduric bacteria |
| Oatmeal Agar | Cultivating fungi, particularly for macrospore formation |
| Orange Serum Agar | Cultivating aciduric microorganisms, particularly those associated with spoilage of citrus products |
| PPLO Agar | Isolating and cultivating *Mycoplasma* |
| Peptone Iron Agar | Detecting hydrogen sulfide production by microorganisms |
| Phenylethanol Agar | Isolating gram-positive microorganisms but markedly to completely inhibiting gram-negative microorganisms |
| Phenylalanine Agar | Differentiating *Proteus* and *Providencia* species from other *Enterobacteriaceae* based on deamination of phenylalanine |
| Potato Dextrose Agar | Culturing yeasts and molds from food and dairy products |
| Protease No. 3 Agar | Isolating and cultivating *Neisseria* and *Haemophilus* |
| *Pseudomonas* Agar F | Detecting the production of fluorescein. Produced by *P. seruginosa, P. putida, P. fluorescens* and unidentified *fluor. P.* |
| *Pseudomonas* Agar P | Detecting and differentiating *Pseudomonas aeruginosa* from other pseudomonas based on pyocyanin production |
| *Pseudomonas* Isolation Agar | Isolating *Pseudomonas* and differentiating *Pseudomonas aeruginosa* from other pseudomonads based on pigment |
| Rice Extract Agar | Differentiating *Candida albicans* and other *Candida* spp. Based on chlamydospore formation |
| Rose Bengal Agar Base | Isolating and enumerating yeasts and molds |
| SABHI Agar Base | Isolating and cultivating pathogenic fungi |
| SPS Agar | Detecting and enumerating *Clostridium perfringens* in food |
| Sabouraud Dextrose Agar | Culturing yeasts, molds and aciduric microorganisms |
| *Salmonella-Shigella* Agar | Isolation of *Salmonella* spp. And many strains of *Shigella* spp. From feces |
| Sabouraud Maltose Agar | Culturing yeasts, molds and aciduric microorganisms |
| Simmons Citrate Agar | Differentiation of enteric gram-negative *bacilli* from clinical specimens, water samples, and food samples |
| Spirit Blue Agar | Detecting and enumerating lipolytic microorganisms in diary products |
| TCBS Agar | Isolating and cultivating *Vibrio cholerae* and other enteropathogenic vibrios |
| M TEC Agar | Isolating, differentiating and enumerating thermotolerant *E. coli* from water by membrane filtration |
| TPEY Agar Base | Detecting and enumerating coagulase-positive *staphylococci* |
| Tellurite Glycine Agar | Isolating coagulase-positive *staphylococci* |
| *Thermoacidurans* Agar | Isolating and cultivating *Bacillus coagulans* (*Bacillus theremoacidurans*) from foods |

-continued

TABLE OF MEDIA AND THEIR USEFULNESS

| Medium | Usefulness |
|---|---|
| Thiosulfate citrate bile salts sucrose agar | Isolating *Vibrio cholerae* and other pathogenic vibrios from samples of feces and food containing mixed species |
| Tomato Juice Agar | Cultivating and enumerating *Lactobacillus* species |
| Tomato Juice Agar Special | Cultivating and enumerating *lactobacilli* and other acidophilic microorganisins ftom saliva and other specimens |
| Triple Sugar Iron Agar | Differentiating gram-negative enteric *bacilli* based on fermentation of dextrose, lactose, sucrose and on H2S production |
| Tryptic Soy Agar | Isolating and cultivating fastidious microorganisms and, with blood, in determining hemolytic reactions |
| Tryptone Glucose Extract Agar | Cullivating and enumerating microorganisms in water and dairy products |
| Tryptose Agar | Isolation of *Brucella* from blood |
| Tryptose Blood Agar Base | Isolating, cultivating and determining the hemolytic reactions of fastidious microorganisms |
| VJ Agar | Isolating coagulase-positive, mannitol-fermenting *staphylococci* |
| Veal Infusion Agar | Cultivating fastidious microorganisms with or without the addition of blood |
| *Veillonella* Agar | Isolating *Veillonella* when used with vancomycin |
| Violet Red Bile Agar | Enumerating coliform organisms in dairy products |
| Violet Red Bile Agar with MUG | Enumerating *E. coli* and total coliform bacteria in food and dairy products |
| Violet Red Bile Glucose Agar | Detecting and enumerating *Enterobacteriaceae* in food and dairy products |
| XLD Agar | Isolating and differentiating gram-negative enteric *bacilli*, especially *Shigella* and *Providencia* |
| XLT4 Agar Base | Isolating non-typhi *Salmonella* |
| YM Agar | Cultivating yeasts, molds and other aciduric microorganisms |
| Yeast Extract Glucose Chloramphenicol Agar | Enumerating yeasts and molds in milk and milk products (recommended by International dairy Federation) |
| *Yersinia* Selective Agar Base | Isolating and cultivating *Yersinia enterocolitica* |

SUMMARY

The methods and kits described herein provide a novel and unique diagnostic tool for the characterization of unknown microorganisms from any source. The advantages take on significant meaning in a world where the unseen microscopic enemy either conquers or is conquered. The outcome depends on the readiness of the body's defense system to fight the pathogen plus how quickly the organism is identified, susceptibility tested and treatment started. The sooner the administration of the right antibiotic, the better the chance is for winning the battle.

The kits of the invention may yield results (concurrent ID and AST) in as little as one-third the time of standard methods, usually within 24 hours. This may provide a critical advantage in situations of life-threatening illnesses where it is important to know which antibiotic to use as well as the ID of the pathogen. Further, the kits may be constructed in such a manner as to be cost effective and may be complete such that no additional items are needed to implement or use them.

According to the methods of the invention, the specimen may be directly inoculated into the kit broth with no delay in transporting the specimen. Generally within 4 to 6 hours, the broth culture is diluted and inoculated onto the ID-ASI kit plate. In other previously described embodiments, the specimen can be taken directly to the plate media. The antimicrobial portion (AST) shows visible results even by 8 hours, with the faster growing Enterobacteriaceae family of microorganisms. The kit may be used anywhere that an incubation temperature can be maintained (35° C.–37° C.). The kit is versatile in that many different types of organisms are tested at the same time. Since there is no initial isolation step, there is a reduced likelihood of errors in judgment.

The AST portion of the kit is also novel and unique in that the end-of-incubation measurements correlate exactly ($\times\frac{1}{2}$) to the standard Kirby-Bauer disk-diffusion AST system. Any set of antimicrobial agents can be tested and more than one microorganism can exist in the same test chamber and still be analyzed (see above). Finally, the stabilized agar media formulations of the invention provide kits having an extended shelf life and increased reliability due to a significant reduction in syneresis.

A paradigm in microbiology is that isolated colonies are required (i.e. "pure cultures") before any identification testing can begin. Streak plates are prepared and incubated for that purpose. Eighteen to 24 hours later, the colonies that form are tested by picking them from the plate and transferring for additional growth (18–24 hours) in identification systems or ID media. When the ID is established, an additional 18–24 hours are required to do AST for each microorganism deemed important. Another paradigm states that to do an AST test it is again required to first isolate the organism(s) of interest. The present method and kit allows for a significant short cut with no sacrifice to reliability. Isolations and identifications of several microorganism types take place together in the same chambers at the same time without the need for an initial 18 to 24 hours isolation step first. A broth is inoculated in one embodiment, which takes generally 4 to 6 hours to grow up the microorganisms. Then dilutions are made and inoculated into the kit plate that performs the testing (ID concurrent with AST) in normally 12 to 20 hours. In certain cases, selective or single purpose media will perform the "isolating", because only one type of organism will grow on a particular medium. Two examples are the ID of *Enterococcus* on Bile Esculin Azide agar or the ID of Coagulase-positive staphylococcus on Tellurite Glycine agar. Reliable ID and AST, using the novel kit and method, may be conducted directly from broth culture.

Many potential variations of the agar, kits, and methods of the invention are possible within the scope of the invention. Some variations of a number of the elements of the present kit and method are listed below. The inoculation of the initial broth culture can be done by using any number of different elements besides a swab. For instance, a syringe and needle serves this purpose as well as any other device that will sample the point of interest containing the microorganism for study. The type of incubation vessel can be any number of different materials. The culture atmosphere can comprise any type and mixture of gas. The way of determining and preparing the density of the bacterial growth for study can be by any number of methods from the McFarland standards to a spectrophotometric determination. The method of inoculating the multi-chambered kit plate can also be different than that shown in the illustrations and described above, as known to one of skill in the art. Suitable methods may likely range from using a multi-pipette to spraying the inoculum onto the kit plate. Any that will allow for the even distribution of inoculum is permissible. Other chemistries that would elucidate the identification of an unknown microorganism from the unique colony of the organism such as newer methods of molecular biology would be permissible such as PCR, immunological methods or other methods heretofore undiscovered to assay the composition of the cellular DNA, antigenic nature, or other molecular features of the specific microorganism.

Included in the kit are reagents and analytical papers for the determination of nitrate reductase and cytochrome oxidase activity in the microorganisms growing from the specimen. However, other reagents in various forms can be utilized in the method. Other embodiments could utilize discs or similar material impregnated with various enzyme substrates, carbohydrates, or with various chemical agents for differentiating microorganisms on the identification section of the kit plate. Each of these differentiation discs may be used for presumptive identification of specific organisms. The carbohydrate discs are for the differentiation of microorganisms based on carbohydrate fermentation patterns. In addition, an anaerobe differentiation disc set may be used in the presumptive identification of gram-negative anaerobic bacilli.

Databases can be developed for searching gram-positive microorganisms as is shown for gram-negative microorganisms in the kit and method. It is possible to generate a set of criteria from the kit results for these and other types of microorganisms. In addition, it is practical to generate additional criteria using additional methods of biochemistry for more definitive identification.

The process of preserving the kit plates for later use comprise the packaging and storage under a nitrogen atmosphere performed in a glove box in a low permeability bag. Other embodiments would be to package under nitrogen in a Mylar-foil bag for complete protection against oxygen. Another inert gas could be used to package the kit plates also with another type of impermeable bag or container.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by U.S. Letters Patent is:

1. A microbial culture medium comprising:
    an agar medium; and
    iota carrageenan, wherein the iota carrageenan is present in an amount sufficient to stabilize the microbial culture medium.

2. The microbial culture medium of claim 1, wherein the agar medium is selected from the group consisting of: A8 agar; *Actinomycete* Isolation Agar; Agar Medium No. F; American trudeau Society medium; Anaerobic Agar; Azide Blood Agar Base; *Bacillus cereus* selective agar (BCA); *Bacteroides* Bile-Esculin agar; BG Sulfa Agar; Baird-Parker Agar Base; BIGGY Agar; Bile Esculin Agar Base; Bile Esculin Agar; Bile Esculin Azide Agar; Bismuth sulfite agar; Blood agar; anaerobic (CDC); Blood agar; anaer. W K & Val (CDC); Blood Agar Base; Blood Agar Base No. 2; Blood Agar, Laked, anaerobic with K & VA; Blood Agar, Phenylethyl alcohol, anaerobic; Bordet Gengou Agar Base; Brain Heart Infusion Agar; Brain Heart CC Agar; Brain Heart Infusion w/PAB and Agar; Brewer Anaerobic Agar; Brilliant Green Agar; Brilliant Green Agar Modified; Brilliant Green Bile Agar; *Brucella* Agar; *Campylobacter* Agar Base; *Candida* BCG Agar Base; *Candida* Isolation Agar; Cetrimide Agar Base; Charcoal Agar; Chocolate Agar; Clostridium difficile selective media; Columbia Blood Agar Base EH; Columbia Blood Agar Base; Columbia Blood Agar Base No. 2; Cooke Rose Bengal Agar; Corn Meal Agar; Cystine Heart Agar; Cystine Tryptic Agar; Czapek Solution Agar; DCLS Agar; D/E Neutralizing Agar; DNase Test Agar w/Methyl Green; DRBC Agar; Desoxycholate Agar; Desoxycholate Citrate Agar; Desoxycholate Lactose Agar; Dextrose Agar; Dextrose Starch Agar; Dextrose Tryptone Agar; Differential Reinforced Clostridial Agar; Dubos Oleic Agar Base; Egg Yolk Agar; M E Agar; Esculin Iron Agar; EMB Agar; Emerson YpSs Agar; Endo Agar; M *Enterococcus* Agar; Eugon Agar; M FC Agar; HC Agar Base; M HPC Agar; Heart Infusion Agar; Hektoen Enteric Agar; KF *Streptococcus* Agar; LPM Agar Base; *Lactobacilli* MRS Agar; Letheen Agar; Lima Bean Agar; Littman Oxgall Agar; Liver Infusion Agar; Liver Veal Agar; M 17 Agar; MYP Agar; MacConkey Agar; MacConkey Agar Base; MacConkey Agar CS; MacConkey Agar w/o Salt; MacConkey Agar w/o CV; MacConkey Sorbitol Agar; Malt Agar; Malt Extract Agar; Mannitol Salt Agar; McBride Listeria Agar; McClung Toabe Agar Base; Microbial Content Test Agar; Mueller-Hinton medium plain; Mueller-Hinton m. with 5% sheep B.; Mueller-Hinton m. chocolatized; *Mycobacteria* 7HI I Agar; Milk Agar; ;Mitis *Salivarius* Agar; Modified Letheen Agar; Mycobiotic Agar; Mycological Agar; Mycological Agar w/Low pH; Oatmeal Agar; Orange Serum Agar; PPLO Agar; Peptone Iron Agar; Phenylethanol Agar; Phenylalanine Agar; Potato Dextrose Agar; Protease No. 3 Agar; *Pseudomonas* Agar F; *Pseudomonas* Agar P; *Pseudomonas* Isolation Agar; Rice Extract Agar; Rose Bengal Agar Base; SABHI Agar Base; SPS Agar; Sabouraud Dextrose Agar; *Salmonella-Shigella* Agar; Sabouraud Maltose Agar; Simmons Citrate Agar; Spirit Blue Agar; TCBS Agar; M TEC Agar; TPEY Agar Base; Tellurite Glycine Agar; Thermoacidurans Agar; Thiosulfate citrate bile salts sucrose agar; Tomato Juice Agar; Tomato Juice Agar Special; Triple Sugar Iron Agar; Tryptic Soy Agar; Tryptone Glucose Extract Agar; Tryptose Agar; Tryptose Blood Agar Base; VJ Agar; Veal Infusion Agar; Veillonella Agar; Violet Red Bile Agar; Violet Red Bile Agar with MUG; Violet Red Bile Glucose Agar; XLD Agar; XLT4 Agar Base; YM Agar; Yeast Extract Glucose Chloramphenicol Agar; and Yersinia Selective Agar Base.

3. The microbial culture medium of claim 2, wherein the iota carrageenan is about 1% of the medium by weight.

4. The microbial culture medium of claim 3, wherein the iota carrageenan is from about 0.1% to about 0.8% of the medium by weight.

5. The microbial culture medium of claim 4, wherein the iota carrageenan is from about 0.1% to about 0.4% of the medium by weight.

6. The microbial culture medium of claim 5, wherein the iota carrageenan is from about 0.2% of the medium by weight.

7. The microbial culture medium of claim 2, further comprising alkaline earth metal ions.

8. The microbial culture medium of claim 7, wherein the alkaline earth metal ions are present at a concentration of less than about 10 mM.

9. The microbial culture medium of claim 8, wherein the alkaline earth metal ions are present at a concentration of from about 0.1 mM to about 10 mM.

10. The microbial culture medium of claim 9, wherein the alkaline earth metal ions are present at a concentration of about 1 mM.

11. The microbial culture medium of claim 7, wherein the alkaline earth metal ions are calcium ions.

12. The microbial culture medium of claim 11, wherein the calcium ions are present at a concentration of less than about 10 mM.

13. The microbial culture medium of claim 12, wherein the calcium ions are present at a concentration of from about 0.01 mM to about 10 mM.

14. The microbial culture medium of claim 13, wherein the calcium ions are present at a concentration of about 1 mM.

15. The microbial culture medium of claim 1, wherein the iota carrageenan is about 1% of the medium by weight.

16. The microbial culture medium of claim 15, wherein the iota carrageenan is from about 0.1% to about 0.8% of the medium by weight.

17. The microbial culture medium of claim 16, wherein the iota carrageenan is from about 0.1% to about 0.4% of the medium by weight.

18. The microbial culture medium of claim 17, wherein the iota carrageenan is from about 0.2% of the medium by weight.

19. The microbial culture medium of claim 1, further comprising alkaline earth metal ions.

20. The microbial culture medium of claim 19, wherein the alkaline earth metal ions are present at a concentration of less than about 10 mM.

21. The microbial culture medium of claim 20, wherein the alkaline earth metal ions are present at a concentration of from about 0.1 mM to about 10 mM.

22. The microbial culture medium of claim 21, wherein the alkaline earth metal ions are present at a concentration of about 1 mM.

23. The microbial culture medium of claim 19, wherein the alkaline earth metal ions are calcium ions.

24. The microbial culture medium of claim 23, wherein the calcium ions are present at a concentration of less than about 10 mM.

25. The microbial culture medium of claim 24, wherein the calcium ions are present at a concentration of from about 0.01 mM to about 10 mM.

26. The microbial culture medium of claim 25, wherein the calcium ions are present at a concentration of about 1 mM.

27. A microbial culture medium comprising:
   Mueller-Hinton agar; and
   iota carrageenan, wherein the iota carrageenan is present in an amount sufficient to stabilize the microbial culture medium.

28. The microbial culture medium of claim 27, wherein the iota carrageenan is about 1% of the medium by weight.

29. The microbial culture medium of claim 28, wherein the iota carrageenan is from about 0.1% to about 0.8% of the medium by weight.

30. The microbial culture medium of claim 29, wherein the iota carrageenan is from about 0.1% to about 0.4% of the medium by weight.

31. The microbial culture medium of claim 30, wherein the iota carrageenan is from about 0.2% of the medium by weight.

32. The microbial culture medium of claim 27, further comprising alkaline earth metal ions.

33. The microbial culture medium of claim 32, wherein the alkaline earth metal ions are present at a concentration of less than about 10 mM.

34. The microbial culture medium of claim 33, wherein the alkaline earth metal ions are present at a concentration of from about 0.1 mM to about 10 mM.

35. The microbial culture medium of claim 34, wherein the alkaline earth metal ions are present at a concentration of about 1 mM.

36. The microbial culture medium of claim 32, wherein the alkaline earth metal ions are calcium ions.

37. The microbial culture medium of claim 36, wherein the calcium ions are present at a concentration of less than about 10 mM.

38. The microbial culture medium of claim 37, wherein the calcium ions are present at a concentration of from about 0.01 mM to about 10 mM.

39. The microbial culture medium of claim 38, wherein the concentration of about 1 mM.

* * * * *